United States Patent
Lin et al.

(10) Patent No.: US 11,951,211 B2
(45) Date of Patent: Apr. 9, 2024

(54) DNA BRICK-ASSISTED LIPOSOME SORTING

(71) Applicant: Yale University, New Haven, CT (US)

(72) Inventors: Chenxiang Lin, Orange, CT (US); Yang Yang, Watertown, MA (US)

(73) Assignee: YALE UNIVERSITY, New Haven, CT (US)

( * ) Notice: Subject to any disclaimer, the term of this patent is extended or adjusted under 35 U.S.C. 154(b) by 354 days.

(21) Appl. No.: 17/162,008

(22) Filed: Jan. 29, 2021

(65) Prior Publication Data
US 2021/0267894 A1 Sep. 2, 2021

Related U.S. Application Data

(60) Provisional application No. 62/968,683, filed on Jan. 31, 2020.

(51) Int. Cl.
*A61K 9/127* (2006.01)
*A61K 47/69* (2017.01)

(52) U.S. Cl.
CPC .......... *A61K 9/1272* (2013.01); *A61K 9/1277* (2013.01); *A61K 47/6913* (2017.08)

(58) Field of Classification Search
CPC .............................. A61K 9/127; A61K 9/1272
See application file for complete search history.

(56) References Cited

U.S. PATENT DOCUMENTS

| 2008/0317840 | A1* | 12/2008 | Lee ........................ A61P 25/00 435/375 |
| 2016/0194642 | A1* | 7/2016 | Gryaznov ............... A61P 37/00 424/193.1 |
| 2018/0344873 | A1* | 12/2018 | Mirkin ............... A61K 47/6929 |
| 2019/0029959 | A1* | 1/2019 | Costa ................ B01F 35/21112 |

OTHER PUBLICATIONS

Zhao Zhang, Yang Yang, Frederic Pincet, Marc C. Llaguno and Chenxiang Lin. "Placing and shaping liposomes with reconfigurable DNA nanocages." Nature Chemistry, vol. 9, 2017, pp. 653-659 + 58 pages of Supplementary Information, available online Jun. 23, 2017. (Year: 2017).*
Hendrik Dietz, Shawn M. Douglas, William M. Shih. "Folding DNA into Twisted and Curved Nanoscale Shapes." Science, vol. 325, Aug. 7, 2009, pp. 725-730. (Year: 2009).*
Yu He, Yi Chen, Haipeng Liu, Alexander E. Ribbe, and Chengde Mao. "Self-Assembly of Hexagonal DNA Two-Dimensional (2D) Arrays." Journal of the American Chemical Society, vol. 127, 2005, pp. 12202-12203 (Year: 2005).*

(Continued)

*Primary Examiner* — Isaac Shomer
(74) *Attorney, Agent, or Firm* — Troutman Pepper Hamilton Sanders LLP

(57) ABSTRACT

A method for producing uniform-size liposomes is provided. The liposomes are coated with a sorting agent to yield a plurality of density-modified liposomes of different sizes. These liposomes are then separated using a densitometric method. The sorting agent includes both a density-modifying moiety and a targeting moiety.

18 Claims, 41 Drawing Sheets
(23 of 41 Drawing Sheet(s) Filed in Color)
Specification includes a Sequence Listing.

(56) References Cited

OTHER PUBLICATIONS

Erik Goormaghtigh and Gene A. Scarborough. "Density-Based Separation of Liposomes by Glycerol Gradient Centrifugation." Analytical Biochemistry, vol. 159, 1986, pp. 122-131. (Year: 1986).*
Sebastien Benizri, Arnaud Gissot, Andrew Martin, Brune Vialet, Mark W. Grinstaff, and Philippe Barthélémy. "Bioconjugated Oligonucleotides: Recent Developments and Therapeutic Applications." vol. 30, pp. 366-383, published Jan. 4, 2019. (Year: 2019).*
Oligo Calc: Oligonucleotide Properties Calculator (for Single Stranded Nucleic Acid). biotools.nubic.northwestern.edu/OligoCalc.html accessed Aug. 3, 2023, 5 printed pages. (Year: 2023).*
Oligo Calc: Oligonucleotide Properties Calculator (for Double Stranded Nucleic Acid). biotools.nubic.northwestern.edu/OligoCalc. html accessed Aug. 3, 2023, 5 printed pages. (Year: 2023).*
V. Sánchez-López, J.M. Fernández-Romero, A. Gómez-Hens. "Evaluation of liposome populations using a sucrose density gradient centrifugation approach coupled to a continuous flow system." Analytica Chimica Acta, vol. 645, 2009, pp. 79-85. (Year: 2009).*
Angela Ecija-Arenas, Vanesa Roman-Pizarro, Juan Manuel Fernandez-Romero. "Luminescence continuous flow system for monitoring the efficiency of hybrid liposomes separation using multiphase density gradient centrifugation." Talanta, vol. 222, 2021, Article 121532, 7 pages. (Year: 2021).*
Czogalla et al.; Amphipathic DNA Origami Nanoparticles to Scaffold and Deform Lipid Membrane Vesicles; Angew. Chem. Int. Ed. 2015; 54; 6501-5.
Federal RePORTER; Cell-Free Membrane Remodeling Guided by DNA Nano-Templates; Project Information; 2020; 15 pages.
Franquelim et al.; Membrane sculpting by curved DNA origami scaffolds; Nat. Comm.; (2018); 9:811; 10 pages.
Grome; Vesicle tubulation with self-assembling DNA nanosprings; Angew Chem Int Ed Engl. May 4, 2018; 57(19): 5330-4.
NIH RePORTER; A Nanomechanical Toolkit to Guide Membrane Structure and Dynamics; Project Information; Project No. 1R01GM132114-01; 2020; 1 page.
Perrault et al.; Virus-Inspired Membrane Encapsulation of DNA Nanostructures to Achieve In Vivo Stability; ACS Nano; 8(5); 2014; 5132-40.
Yang et al.; Sorting liposomes of distinct sizes by DNA-brick assisted centrifugation; bioRxiv; Feb. 2020; 13 pages.
Yang et al.; Sorting liposomes of distinct sizes by DNA-brick assisted centrifugation; bioRxiv; 2020; Supplementary Information; 19 pages.
Yang et al.; Self-assembly of size-controlled liposomes on DNA nanotemplates; Nat Chem.; May 2016; 8(5): 476-83.
Zhang et al.; Placing and shaping liposomes with reconfigurable DNA nanocages; Nat Chem. Jun. 23, 2017; 9(7): 653-9.

* cited by examiner

FIG. 17

SEQUENCE LISTING

<160> NUMBER OF SEQ ID NOS: 26

<210> SEQ ID NO 1
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aggcatattg aatcgtttac aggattagta attaacagct ttaatatcat cgcccatcgt    60
aggtttcttg cc                                                        72

<210> SEQ ID NO 2
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggcatattg aatcgtttac aggattagta attaacagct ttaatatcat cgcccatcgt    60
aggtttcttg cc                                                        72

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gacgacagag gttgctaggc g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttaccgtgtg tgttaaggtg g                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
accgagcctc cgtcaacatc g                                              21

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccaccttaac acgcgatgat attgctgtta attaggctcg gt                       42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgatgttgac ggactaatcc tgtcgattca atatctgtcg tc                       42

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 8
cgcctagcaa cctgcctggc aagcctacga tggacacggt aa                             42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgcctagcaa cctgcctggc aagcctacga tggacacggt aa                             42

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tttagtgcta cactgtgcgt atgcgaaaac ttgcgatatg ctccattt                       48

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttagtcgag tgaactgtaa cgtacaggta gatagactct gtatcttt                       48

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaattatcta ccacaactca ccgcctagca acctgcctgg caagcctacg atggacacgg          60
taa                                                                       63

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttattcgag catgtcagtg gatcaatcgt gttagacatg acgtattt                       48

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 14
tttgtggact atatatacgt ggaaccatga attggctgag tttggttt          48

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttttggttta ctcactattg tcaccttata ccacaatcag atccgttt          48

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cacagtggat tgtgtatata tagtccacta cgtcactagg cg                42

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagttcagtc catctgacat gctcgaatcc aaacttaaac ca                42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttaccgtctc gacttggagc atatcgcata gtgagcagcc aa                42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cacgattttc cacggtataa ggtgacaaag ttttctacgt ta                42

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cacgattttc cacggtataa ggtgacaaag ttttctacgt ta                               42

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttcatgggat ccacgtaggc ttgccaggct acctggcata cg                              42

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cggatcttag cactgataca gagtctatca ggttgtgtct aa                              42

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtgagttgtg gtagataatt t                                                     21

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
catgtacagc catagttgag cattaagttg aagtggctgt acatg                           45

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

His His His His His His
1               5

```
<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtgagttgtg gtagataatt t                                              21
```

DNA BRICK-ASSISTED LIPOSOME SORTING

CROSS-REFERENCE TO RELATED APPLICATIONS

This application claims priority to U.S. Provisional Application No. 62/968,683, filed Jan. 31, 2020, which application is herein incorporated by reference in its entirety.

STATEMENT REGARDING FEDERALLY SPONSORED RESEARCH OR DEVELOPMENT

This invention was made with government support under GM114830 and GM132114 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on May 4, 2021, is named 251609_000038_SL.txt and is 6,562 bytes in size.

FIELD OF THE INVENTION

The invention relates to methods and compositions for stabilizing and sorting liposomes. In particular, the invention relates to methods for using a sorting agent to assist in sorting liposomes using a densitometric method, to methods for using the sorting agent to stabilize liposomes, and to compositions comprising density-sorted liposomes, the sorting agent, or a combination thereof.

BACKGROUND

Vesicles and liposomes can be understood as "tiny bubbles of fluid" wrapped by lipid-bilayer membranes. Vesicles are abundant in cells and extracellular spaces, performing tasks that include nutrient uptake, cargo transport, and waste confinement. Vesicles on different missions and transport routes are often distinct in size and chemical compositions, which confers specificity to their interactions with other membranous compartments. Liposomes have been widely studied as drug-delivery vehicles. Liposomes of different sizes differ in geometrical (e.g., surface/volume ratio, membrane curvature) and physiochemical (e.g., lipid packing defects) properties that may affect the liposomes' biochemical and pharmacological functions. Existing methods are unsuitable for scalable production of uniform-size liposomes across a wide range of dimensions and compositions.

There is a need for improved methods to provide uniform-size liposomes or vesicles across a wide range of diameters and lipid compositions.

Existing methods for controlling liposome size rely on liposome formation conditions [1-3] (e.g. lipid composition and solvent-to-water mixing ratio) as well as post-formation homogenization [4-5] (e.g. extrusion and sonication) and purification [40-41] (e.g. centrifugation and size-exclusion chromatography). The production outcome is tied to a set of empirically determined parameters that may not be independently tunable, thus limiting users' ability to selectively vary the liposome size and composition. Microfluidic-based systems provide a way to tune liposome size and dispersity, but often require nonstandard, built-in-house devices [6-7]. Additionally, the method's capability to make functional proteoliposomes has not been demonstrated. Another approach is to guide lipid-bilayer self-assembly using DNA nanotemplates [8-10]. While effective in forming size-controlled liposomes with programmable membrane-protein stoichiometry, this approach is cost-ineffective for mass production due to the requirement of a unique DNA template for each liposome configuration, a low scale of preparation (typically less than a few micrograms), and relatively low lipid recovery. Moreover, the use of detergent limits the selection of compatible cargo molecules.

There remains, therefore, a need to develop a streamlined, high-throughput, scalable sorting method for differentiating hetero-sized liposomes of various membrane composition, a wide range of diameters, and having various internal contents into narrowly distributed sizes while preserving the liposomes' original characteristics. There remains a need too for a sorting method that may be used in conjunction with an assortment of liposome manufacturing methods. There remains a need for a method allowing for study with unprecedented resolution how membrane curvature influences activity of membrane proteins. There also remains a need for a method that will facilitate a quantitative understanding of membrane curvature in various cellular processes including vesicular transport.

SUMMARY OF THE INVENTION

The disclosure provides for improved methods for preparing uniform-sized liposomes.

In one aspect is provided a method for producing uniform-size liposomes, the method comprising:

coating a plurality of liposomes with a sorting agent to yield a plurality of density-modified liposomes of different sizes; and separating the density-modified liposomes of different sizes using a densitometric method, where the sorting agent comprises a density-modifying moiety and a targeting moiety.

In some embodiments, the density of the sorting agent is higher than the density of the liposome. In some embodiments, the density of an individual density-modified liposome is inversely related to the radius of the individual density-modified liposome. In some embodiments, the method further comprising isolating one or more fractions of uniform-size liposomes. In some embodiments, the liposomes within each of the one or more isolated fractions have a coefficient of variation of less than 15%.

In some embodiments, the density-modifying moiety comprises a polynucleotide. In some embodiments, the targeting moiety is bound to a nucleotide base within the polynucleotide. In some embodiments, the targeting moiety is bound to a 5' end of the polynucleotide. In some embodiments, the targeting moiety is bound to a 3' end of the polynucleotide. In some embodiments, the polynucleotide is DNA or RNA. In some embodiments, the polynucleotide is DNA. In some embodiments, the polynucleotide is RNA.

In some embodiments, the molecular mass of the density-modifying moiety is from 1 to 1,000 kDa. In some embodiments, the molecular mass of the density-modifying moiety is from 50 to 250 kDa. In some embodiments, the density-modifying moiety forms a polynucleotide nanostructure. In some embodiments, the density-modifying moiety forms a three-point star structure. In some embodiments, the molecular mass of the three-point star structure is from 75 to 100 kDa. In some embodiments, the molecular mass of the three-point star structure is from 80 to 90 kDa. In some embodiments, the molecular mass of the three-point star structure is 86 kDa.

In some embodiments, the density-modifying moiety comprises a sequence at least 85% identical to AGGCATATTGAATCGTTTACAGGATTAGTAATTAACAGCTTTAATATCATCGCCCATCGTAG GTTTCTTGCC (SEQ ID NO: 1).

In some embodiments, the density-modifying moiety comprises a sequence at least 85% identical to GACGACAGAGGTTGCTAGGCG (SEQ ID NO: 3).

In some embodiments, the density-modifying moiety comprises a sequence at least 85% identical to TTACCGTGTGTGTTAAGGTGG (SEQ ID NO: 4).

In some embodiments, the density-modifying moiety comprises a sequence at least 85% identical to ACCGAGCCTCCGTCAACATCG (SEQ ID NO: 5).

In some embodiments, the density-modifying moiety comprises a sequence at least 85% identical to CCACCTTAACACGCGATGATATTGCTGTTAATTAGGCTCGGT (SEQ ID NO: 6).

In some embodiments, the density-modifying moiety comprises a sequence at least 85% identical to CGATGTTGACGGACTAATCCTGTCGATTCAATATCTGTCGTC (SEQ ID NO: 7).

In some embodiments, the density-modifying moiety comprises a sequence at least 85% identical to CGCCTAGCAACCTGCCTGGCAAGCCTACGATGGACACGGTAA (SEQ ID NO: 8).

In some embodiments, the density-modifying moiety comprises a sequence at least 85% identical to CGCCTAGCAACCTGCCTGGCAAGCCTACGATGGACACGGTAA (SEQ ID NO: 8).

In some embodiments, the density-modifying moiety forms a six-helix bundle structure.

In some embodiments, the molecular mass of the six-helix bundle structure is from 150 to 250 kDa. In some embodiments, the molecular mass of the six-helix bundle structure is from 180 to 200 kDa. In some embodiments, the molecular mass of the six-helix bundle structure is 189 kDa.

In some embodiments, the density-modifying moiety comprises a sequence at least 85% identical to TTTAGTGCTACACTGTGCGTATGCGAAAACTTGCGATATGCTCCATTT (SEQ ID NO: 10).

In some embodiments, the density-modifying moiety comprises a sequence at least 85% identical to TTTAGTCGAGTGAACTGTAACGTACAGGTAGATAGACTCTGTATCTTT (SEQ ID NO: 11).

In some embodiments, the density-modifying moiety comprises a sequence at least 85% identical to AAATTATCTACCACAACTCACCGCCTAGCAACCTGCCTGGCAAGCCTACGATGGACACGGT AA (SEQ ID NO: 12).

In some embodiments, the density-modifying moiety comprises a sequence at least 85% identical to TTTATTCGAGCATGTCAGTGGATCAATCGTGTTAGACATGACGTATTT (SEQ ID NO: 13).

In some embodiments, the density-modifying moiety comprises a sequence at least 85% identical to TTTGTGGACTATATATACGTGGAACCATGAATTGGCTGAGTTTGGTTT (SEQ ID NO: 14).

In some embodiments, the density-modifying moiety comprises a sequence at least 85% identical to TTTTGGTTTACTCACTATTGTCACCTTATACCACAATCAGATCCGTTT (SEQ ID NO: 15).

In some embodiments, the density-modifying moiety comprises a sequence at least 85% identical to CAGTTCAGTCCATCTGACATGCTCGAATCCAAACTTAAACCA (SEQ ID NO: 17).

In some embodiments, the density-modifying moiety comprises a sequence at least 85% identical to TTACCGTCTCGACTTGGAGCATATCGCATAGTGAGCAGCCAA (SEQ ID NO: 18).

In some embodiments, the density-modifying moiety comprises a sequence at least 85% identical to CACGATTTTCCACGGTATAAGGTGACAAAGTTTTCTACGTTA (SEQ ID NO: 19).

In some embodiments, the density-modifying moiety comprises a sequence at least 85% identical to TTCATGGGATCCACGTAGGCTTGCCAGGCTACCTGGCATACG (SEQ ID NO: 21).

In some embodiments, the density-modifying moiety comprises a sequence at least 85% identical to CGGATCTTAGCACTGATACAGAGTCTATCAGGTTGTGTCTAA (SEQ ID NO: 22).

In some embodiments, the density-modifying moiety comprises a sequence at least 85% identical to GTGAGTTGTGGTAGATAATTT (SEQ ID NO: 26).

In some embodiments, the liposome is produced by a method selected from extrusion, sonication, and membrane-protein reconstitution.

In some embodiments, the liposomes are coated with the sorting agent under conditions where the sorting agent is present in excess so as to achieve dense coating of the liposomes. In some embodiments, the liposomes are coated with the sorting agent at a ratio of liposomes to sorting agent of from 1:10 to 1:1000.

In some embodiments, an external surface of the liposomes is saturated with the sorting agent. In some embodiments, the sorting agent comprises only one targeting moiety. In some embodiments, the targeting moiety comprises a hydrophobic molecule or a protein-specific ligand. In some embodiments, the protein-specific ligand is an antibody, an aptamer, or a small organic molecule. In certain embodiments, the hydrophobic molecule is a lipid. In certain embodiments, the lipid is a cholesterol. In certain embodiments, the cholesterol is bound to the targeting moiety via a spacer.

In some embodiments, the targeting moiety comprises an antibody or protein-specific ligand. In some embodiments, the plurality of liposomes has an average diameter of greater than 100 nm. In certain embodiments, the targeting moiety comprises the density-modifying moiety forming a six-helix bundle structure. In some embodiments, the average diameter of the plurality of liposomes is less than 100 nm. In certain embodiments, the targeting moiety comprises the density-modifying moiety forming a three-point star structure.

In some embodiments, the sorting agent has a buoyant density of from about 1.25 g/mL to about 2 g/mL. In some embodiments, the densitometric method is isopycnic centrifugation. In certain embodiments, the isopycnic centrifugation is carried out using an iodixanol density gradient. In certain embodiments, the iodixanol density gradient comprises an approximately linear gradient of iodixanol ranging from about 0 wt % iodixanol to about 30 wt % iodixanol. In certain embodiments, the yield of liposomes recovered from the separating step is at least 80%. In some embodiments, the liposomes comprise membrane-bound proteins. In some embodiments, the liposomes comprise surface markers.

In some embodiments, the method further comprises collecting a density-sorted fraction of the plurality of liposomes sorted using the densitometric method. In some embodiments, the density-sorted fraction comprises liposomes having a mean diameter of less than 500 nm.

In some embodiments, at least 90% of the liposomes have a diameter within about 83% to about 117% of the mean diameter of all of the liposomes present in the density-sorted fraction. In some embodiments, at least 90% of the liposomes have a diameter from 110 nm to 150 nm. In some embodiments, at least 90% of the liposomes have a diameter from 99 nm to 132 nm. In some embodiments, at least 90% of the liposomes have a diameter from 93 nm to 126 nm. In some embodiments, at least 90% of the liposomes have a diameter from 86 nm to 113 nm. In some embodiments, at least 90% of the liposomes have a diameter from 65 nm to 88 nm. In some embodiments, at least 90% of the liposomes have a diameter from 53 nm to 75 nm.

In some embodiments, the liposomes are prepared by extrusion, sonication, membrane-protein reconstitution, or a combination thereof. In some embodiments, the liposomes comprise one or more markers. In certain embodiments, the marker is dioleoylphosphatidylcholine (DOPC), dioleoylphosphatidylethanolamine (DOPE), dioleoylphosphatidylserine (DOPS), rhodamine-DOPE, and N-(7-nitrobenz-2-oxa-1,3-diazol-4-yl)-1,2-dihexadecanoyl-sn-glycerol-3-phosphoethanolamine (NBD-PE).

In some embodiments, the liposomes comprise from about 0 wt % to about 5 wt % rhodamine-DOPE. In some embodiments, the density-modifying moiety is a polynucleotide, and the method further comprising separating the density-modifying moiety from the targeting moiety using a nuclease after the separating step. In some embodiments, the nuclease is DNase I.

In some embodiments, the liposomes comprise a pharmaceutical agent. In some embodiments, the pharmaceutical agent is disposed within a lumen of the liposomes both before and after the separating step. In some embodiments, the amount of the pharmaceutical agent in the liposomes after the separating step is at least 80% of the amount of the pharmaceutical agent in the liposomes before the separating step. In some embodiments, the method further comprises removing or dissociating the targeting moiety from the liposomes after the separating step.

In some embodiments, the targeting moiety is cholesterol, and wherein the cholesterol is removed by contacting the coated liposomes with cyclodextrin. In some embodiments, the targeting moiety comprises a polynucleotide, and wherein the targeting moiety is removed by contacting the coated liposomes with a nuclease. In some embodiments, the targeting moiety comprises a polypeptide, and wherein the targeting moiety is removed by contacting the coated liposomes with a protease.

In some embodiments, the sorting agent comprises an oligonucleotide labeled with a dye or a fluorophore. In certain embodiments, the dye or fluorophore is Cy5.

In some embodiments, the method further comprises loading the obtained liposomes with a drug.

In another aspect is provided a method for production of uniform-size liposomes, the method comprising:
coating a plurality of liposomes with cholesterol-modified oligonucleotides to yield a plurality of density-modified liposomes of different sizes,
separating the density-modified liposomes of different sizes by isopycnic centrifugation, and
isolating one or more fractions of uniform-size liposomes.

In some embodiments, the cholesterol-modified oligonucleotides comprise DNA. In some embodiments, the cholesterol-modified oligonucleotides comprise RNA. In some embodiments, the cholesterol-modified oligonucleotides comprise a DNA/RNA hybrid structure.

In some embodiments, the cholesterol-modified DNA oligonucleotide is a six-helix-bundle rod of about 189 kD with a single cholesterol at the end of each DNA structure. In certain embodiments, the size of the liposome is greater than 100 nm.

In some embodiments, the cholesterol-modified DNA oligonucleotide is a three-pointed star of about 86 kD with a single cholesterol at the end of each DNA structure. In certain embodiments, the size of the liposome is less than 40 nm.

In another aspect is provided a composition comprising density-sorted liposomes prepared according to any of the methods described above. In some embodiments, the density-sorted liposomes are substantially leak-free liposomes. In some embodiments, the density-sorted liposomes are leak-free liposomes. In some embodiments, the density-sorted liposomes are substantially impermeable to fluorescein or a divalent cation. In certain embodiments, the divalent cation is zinc. In certain embodiments, the density-sorted liposomes are impermeable to fluorescein or a divalent cation.

In another aspect is provided a sorting agent comprising a density-modifying moiety and a targeting moiety, wherein the density-modifying moiety is a nucleotide-brick. In some embodiments, the density-modifying moiety comprises a polynucleotide. In some embodiments, the targeting moiety is bound to a nucleic acid within the polynucleotide, a 5' end of the polynucleotide, or a 3' end of the polynucleotide. In some embodiments, the polynucleotide is DNA or RNA. In certain embodiments, the polynucleotide is DNA. In certain embodiments, the polynucleotide is RNA.

In some embodiments, the molecular mass of the density-modifying moiety is from 50 to 250 kDa. In various embodiments, the density-modifying moiety forms a three-point star structure. In some embodiments, the molecular mass of the three-point star structure is from 75 to 100 kDa. In some embodiments, the molecular mass of the three-point star structure is from 80 to 90 kDa. In some embodiments, the molecular mass of the three-point star structure is 86 kDa.

In some embodiments, the density-modifying moiety comprises a sequence at least 85% identical to AGGCATATTGAATCGTTTACAGGATTAGTAATTAACAGCTTTAATATCATCGCCCATCGTAG GTTTCTTGCC (SEQ ID NO: 1).

In some embodiments, the density-modifying moiety comprises a sequence at least 85% identical to GACGACAGAGGTTGCTAGGCG (SEQ ID NO: 3).

In some embodiments, the density-modifying moiety comprises a sequence at least 85% identical to TTACCGTGTGTGTTAAGGTGG (SEQ ID NO: 4).

In some embodiments, the density-modifying moiety comprises a sequence at least 85% identical to ACCGAGCCTCCGTCAACATCG (SEQ ID NO: 5).

In some embodiments, the density-modifying moiety comprises a sequence at least 85% identical to CCACCTTAACACGCGATGATATTGCTGTTAATTAGGCTCGGT (SEQ ID NO: 6).

In some embodiments, the density-modifying moiety comprises a sequence at least 85% identical to CGATGTTGACGGACTAATCCTGTCGATTCAATATCTGTCGTC (SEQ ID NO: 7).

In some embodiments, the density-modifying moiety comprises a sequence at least 85% identical to CGCCTAGCAACCTGCCTGGCAAGCCTACGATGGACACGGTAA (SEQ ID NO: 8).

In some embodiments, the density-modifying moiety comprises a sequence at least 85% identical to CGCCTAGCAACCTGCCTGGCAAGCCTAC-GATGGACACGGTAA (SEQ ID NO: 8).

In some embodiments, the density-modifying moiety forms a six-helix bundle structure. In some embodiments, the molecular mass of the six-helix bundle structure is from 150 to 250 kDa. In some embodiments, the molecular mass of the six-helix bundle structure is from 180 to 200 kDa. In certain embodiments, the molecular mass of the six-helix bundle structure is 189 kDa.

In some embodiments, the density-modifying moiety comprises a sequence at least 85% identical to TTTAGTGC-TACACTGTGCGTATGCGAAAACTTGCGATATGCTC-CATTT (SEQ ID NO: 10).

In some embodiments, the density-modifying moiety comprises a sequence at least 85% identical to TTTAGTCGAGTGAACTGTAACGTACAGGTAGATA-GACTCTGTATCTTT (SEQ ID NO: 11).

In some embodiments, the density-modifying moiety comprises a sequence at least 85% identical to AAATTATC-TACCACAACT-CACCGCCTAGCAACCTGCCTGGCAAGCCTAC-GATGGACACGGT AA (SEQ ID NO: 12).

In some embodiments, the density-modifying moiety comprises a sequence at least 85% identical to TTTAT-TCGAGCATGTCAGTGGATCAATCGTGTTAGA-CATGACGTATTT (SEQ ID NO: 13).

In some embodiments, the density-modifying moiety comprises a sequence at least 85% identical to TTTGTGGACTATATATACGTGGAACCATGAAT-TGGCTGAGTTTGGTTT (SEQ ID NO: 14).

In some embodiments, the density-modifying moiety comprises a sequence at least 85% identical to TTTTGGTT-TACTCACTATTGTCACCTTATACCACAATCA-GATCCGTTT (SEQ ID NO: 15).

In some embodiments, the density-modifying moiety comprises a sequence at least 85% identical to CAGTTCAGTCCATCTGACATGCTCGAATCCAAACT-TAAACCA (SEQ ID NO: 17).

In some embodiments, the density-modifying moiety comprises a sequence at least 85% identical to TTACCGTCTCGACTTGGAGCATATCGCATAGT-GAGCAGCCAA (SEQ ID NO: 18).

In some embodiments, the density-modifying moiety comprises a sequence at least 85% identical to CACGAT-TTTCCACGGTATAAGGTGACAAAGTTTTCTACGTTA (SEQ ID NO: 19).

In some embodiments, the density-modifying moiety comprises a sequence at least 85% identical to TTCATGG-GATCCACGTAGGCTTGCCAGGCTACCTGGCATACG (SEQ ID NO: 21).

In some embodiments, the density-modifying moiety comprises a sequence at least 85% identical to CGGATCT-TAGCACTGATACAGAGTCTATCAGGTTGTGTCTAA (SEQ ID NO: 22).

In some embodiments, the density-modifying moiety comprises a sequence at least 85% identical to GTGAGTTGTGGTAGATAATTT (SEQ ID NO: 26).

In some embodiments, the sorting agent comprises only one targeting moiety. In certain embodiments, the targeting moiety comprises a hydrophobic molecule. In certain embodiments, the hydrophobic molecule is a lipid. In certain embodiments, the lipid is a cholesterol.

In some embodiments, the targeting moiety comprises a spacer, where the cholesterol is bound to the targeting moiety via the spacer, and where the spacer comprises triethylene glycol. In some embodiments, the targeting moiety comprises an antibody or protein-specific ligand. In certain embodiments, the sorting agent has a buoyant density of from about 1.25 g/mL to about 2 g/mL.

In some embodiments, the sorting agent comprises an oligonucleotide labeled with a dye or a fluorophore. In some embodiments, the dye or fluorophore is Cy5.

In another aspect is provided a method of stabilizing a liposome comprising contacting the liposome with any of the above sorting agents to yield a stabilized liposome.

In some embodiments, the stabilized liposome is substantially stable for at least three months at room temperature. In some embodiments, the stabilized liposome is substantially stable for at least twenty weeks at room temperature. In some embodiments, the stabilized liposome is substantially stable for at least six months at room temperature. In some embodiments, the stabilized liposome has substantially the same monodispersity after three months as compared to immediately after the stabilized liposome is prepared. In some embodiments, the stabilized liposome has substantially the same monodispersity after twenty weeks as compared to immediately after the stabilized liposome is prepared. In some embodiments, the stabilized liposome has substantially the same monodispersity after six months as compared to immediately after the stabilized liposome is prepared. In some embodiments, the stabilized liposome has substantially the same intact liposomal boundaries after three months as compared to immediately after the stabilized liposome is prepared. In some embodiments, the stabilized liposome has substantially the same intact liposomal boundaries after twenty weeks as compared to immediately after the stabilized liposome is prepared. In some embodiments, the stabilized liposome has substantially the same intact liposomal boundaries after six months as compared to immediately after the stabilized liposome is prepared.

BRIEF DESCRIPTION OF DRAWINGS

This patent application file contains at least one drawing executed in color. Copies of this patent application with color drawing(s) will be provided by the Office upon request and payment of the necessary fee.

FIG. 1A depicts schematic diagrams of cholesterol-labeled DNA bricks (left panel) and a protocol for brick-assisted liposome sorting (rightmost three panels). The protocol includes liposome coating by DNA bricks, separation of DNA-coated liposomes by isopycnic centrifugation, and removal of DNA bricks from the sorted liposomes. The middle of the rightmost three panels includes monochromatic fluorescence images, represented as circles, of 12 fractions recovered following centrifugation to show spread of liposomes in the density gradient. FIG. 1B depicts a plot showing buoyant densities of naked and DNA-coated liposomes of various sizes. The theoretical values were calculated assuming the buoyant density, footprint, and molecular weight of a six-helix bundle DNA brick to be 1.7 g/cm$^3$, 189 nm$^2$ and 189 kD, respectively, so as to illustrate general trends of liposome density versus size in the presence and absence of DNA coating. FIG. 1C depicts a series of liposomes sorted into distinct sizes, which are further shown as D=mean±SD, with the help of the six-helix-bundle DNA bricks. Representative negative-stain TEM images are shown above the corresponding histograms (N=156-1690) fitted by Gaussian functions. Liposomes are made of ~59.2% 1,2-dioleoyl-sn-glycero-3-phosphocholine (DOPC), 30% 1,2-dioleoyl-sn-glycero-3-phosphoethanolamine (DOPE), 10% 1,2-dioleoyl-sn-glycero-3-phospho-L-serine (DOPS), and 0.8% 1,2-dioleoyl-sn-glycero-3-phosphoethanolamine-N-(lissamine rhodamine B sulfonyl) (rhodamine-DOPE). The scale bar represents 100 nm.

FIG. 2A is a schematic drawing of the leakage assay used to assess the membrane permeability. Fluorescein-labeled deoxyribozymes undergo site-specific hydrolysis when exposed to $Zn^{2+}$ outside of the liposomes. FIG. 2B shows representative TEM images of sorted liposomes containing deoxyribozymes. Fraction numbers (e.g. F6) and liposome diameters (mean±SD, N=131-621) are noted above the corresponding images. The scale bar represents 100 nm. FIG. 2C is a plot showing the lipid-to-deoxyribozyme ratios in sorted liposomes fitted via linear regression (dashed line). FIG. 2D shows the results of an experiment where permeability of liposomes was characterized by SDS-PAGE gel electrophoresis following a deoxyribozyme-based leakage assay. Pseudo-colors: Cy5 (on DNA bricks)=yellow; fluorescein (on deoxyribozymes)=blue; rhodamine (on liposomes)=magenta. Liposomes are made of 59.2% DOPC, 30% DOPE, 10% DOPS, and 0.8% rhodamine-DOPE.

FIG. 3A shows schematic illustrations of GL1-DOPE conjugate (left) and the expected lipidation outcomes on liposomes with differential membrane curvatures (right). FIG. 3B shows the results of an experiment where GL1-lipidation efficiencies on extruded, sonicated and sorted liposomes (~59.2% DOPC, 30% DOPE, 10% DOPS, and 0.8% rhodamine-DOPE) were characterized by gel electrophoresis (top row, stained by Coomassie Blue) and immunoblot against GL1 with an antibody that preferentially recognizes the GL1-PE conformation (bottom row). The numbers (in nm) above lanes represent the nominal pore size of the filters (extruded liposomes) or measured mean diameters (sorted liposomes).

FIG. 4A shows a schematic illustration of the lipid-mixing assay used to monitor membrane fusion. Initially quenched NBD dyes (green) fluoresce following membrane fusion due to a decrease in FRET with rhodamine dyes (magenta). SNARE proteins are shown as blue, yellow (t-SNAREs) and green (VAMP2, v-SNARE) ribbons on the membranes. FIG. 4B depicts representative fluorescence traces showing the kinetics of fusion between unsorted liposomes bearing t-SNAREs and unsorted (red) or sorted (different shades of blue, diameters marked as mean±SD, N>208) liposomes bearing v-SNAREs. Protein-free liposomes are mixed with v-SNARE bearing liposomes as a negative control (black). Liposomes with v-SNAREs are reconstituted with 82% POPC, 12% DOPS, 1.5% Rhodamine-DOPE, 1.5% 1,2-dioleoyl-sn-glycero-3-phosphoethanolamine-N-(7-nitro-2-1,3-benzoxadiazol-4-yl) (NBD-DOPE), and a lipid:protein molar ratio of 200:1 or 400:1. Liposomes with t-SNAREs are reconstituted with 58% 1-palmitoyl-2-oleoyl-glycero-3-phosphocholine (POPC), 25% DOPS, 15% 1-palmitoyl-2-oleoyl-sn-glycero-3-phosphoethanolamine (POPE), 2% phosphatidylinositol 4,5-bisphosphate and a lipid:protein molar ratio of 400:1. FIG. 4C is a graph showing the SNARE copy numbers per liposome (Y-axis) measured from sorted liposomes (mean diameters shown on X-axis) reconstituted with lipid:VAMP2 at molar ratios of 200:1 and 400:1. FIG. 4D shows the results of lipid mixing after 2 hours of fusion reactions (measured by NBD fluorescence, as shown in (B)) plotted against the average diameters of sorted v-SNARE-bearing liposomes (representative TEM images are shown). Means and SDs are based on the dataset of liposomes reconstituted with lipid:VAMP2=200:1. Scale bar: 100 nm.

FIG. 11A shows results obtained using liposome samples prepared using one of three methods including extrusion through 200 nm pores, extrusion through 50 nm pores, and sonication, or using a 1:1:1 total lipid molar ratio of liposomes prepared by each of the three methods. TEM images of non-sorted liposome samples are shown as well as histograms showing diameter distributions in each non-sorted liposome sample. The shown agarose gel images were obtained following SDS-agarose gel electrophoresis of fractions from each liposome sample separated using 3PS DNA brick-assisted sorting. In the agarose gel images, red represents rhodamine-labeled lipid and green depicts Cy5-labeled DNA. Distributions of rhodamine fluorescence within the 1:1:1 liposome mixture was similar to that of the sonicated liposome sample because of a dominant population of <40-nm liposomes in the 1:1:1 mixture. FIG. 11B depicts representative TEM images and diameter histograms of liposome fractions sorted from the 1:1:1 mixture with the help of 3PS DNA bricks.

FIG. 12A shows results from small-scale sorting, see 1× in Table 3, of liposomes of Composition A, see Table 2. Shown in the left panel of FIG. 12A is a pseudo-colored SDS-agarose gel image, where red represents rhodamine-labeled lipid and green represents Cy5-labeled DNA, prepared using indicated density-gradient fractions separated using DNA-brick assisted sorting. In the right panel of FIG. 12A is shown TEM images prepared using indicated fractions. FIG. 12B shows results from small-scale sorting, see 1× in Table 3, of liposomes of Composition C, see Table 2. Shown in the left panel of FIG. 12B is a pseudo-colored SDS-agarose gel image, where red represents rhodamine-labeled lipid and green represents Cy5-labeled DNA, prepared using indicated density-gradient fractions separated using DNA-brick assisted sorting. In the right panel of FIG. 12B is shown TEM images prepared using indicated fractions. FIG. 12C shows results from attempted large-scale sorting, see 10× in Table 3, of liposomes of Composition D, see Table 2. A pseudo-colored SDS-agarose gel image is shown, where red represents rhodamine-labeled lipid and green represents Cy5-labeled DNA, prepared using indicated density-gradient fractions separated using DNA-brick assisted sorting.

FIG. 14A shows images of SDS-agarose gels prepared using fractionated liposome before (top) and after (bottom) nuclease treatment of the fractionated liposomes. One unit of DNase I was added to 100 µL of fractionated liposomes coated by 3PS DNA bricks and incubated at 37° C. for 24 hours. Pseudo-color green depicts Cy5-labeled DNA and red depicts rhodamine-labeled lipid. FIG. 14B shows TEM images of indicated fractions showing liposomes treated by DNase I for 2 or 24 hours, as indicated.

FIG. 17 depicts Western blot analyses of ATG7/ATG3 catalyzed GL1 lipidation carried out using sorted liposomes from five separate batches/preparations.

FIG. 18B shows a line representing a linear regression of reference band intensity on corresponding mass of applied protein (black dots) to generate a calibration curve. The linear regression was used to calculate amount of VAMP2 in proteoliposomes (red dots) before and after sorting, see FIG. 18B. FIG. 18C shows representative TEM images of VAMP2-containing liposomes after sorting. Fraction numbers and mean liposome diameters are indicated on top of each corresponding TEM image.

FIG. 19A is a plot of NBD fluorescence traces depicting lipid mixing kinetics between unsorted t-SNARE liposomes and unsorted or sorted v-SNARE liposomes with or without DNase I digestion, as indicated. DNase I digestion included incubation of liposomes in the presence of 1 U/10 µL DNase I at 37° C. for 2 hours. FIG. 19B shows NBD fluorescence after 2 hours of fusion reactions. FIGS. 4 and 18 provide mean diameters for liposomes in each fraction indicated in FIG. 19A or 19B.

FIG. 20A shows a TEM image of a homogeneous population of v-SNARE liposomes after sorting. The homogeneous population was fraction 16 having a mean diameter of 45 nm, as indicated. FIG. 20B shows TEM images of t-SNARE liposomes after being sorted into five homogeneous populations corresponding to fractions 4, 6, 8, 10, and 12, as indicated. FIG. 20C shows TEM images gathered after incubating the v-SNARE liposomes with the indicated t-SNARE liposome fraction for 2 hours at 4° C. (i.e., pre-incubation). The pre-incubation resulted in vesicle clusters, which is consistent with docking between the two proteoliposome species.

FIG. 21A depicts results from 3PS DNA brick-assisted sorting of liposomes having 0.4 µmol of total lipids and prepared by extrusion through 50-nm filters. Indicated fractions were analyzed by SDS-gel electrophoresis (top) and negative stain TEM (bottom). Fractions were numbered sequentially from F1 to F20 from top to bottom of a density gradient. Pseudo-color green depicts Cy5-labeled DNA and red depicts rhodamine-labeled lipid. FIG. 21B depicts size distribution of sorted liposomes in indicated fractions measured from negative-stain TEM images. Representative negative-stain TEM images for each indicated fraction are shown in the left panel of FIG. 21B. Histograms of liposome diameters in each indicated fraction are shown in the right panel of FIG. 21B. The histograms were fitted to Gaussian curves, as shown. Fitted means and standard deviations of liposome diameters and sample sizes (N) for indicated fractions are noted with the corresponding histograms. Scale bars shown in FIGS. 21A and 21B correspond to 200 nm.

DETAILED DESCRIPTION

Figure 1A:
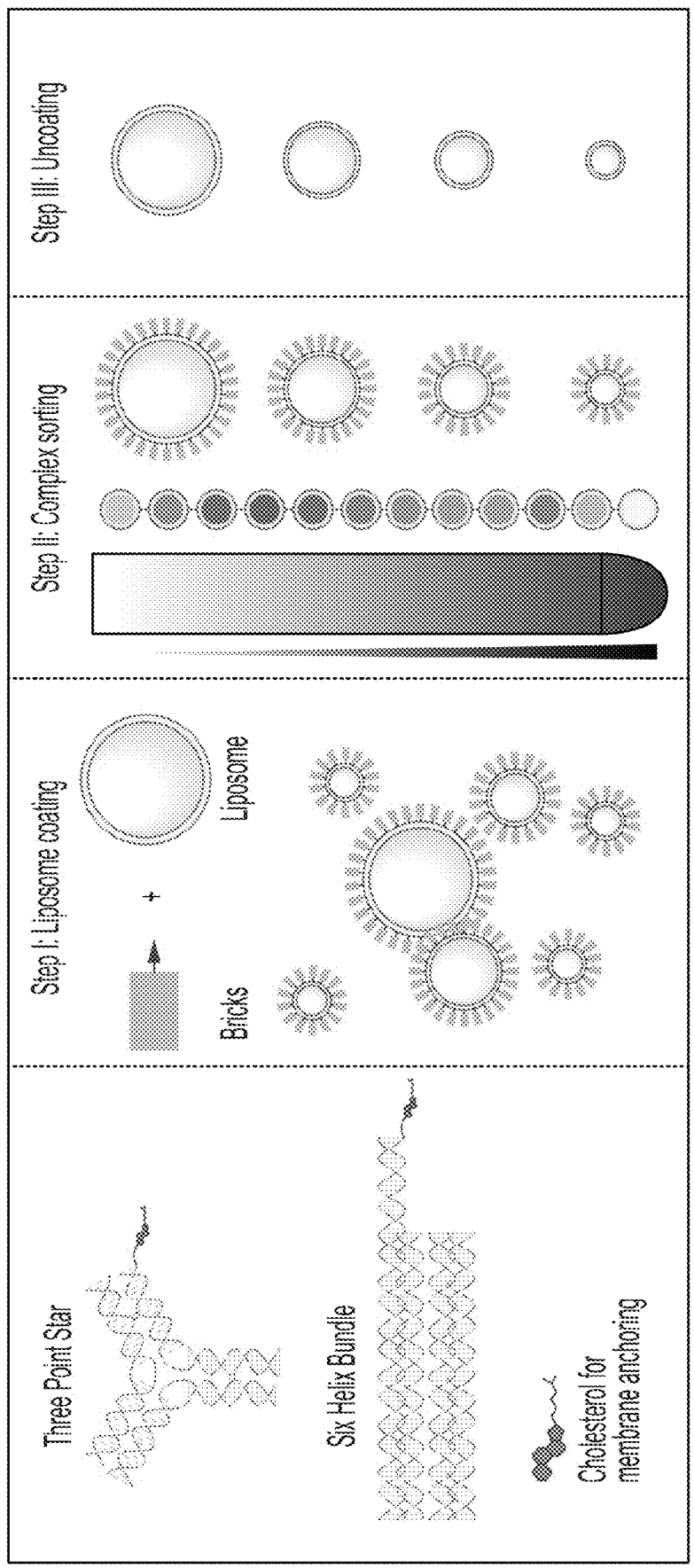
FIGS. 1A-1C show a DNA-brick-assisted liposome sorting scheme and the results.

The disclosure provides for improved methods for preparing uniform-sized liposomes. The methods described herein can be added to processes for preparing liposomes used for delivering drugs.

Unless defined otherwise, technical and scientific terms used herein have the same meaning as commonly understood by one of ordinary skill in the art to which this invention belongs.

The terms "a," "an," and "the" do not denote a limitation of quantity, but rather denote the presence of "at least one" of the referenced item.

The term "liposome" may be defined as a particle comprising lipids in a bilayer formation, which is usually a spherical bilayer formation. The term "liposome" encompasses both unilamellar liposomes and multilamellar liposomes.

The term "sorting agent" refers to a component that affects the ability of liposomes to be sorted. Various sorting agents are described throughout the application, for instance, "density-modifying moieties" that affect the density of liposomes so as to improve sensitivity of liposome separation by densitometric methods. "Nanobricks" are exemplary density-modified moieties that can comprise DNA oligonucleotides effective to differentiate liposomes of non-uniform size by their buoyant densities.

The term "targeting moiety" refers to agent that improves affinity for the sorting agent with the liposome. Exemplary targeting moieties can bind to both the sorting agent and to the liposome membrane so as to direct the targeting moiety to the liposome membrane.

The term "average diameter" as used herein, refers to a statistical determination of a liposomal population measured by the distance across the longest portion of the liposome (i.e., for example, the equator). For example, an average may be determined by summing a plurality of individual values and dividing by the number of values.

The term "uniform size" as used herein, refers to a specific liposome population having pre-determined average diameter range (i.e., for example, having a specific maximum average diameter and a specific minimum average diameter). Such uniform-sized liposome populations can be created by the methods described herein.

In one aspect is provided a method for producing uniform-size liposomes. A plurality of liposomes is coated with a sorting agent to yield a plurality of density-modified liposomes of different sizes. The density-modified liposomes of different sizes are separated using a densitometric method. In the method, the sorting agent comprises a density-modifying moiety and a targeting moiety.

The method of this aspect and the various embodiments described herein can provide for one or more of the following advantages: (i) excellent liposome size homogeneity, (ii) compatibility with a wide range of liposome sizes and membrane compositions, including those contain membrane proteins and nucleic acid cargos, (iii) scalability for production of large quantities of liposomes, a high recovery rate, exceeding 90%, 91%, 92%, 93%, 94%, 95%, 96%, 97%, 98%, or even a 99% lipid recovery rate, (iv) can be undertaken with standard biochemistry reagents and lab equipment, e.g., for use by a wide range of laboratories in academic and industrial settings, and (v) allowing for systematic analyses of curvature-dependent membrane biophysics and membrane-protein interactions.

In certain contexts, the methods described herein can provide for liposomes with a well-defined membrane curvature. Without wishing to be bound by theory, membrane curvature may be a critical factor in determining the kinetics of fusion, as well as the number of SNARE complexes required to mediate fusion. The method can allow for use of more than one or two sizes of liposomes may removing constraints in preparation of protein-reconstituted liposomes. The use of liposomes, e.g., proteoliposomes, with defined size distributions can allow for systematic studies of the curvature dependence of fusion rates.

In some embodiments, the density of the sorting agent is higher than the density of the liposome. In some embodiments, the density of an individual density-modified liposome is inversely related to the radius of the individual density-modified liposome. Without wishing to be bound by theory, for uncoated liposomes, particularly those not coated with the sorting agent, those liposomes with a smaller radius are less dense than those liposomes having a larger radius. The volume ratio of lipid membrane to lumen would be higher for a smaller liposome than for a larger liposome. Although typical lipid bilayers are lighter than aqueous solutions, liposomes that are different in size but identical in membrane and internal contents differ only slightly in buoyant density, because a liposome's aqueous lumen constitutes the bulk of its mass. However, the surface-area-to-volume ratio (S/V) of a spherical liposome decreases rapidly with increasing size (i.e. S/V is inversely proportional to radius), allowing for amplification of the buoyant density difference among liposomes by ubiquitously coating them with a dense material (analogous to attaching bricks to helium balloons). In theory, smaller liposomes may gain more density than larger ones when coated by such molecular bricks (see, FIG. 1B), allowing liposome separation by isopycnic centrifugation.

Because the sorting agent is of a higher density than the lipid membrane, and may be effective to even increase the density of the membrane component relative to the lumen, the volume ratio of coated lipid membrane to lumen can then be smaller for a smaller liposome than for a similarly-coated larger liposome. As described herein, various sorting agents can amplify the relationship between density and liposome size so as to improve sensitivity of coated liposomes to sorting processes, e.g., by densitometric sorting processes.

Various liposomes may be used. The liposomes can comprise membrane-bound proteins. The liposomes may comprise surface markers. In various embodiments, the liposomes comprise cargo, such as a drug or pharmaceutical agent. The methods described herein can be effective to sort liposomes with one or more of membrane-bound proteins, surface markers, and cargo. For example, the sorting agents described herein can bind to the lipid bilayer even in the presence of membrane-bound proteins, surface markers, and cargo.

In various embodiments, the density-modifying moiety comprises a polynucleotide. Various types of polynucleotides may be used, including DNA and RNA. Without wishing to be bound by theory, polynucleotides (e.g., DNA and RNA) can provide for any of the following advantages: excellent solubility, programmable self-assembly behaviors, and easiness to conjugate with hydrophobic molecules. Coating a liposome with DNA can also enhance liposome stability and may allow further functionalization. DNA coats can be advantageous because they may be inert to many biochemical reagents and can be readily removed by nucleases.

Sorting agents comprised of a few DNA oligonucleotides can be effective to sort or differentiate non-uniform sized (or hetero-sized) liposomes by their buoyant densities. After DNA-brick coating, milligram quantities of liposomes of different origins and modes of preparation (e.g. extrusion, sonication, and membrane-protein reconstitution) can be separated by centrifugation into six to eight homogeneous populations with mean diameters ranging, for example, from 30 to 130 nm.

Figure 21A:
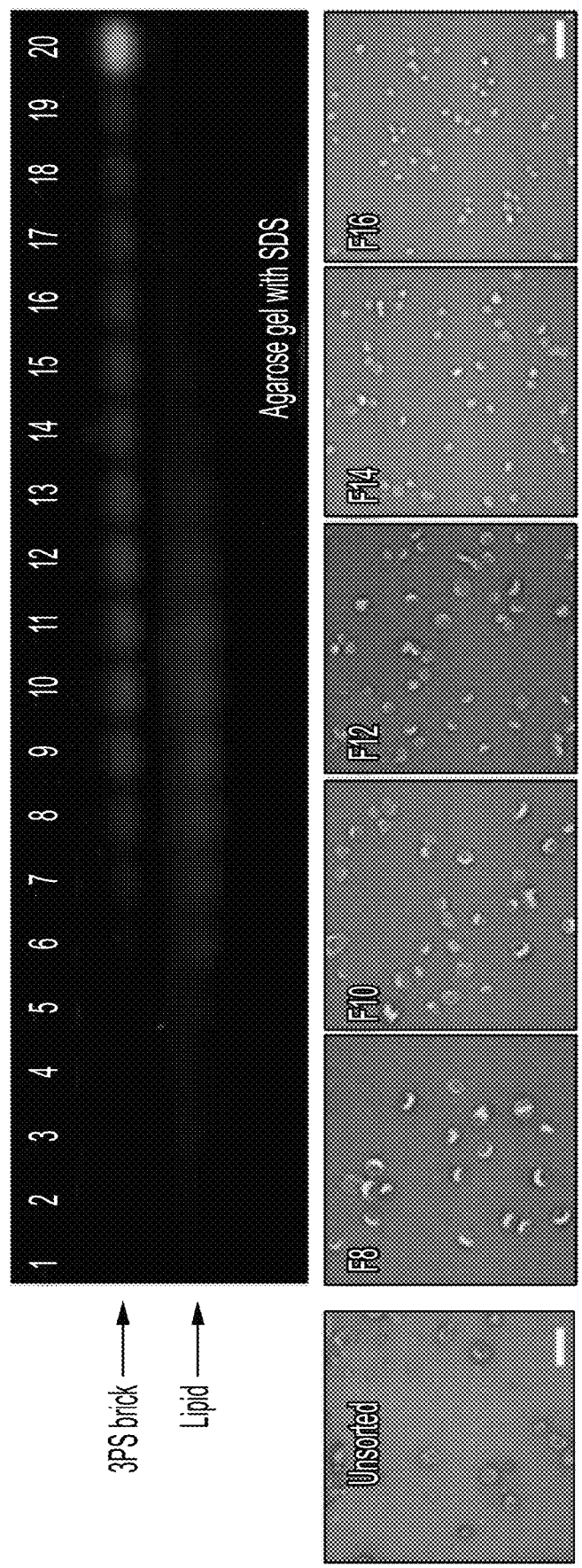
FIGS. 21A and 21B depict results obtained from a liposome sorting experiment.
Figure 21B:
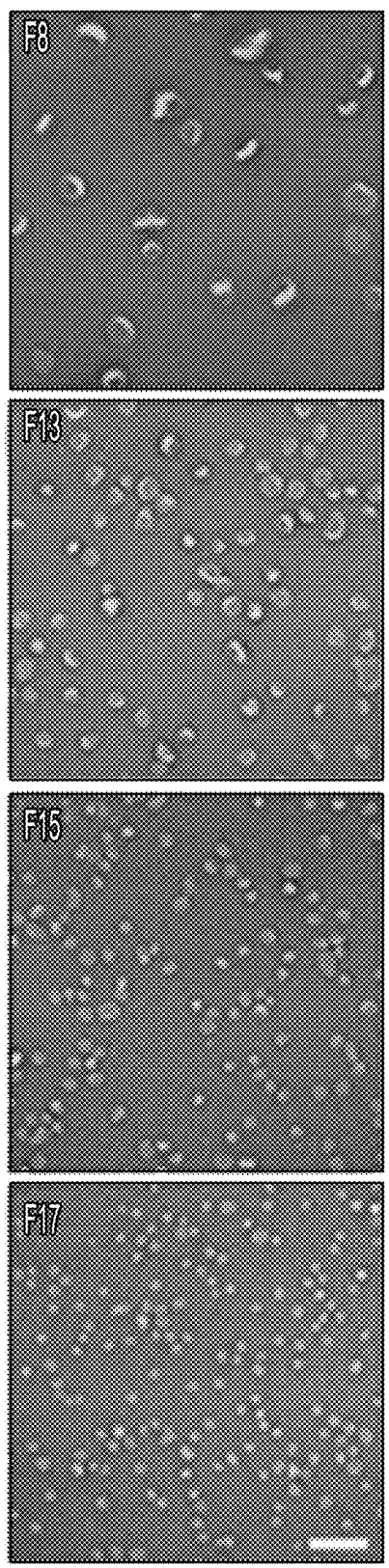
Figure 21B:
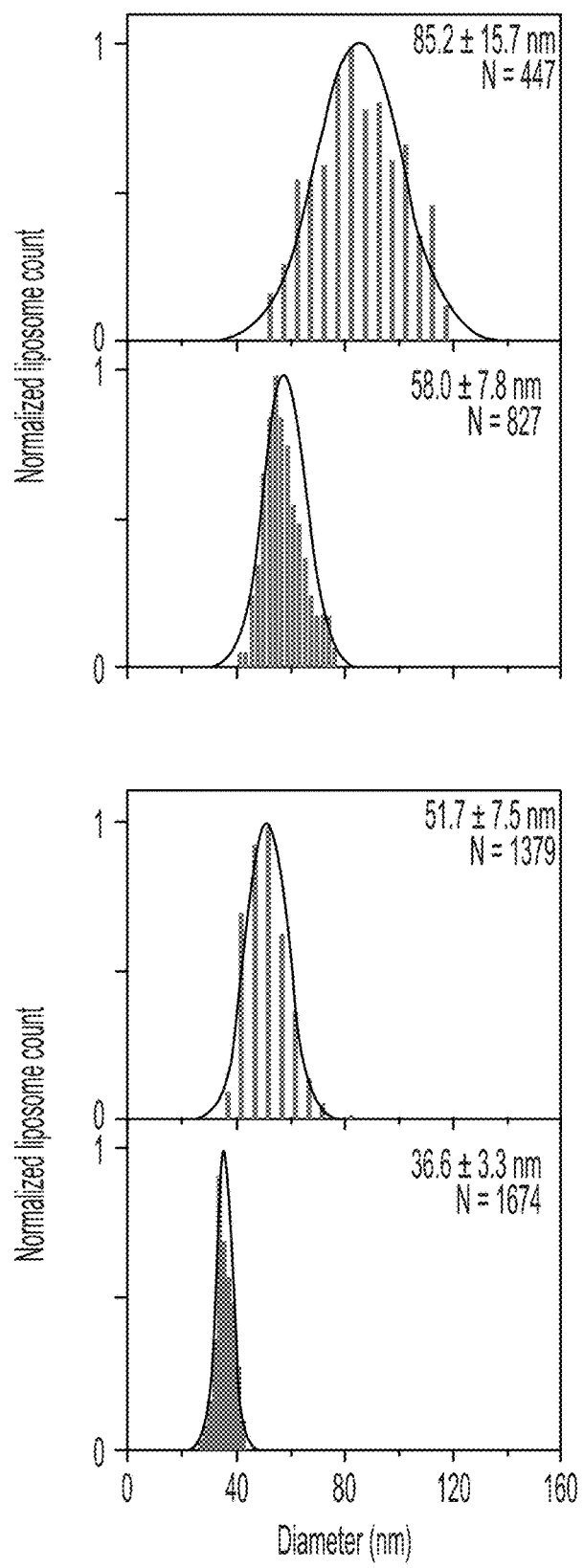

The liposome sorting methods described herein, e.g., those comprising DNA bricks, can further advance the membrane engineering capability of DNA nanotechnology. Specifically, the methods described herein can allow for separating liposomes from virtually any source into a range of narrowly distributed sizes with minimal impact on the original membrane properties. Further, two DNA structures composed of a handful of oligonucleotides can fulfill various sorting tasks. Without wishing to be bound by theory, the simplicity and robustness of the technique make it readily adaptable by any biochemical laboratory with access to research-grade ultracentrifuges (as shown by data described in FIG. 21). The generality of the methods described and exemplified herein may benefit from the programmability of nucleic acid nanostructures.

In certain embodiments, the polynucleotide is DNA. In various embodiments, the molecular mass of the density-modifying moiety is from 50 to 250 kDa. The molecular mass can be from 50 to 60 kDa, from 60 to 70 kDa, from 70 to 80 kDa, from 80 to 90 kDa, from 90 to 100 kDa, from 100 to 110 kDa, from 110 to 120 kDa, from 120 to 130 kDa, from 130 to 140 kDa, from 140 to 150 kDa, from 150 to 160 kDa, from 160 to 170 kDa, from 170 to 180 kDa, from 180 to 190 kDa, from 190 to 200 kDa, from 200 to 210 kDa, from 210 to 220 kDa, from 220 to 230 kDa, from 230 to 240 kDa, or from 240 to 250 kDa. The molecular mass can be from 50 to 100 kDa, 70 to 120 kDa, 90 to 140 kDa, 110 to 160 kDa, 130 to 180 kDa, or 150 to 200 kDa. Without wishing to be bound by theory, coating liposomes with nucleic acid (e.g., DNA and RNA) bricks of different molecular masses, sequences and shapes could facilitate the separation of liposomes within a broad size range.

The targeting moiety directs the density-modifying moiety to the liposome. Without wishing to be bound by theory, the targeting moiety can have high affinity for the lipid bilayer of the liposome in such a way that the targeting moiety can traffic the density-modifying moiety to the exterior surface of the lipid bilayer. For example, a cholesterol targeting moiety, that is covalently bound to the density-modifying moiety, can insert itself into the lipid bilayer as an anchor. A cholesterol targeting moiety can anchor the density-modifying moiety to the liposome. Other hydrophobic moieties or protein-specific ligands could enable sorting of vesicles bearing different surface markers. In addition to the utilities in basic research.

In various embodiments, the density-modifying moiety forms a three-point star structure. The three-point star structure can be formed by at least two different single stranded nucleotides. Three-point star structures are extensively described in He, Y. et al., "Hierarchical self-assembly of DNA into symmetric supramolecular polyhedral" Nature, 2008, 452(7184):198-201, which is incorporated by reference herein in its entirety. In some embodiments, the molecular mass of the three-point star structure is from 75 to 100 kDa. In some embodiments, the molecular mass of the three-point star structure is from 80 to 90 kDa. In some embodiments, the molecular mass of the three-point star structure is from 75 to 80 kDa, 77 to 82 kDa, 80 to 85 kDa, 82 to 87 kDa, 85 to 90 kDa, 87 to 92 kDa, 90 to 95 kDa, 92 to 97 kDa, or 95 to 100 kDa. In some embodiments, the molecular mass of the three-point star structure is 86 kDa.

Those having ordinary skill in the art appreciate that various nucleic acid sequences can be used to assemble a three-point star. The three point star may comprise one or more of the following nucleic acid sequences:

a sequence at least 85%, 87%, 90%, 92%, 95%, 97%, 98%, or 99% identical to AGGCATATTGAATCGTTTA-CAGGATTAGTAATTAACAGCTTTAATATCATCGCC-CATCGTAG GTTTCTTGCC (SEQ ID NO: 1);

the sequence of AGGCATATTGAATCGTTTACAG-GATTAGTAATTAACAGCTTTAATATCATCGCC-CATCGTAG GTTTCTTGCC (SEQ ID NO: 1);

a sequence at least 85%, 87%, 90%, 92%, 95%, 97%, 98%, or 99% identical to GACGACAGAGGTTGCTAGGCG (SEQ ID NO: 3);

the sequence of GACGACAGAGGTTGCTAGGCG (SEQ ID NO: 3);

a sequence at least 85%, 87%, 90%, 92%, 95%, 97%, 98%, or 99% identical to TTACCGTGTGTGTTAAGGTGG (SEQ ID NO: 4);

the sequence of TTACCGTGTGTGTTAAGGTGG (SEQ ID NO: 4);

a sequence at least 85%, 87%, 90%, 92%, 95%, 97%, 98%, or 99% identical to ACCGAGCCTCCGTCAA-CATCG (SEQ ID NO: 5);

the sequence of ACCGAGCCTCCGTCAACATCG (SEQ ID NO: 5);

a sequence at least 85%, 87%, 90%, 92%, 95%, 97%, 98%, or 99% identical to CCACCTTAACACGCGATGAT-ATTGCTGTTAATTAGGCTCGGT (SEQ ID NO: 6);

the sequence of CCACCTTAACACGCGATGATAT-TGCTGTTAATTAGGCTCGGT (SEQ ID NO: 6);

a sequence at least 85%, 87%, 90%, 92%, 95%, 97%, 98%, or 99% identical to CGATGTTGACGGACTAATCCTGTCGATT-CAATATCTGTCGTC (SEQ ID NO: 7);

the sequence of CGATGTTGACGGACTAATCCTGTC-GATTCAATATCTGTCGTC (SEQ ID NO: 7);

a sequence at least 85%, 87%, 90%, 92%, 95%, 97%, 98%, or 99% identical to CGCCTAGCAACCTGCCTGGCAAGCCTAC-GATGGACACGGTAA (SEQ ID NO: 8);

the sequence of CGCCTAGCAACCTGCCTGGCAAGCCTAC-GATGGACACGGTAA (SEQ ID NO: 8);

a sequence at least 85%, 87%, 90%, 92%, 95%, 97%, 98%, or 99% identical to CGCCTAGCAACCTGCCTGGCAAGCCTAC-GATGGACACGGTAA (SEQ ID NO: 8); or the sequence of CGCCTAGCAACCTGCCTGGCAAGCCTAC-GATGGACACGGTAA (SEQ ID NO: 8).

In various embodiments, the density-modifying moiety forms a six-helix bundle structure. The six-helix bundle structure can be formed by at least two different single stranded nucleotides. In some embodiments, the molecular mass of the six-helix bundle structure is from 150 to 250 kDa. In some embodiments, the molecular mass of the six-helix bundle structure is from 180 to 200 kDa. In some embodiments, the molecular mass of the six-helix bundle structure is from 150 to 160 kDa, 155 to 165 kDa, 160 to 170 kDa, 165 to 175 kDa, 170 to 180 kDa, 175 to 185 kDa, 180 to 190 kDa, 185 to 195 kDa, 190 to 200 kDa, 195 to 205 kDa, 200 to 210 kDa, 205 to 215 kDa, 210 to 220 kDa, 215 to 225 kDa, 220 to 230 kDa, 225 to 235 kDa, 230 to 240 kDa, 235 to 245 kDa, or 240 to 250 kDa. In some embodiments, the molecular mass of the six-helix bundle structure is 189 kDa.

Those having ordinary skill in the art appreciate that various nucleic acid sequences can be used to assemble a six-helix bundle. The six-helix bundle may comprise one or more of the following nucleic acid sequences:

a sequence at least 85%, 87%, 90%, 92%, 95%, 97%, 98%, or 99% identical to TTTAGTGCTACACTGTGCGTATGCGAAAACTTGCGATATGCTCCATTT (SEQ ID NO: 10);

the sequence of TTTAGTGCTACACTGTGCGTATGCGAAAACTTGCGATATGCTCCATTT (SEQ ID NO: 10);

a sequence at least 85%, 87%, 90%, 92%, 95%, 97%, 98%, or 99% identical to TTTAGTCGAGTGAACTGTAACGTACAGGTAGATAGACTCTGTATCTTT (SEQ ID NO: 11);

the sequence of TTTAGTCGAGTGAACTGTAACGTACAGGTAGATAGACTCTGTATCTTT (SEQ ID NO: 11);

a sequence at least 85%, 87%, 90%, 92%, 95%, 97%, 98%, or 99% identical to AAATTATCTACCACAACTCACCGCCTAGCAACCTGCCTGGCAAGCCTACGATGGACACGGT AA (SEQ ID NO: 12);

the sequence of AAATTATCTACCACAACTCACCGCCTAGCAACCTGCCTGGCAAGCCTACGATGGACACGGT AA (SEQ ID NO: 12);

a sequence at least 85%, 87%, 90%, 92%, 95%, 97%, 98%, or 99% identical to TTTATTCGAGCATGTCAGTGGATCAATCGTGTTAGACATGACGTATTT (SEQ ID NO: 13);

the sequence of TTTATTCGAGCATGTCAGTGGATCAATCGTGTTAGACATGACGTATTT (SEQ ID NO: 13);

a sequence at least 85%, 87%, 90%, 92%, 95%, 97%, 98%, or 99% identical to TTTGTGGACTATATATACGTGGAACCATGAATTGGCTGAGTTTGGTTT (SEQ ID NO: 14);

the sequence of TTTGTGGACTATATATACGTGGAACCATGAATTGGCTGAGTTTGGTTT (SEQ ID NO: 14);

a sequence at least 85%, 87%, 90%, 92%, 95%, 97%, 98%, or 99% identical to TTTTGGTTTACTCACTATTGTCACCTTATACCACAATCAGATCCGTTT (SEQ ID NO: 15);

the sequence of TTTTGGTTTACTCACTATTGTCACCTTATACCACAATCAGATCCGTTT (SEQ ID NO: 15);

a sequence at least 85%, 87%, 90%, 92%, 95%, 97%, 98%, or 99% identical to CAGTTCAGTCCATCTGACATGCTCGAATCCAAACTTAAACCA (SEQ ID NO: 17);

the sequence of CAGTTCAGTCCATCTGACATGCTCGAATCCAAACTTAAACCA (SEQ ID NO: 17);

a sequence at least 85%, 87%, 90%, 92%, 95%, 97%, 98%, or 99% identical to TTACCGTCTCGACTTGGAGCATATCGCATAGTGAGCAGCCAA (SEQ ID NO: 18);

the sequence of TTACCGTCTCGACTTGGAGCATATCGCATAGTGAGCAGCCAA (SEQ ID NO: 18);

a sequence at least 85%, 87%, 90%, 92%, 95%, 97%, 98%, or 99% identical to CACGATTTTCCACGGTATAAGGTGACAAAGTTTTCTACGTTA (SEQ ID NO: 19);

the sequence of CACGATTTTCCACGGTATAAGGTGACAAAGTTTTCTACGTTA (SEQ ID NO: 19);

a sequence at least 85%, 87%, 90%, 92%, 95%, 97%, 98%, or 99% identical to TTCATGGGATCCACGTAGGCTTGCCAGGCTACCTGGCATACG (SEQ ID NO: 21);

the sequence of TTCATGGGATCCACGTAGGCTTGCCAGGCTACCTGGCATACG (SEQ ID NO: 21);

a sequence at least 85%, 87%, 90%, 92%, 95%, 97%, 98%, or 99% identical to CGGATCTTAGCACTGATACAGAGTCTATCAGGTTGTGTCTAA (SEQ ID NO: 22);

the sequence of CGGATCTTAGCACTGATACAGAGTCTATCAGGTTGTGTCTAA (SEQ ID NO: 22);

a sequence at least 85%, 87%, 90%, 92%, 95%, 97%, 98%, or 99% identical to GTGAGTTGTGGTAGATAATTT (SEQ ID NO: 26); or the sequence of GTGAGTTGTGGTAGATAATTT (SEQ ID NO: 26).

The methods described herein can be used to experimentally model lipid biochemistry and membrane dynamics. Without wishing to be bound by theory, in cells the membranes are shaped into various curvatures that localize biochemical reactions and modulate membrane remodeling. Liposomes with a fine gradient of sizes can provide an ideal platform to study such curvature-dependent activities in vitro in a systematic and precise manner. Described herein is the use of liposome size sorting techniques to revamp two classical assays, which can show the benefit of using uniform-size liposomes for the experimental modeling of lipid biochemistry and membrane dynamics. For example, the membrane dynamics of synaptic vesicles in neurons can be investigated. Described herein is the use of minimal fusion machinery (SNAREs) to show that synaptic vesicle sizes are highly homogenous and regulated in neurons. The methods and platforms described herein can be used to model a wide variety of physiologically relevant events, such as where an array of proteins (e.g. Synaptogamin-1 or Munc18) govern the fate of vesicles. The methods described herein can allow for collection of curvature sensing information across the biologically relevant range of 25-60 nm where vesicles, tubules and the autophagic rim are found.

Various methods known in the art may be used to produce the liposomes described herein. The liposomes may be produced by extrusion. The liposomes may be produced by sonication. The liposomes may be produced by membrane-protein reconstitution. The liposomes may be produced by a combination of two or more of extrusion, sonication, and membrane-protein reconstitution.

In various embodiments, the liposomes are coated with sorting agent under conditions where the sorting agent is present in excess so as to coat the liposomes in a dense manner. The coating step may comprise coating the liposomes with the sorting agent at a ratio of liposomes to sorting agent of from 1:10 to 1:1000. The ratio of liposomes to sorting agent can be from 1:10 to 1:20, from 1:15 to 1:25, from 1:20 to 1:50, from 1:35 to 1:80, from 1:50 to 1:100, from 1:75 to 1:150, from 1:100 to 1:200, from 1:150 to 1:300, from 1:200 to 1:400, from 1:300 to 1:600, from 1:400 to 1:800, or from 1:500 to 1:1000. In various embodiments, the external surface of the liposomes is saturated with the sorting agent.

In various embodiments, the sorting agent comprises only one targeting moiety. The target moiety may be a hydrophobic molecule, e.g., a lipid or other molecule having affinity for the lipid bilayer. The lipid may be a cholesterol. The target moiety may be a protein-specific ligand. The targeting moiety may be an antibody or fragment thereof, e.g., scFv domain or Fab domain. The targeting moiety may be joined to the sorting agent with a spacer. In certain embodiments, the cholesterol is bound to a polynucleotide targeting moiety via a spacer. In other embodiments, the targeting moiety is bound to a polynucleotide targeting moiety via the 3' end of the polynucleotide. In other embodiments, the cholesterol is bound to a polynucleotide targeting moiety via the 3' end of the polynucleotide.

In various embodiments, the plurality of liposomes has an average diameter of greater than 100 nm. The average diameter may be greater than 120 nm, 140 nm, 160 nm, 180 nm, 200 nm, 220 nm, or 240 nm.

In various embodiments, the plurality of liposomes has an average diameter of less than 100 nm. The average diameter may be less than 95 nm, 90 nm, 85 nm, 80 nm, 75 nm, 70 nm, or 65 nm.

In various embodiments, the sorting agent has a buoyant density of from about 1.25 mg/mL to about 2 mg/mL in media comprising CsCl. Without wishing to be bound by theory, sorting agents with a buoyant density of about 1.25 mg/mL to about 2 mg/mL in media comprising CsCl are sufficiently dense so as to coat a population of liposomes such that the density of the coated liposomes is inversely related to the diameter of the liposomes. In certain embodiments, the sorting agent has a buoyant density of from 1.25 mg/mL to 2 mg/mL in media comprising CsCl. In certain embodiments, the sorting agent has a buoyant density of from 1.25 mg/mL to 1.35 mg/mL in media comprising CsCl. In certain embodiments, the sorting agent has a buoyant density of from 1.30 mg/mL to 1.40 mg/mL in media comprising CsCl. In certain embodiments, the sorting agent has a buoyant density of from 1.35 mg/mL to 1.45 mg/mL in media comprising CsCl. In certain embodiments, the sorting agent has a buoyant density of from 1.40 mg/mL to 1.50 mg/mL in media comprising CsCl. In certain embodiments, the sorting agent has a buoyant density of from 1.45 mg/mL to 1.55 mg/mL in media comprising CsCl. In certain embodiments, the sorting agent has a buoyant density of from 1.50 mg/mL to 1.60 mg/mL in media comprising CsCl. In certain embodiments, the sorting agent has a buoyant density of from 1.55 mg/mL to 1.65 mg/mL in media comprising CsCl. In certain embodiments, the sorting agent has a buoyant density of from 1.60 mg/mL to 1.70 mg/mL in media comprising CsCl. In certain embodiments, the sorting agent has a buoyant density of from 1.65 mg/mL to 1.75 mg/mL in media comprising CsCl. In certain embodiments, the sorting agent has a buoyant density of from 1.70 mg/mL to 1.80 mg/mL in media comprising CsCl. In certain embodiments, the sorting agent has a buoyant density of from 1.75 mg/mL to 1.85 mg/mL in media comprising CsCl. In certain embodiments, the sorting agent has a buoyant density of from 1.80 mg/mL to 1.90 mg/mL in media comprising CsCl. In certain embodiments, the sorting agent has a buoyant density of from 1.85 mg/mL to 1.95 mg/mL in media comprising CsCl. In certain embodiments, the sorting agent has a buoyant density of from 1.90 mg/mL to 2.00 mg/mL in media comprising CsCl.

The coated liposomes are then separated. After coating, the liposomes may exhibit a substantial degree of inverse relationship between density and liposome diameter. The degree of the inverse relationship can be at least 2 times, at least 2.5 times, at least 3 times, at least 3.5 times, or at least 4 times the degree of relationship between density and liposome diameter of the uncoated vesicles. Densitometric methods may then be employed to separate the coated liposomes into discrete populations. Various densitometric methods known in the art may be used. In various embodiments, isopycnic centrifugation is used to separate the coated liposomes into density fractions. The isopycnic centrifugation may be carried out using an iodixanol density gradient. The iodixanol density gradient may comprise an approximately linear gradient of iodixanol ranging from about 0 wt % iodixanol to about 30 wt % iodixanol. The iodixanol density gradient may comprise an approximately linear gradient of iodixanol ranging from 0 wt % iodixanol to 30 wt % iodixanol.

In various embodiments, the yield of liposomes recovered from the separating step is at least 80%. The yield of liposomes recovered from the separating step may be at least 81%. The yield of liposomes recovered from the separating step may be at least 82%. The yield of liposomes recovered from the separating step may be at least 83%. The yield of liposomes recovered from the separating step may be at least 84%. The yield of liposomes recovered from the separating step may be at least 85%. The yield of liposomes recovered from the separating step may be at least 86%. The yield of liposomes recovered from the separating step may be at least 87%. The yield of liposomes recovered from the separating step may be at least 88%. The yield of liposomes recovered from the separating step may be at least 89%. The yield of liposomes recovered from the separating step may be at least 90%. The yield of liposomes recovered from the separating step may be at least 91%. The yield of liposomes recovered from the separating step may be at least 92%. The yield of liposomes recovered from the separating step may be at least 93%. The yield of liposomes recovered from the separating step may be at least 94%. The yield of liposomes recovered from the separating step may be at least 95%.

In various embodiments, the method further comprises collecting one or more density-sorted fractions of the plurality of liposomes sorted using the densitometric method. The fraction collected may comprise uniform-size liposomes. The fraction collected may consist essentially of uniform-size liposomes. The fraction collected may consist of uniform-size liposomes. In various embodiments, the liposomes within each of the collected fractions have a coefficient of variation of less than 15%. The liposomes within each of the collected fractions may have a coefficient of variation of less than 14%. The liposomes within each of the collected fractions may have a coefficient of variation of less than 13%. The liposomes within each of the collected fractions may have a coefficient of variation of less than 12%. The liposomes within each of the collected fractions may have a coefficient of variation of less than 11%. The liposomes within each of the collected fractions may have a coefficient of variation of less than 10%. The liposomes within each of the collected fractions may have a coefficient of variation of less than 9%. The liposomes within each of the collected fractions may have a coefficient of variation of less than 8%. The liposomes within each of the collected fractions may have a coefficient of variation of less than 7%.

In various embodiments, the density-sorted fraction comprises liposomes having a mean diameter of less than 500 nm. The density-sorted fraction may comprise liposomes having a mean diameter of less than 480 nm. The density-sorted fraction may comprise liposomes having a mean diameter of less than 460 nm. The density-sorted fraction may comprise liposomes having a mean diameter of less than 440 nm. The density-sorted fraction may comprise liposomes having a mean diameter of less than 420 nm. The density-sorted fraction may comprise liposomes having a mean diameter of less than 400 nm. The density-sorted fraction may comprise liposomes having a mean diameter of less than 380 nm. The density-sorted fraction may comprise liposomes having a mean diameter of less than 360 nm. The density-sorted fraction may comprise liposomes having a mean diameter of less than 340 nm. The density-sorted fraction may comprise liposomes having a mean diameter of less than 320 nm.

In various embodiments, at least 90% of the liposomes have a diameter within about 83% to about 117% of the mean diameter of all of the liposomes present in the density-sorted fraction. At least 91%, 92%, 93%, 94%, or 95% of the liposomes may have a diameter within about 83% to about 117% of the mean diameter of all of the liposomes present in the density-sorted fraction. At least 90%, 91%, 92%, 93%, 94%, or 95% of the liposomes may have a diameter within 83% to 117% of the mean diameter of all of the liposomes present in the density-sorted fraction. At least 90%, 91%, 92%, 93%, 94%, or 95% of the liposomes may have a diameter within 84% to 116% of the mean diameter of all of the liposomes present in the density-sorted fraction. At least 90%, 91%, 92%, 93%, 94%, or 95% of the liposomes may have a diameter within 85% to 115% of the mean diameter of all of the liposomes present in the density-sorted fraction. At least 90%, 91%, 92%, 93%, 94%, or 95% of the liposomes may have a diameter within 86% to 114% of the mean diameter of all of the liposomes present in the density-sorted fraction. At least 90%, 91%, 92%, 93%, 94%, or 95% of the liposomes may have a diameter within 87% to 113% of the mean diameter of all of the liposomes present in the density-sorted fraction.

In certain embodiments, at least 90% of the liposomes have a diameter from 20 nm to 37 nm. In certain embodiments, at least 90% of the liposomes have a diameter from 22 nm to 39 nm. In certain embodiments, at least 90% of the liposomes have a diameter from 25 nm to 42 nm. In certain embodiments, at least 90% of the liposomes have a diameter from 27 nm to 49 nm. In certain embodiments, at least 90% of the liposomes have a diameter from 30 nm to 54 nm. In certain embodiments, at least 90% of the liposomes have a diameter from 32 nm to 57 nm. In certain embodiments, at least 90% of the liposomes have a diameter from 35 nm to 59 nm. In certain embodiments, at least 90% of the liposomes have a diameter from 37 nm to 61 nm. In certain embodiments, at least 90% of the liposomes have a diameter from 40 nm to 64 nm. In certain embodiments, at least 90% of the liposomes have a diameter from 43 nm to 66 nm. In certain embodiments, at least 90% of the liposomes have a diameter from 45 nm to 68 nm. In certain embodiments, at least 90% of the liposomes have a diameter from 47 nm to 70 nm. In certain embodiments, at least 90% of the liposomes have a diameter from 50 nm to 72 nm. In certain embodiments, at least 90% of the liposomes have a diameter from 53 nm to 75 nm. In certain embodiments, at least 90% of the liposomes have a diameter from 55 nm to 76 nm. In certain embodiments, at least 90% of the liposomes have a diameter from 57 nm to 78 nm. In certain embodiments, at least 90% of the liposomes have a diameter from 60 nm to 81 nm. In certain embodiments, at least 90% of the liposomes have a diameter from 62 nm to 82 nm. In certain embodiments, at least 90% of the liposomes have a diameter from 63 nm to 85 nm. In certain embodiments, at least 90% of the liposomes have a diameter from 65 nm to 88 nm. In certain embodiments, at least 90% of the liposomes have a diameter from 67 nm to 90 nm. In certain embodiments, at least 90% of the liposomes have a diameter from 70 nm to 94 nm. In certain embodiments, at least 90% of the liposomes have a diameter from 72 nm to 96 nm. In certain embodiments, at least 90% of the liposomes have a diameter from 75 nm to 99 nm. In certain embodiments, at least 90% of the liposomes have a diameter from 77 nm to 102 nm. In certain embodiments, at least 90% of the liposomes have a diameter from 80 nm to 108 nm. In certain embodiments, at least 90% of the liposomes have a diameter from 82 nm to 110 nm. In certain embodiments, at least 90% of the liposomes have a diameter from 86 nm to 113 nm. In certain embodiments, at least 90% of the liposomes have a diameter from 88 nm to 117 nm. In certain embodiments, at least 90% of the liposomes have a diameter from 90 nm to 121 nm. In certain embodiments, at least 90% of the liposomes have a diameter from 93 nm to 126 nm. In certain embodiments, at least 90% of the liposomes have a diameter from 97 nm to 128 nm. In certain embodiments, at least 90% of the liposomes have a diameter from 99 nm to 132 nm. In certain embodiments, at least 90% of the liposomes have a diameter from 102 nm to 137 nm. In certain embodiments, at least 90% of the liposomes have a diameter from 105 nm to 142 nm. In certain embodiments, at least 90% of the liposomes have a diameter from 107 nm to 146 nm. In certain embodiments, at least 90% of the liposomes have a diameter from 110 nm to 150 nm. In certain embodiments, at least 90% of the liposomes have a diameter from 115 nm to 155 nm. In certain embodiments, at least 90% of the liposomes have a diameter from 120 nm to 160 nm. In certain embodiments, at least 90% of the liposomes have a diameter from 125 nm to 165 nm. In certain embodiments, at least 90% of the liposomes have a diameter from 130 nm to 170 nm. In certain embodiments, at least 90% of the liposomes have a diameter from 135 nm to 180 nm. In certain embodiments, at least 90% of the liposomes have a diameter from 140 nm to 190 nm. In certain embodiments, at least 90% of the liposomes have a diameter from 150 nm to 200 nm. In certain embodiments, at least 90% of the liposomes have a diameter from 160 nm to 220 nm. In certain embodiments, at least 90% of the liposomes have a diameter from 170 nm to 240 nm. In certain embodiments, at least 90% of the liposomes have a diameter from 180 nm to 260 nm. In certain embodiments, at least 90% of the liposomes have a diameter from 190 nm to 280 nm. In certain embodiments, at least 90% of the liposomes have a diameter from 200 nm to 300 nm. In certain embodiments, at least 90% of the liposomes have a diameter from 225 nm to 350 nm. In certain embodiments, at least 90% of the liposomes have a diameter from 250 nm to 400 nm. In certain embodiments, at least 90% of the liposomes have a diameter from 275 nm to 450 nm. In certain embodiments, at least 90% of the liposomes have a diameter from 300 nm to 500 nm. In certain embodiments, at least 90% of the liposomes have a diameter from 325 nm to 550 nm. In certain embodiments, at least 90% of the liposomes have a diameter from 350 nm to 600 nm. In certain embodiments, at least 90% of the liposomes have a diameter from 375 nm to 650 nm. In certain embodiments, at least 90% of the liposomes have a diameter from 400 nm to 700 nm.

In certain embodiments, at least 90%, 91%, 92%, 93%, 94%, or 95% of the liposomes have a diameter from 20 nm to 37 nm, from 22 nm to 39 nm, from 25 nm to 42 nm, from 27 nm to 49 nm, from 30 nm to 54 nm, from 32 nm to 57 nm, from 35 nm to 59 nm, from 37 nm to 61 nm, from 40 nm to 64 nm, from 43 nm to 66 nm, from 45 nm to 68 nm, from 47 nm to 70 nm, from 50 nm to 72 nm, from 53 nm to 75 nm, from 55 nm to 76 nm, from 57 nm to 78 nm, from 60 nm to 81 nm, from 62 nm to 82 nm, from 63 nm to 85 nm, from 65 nm to 88 nm, from 67 nm to 90 nm, from 70 nm to 94 nm, from 72 nm to 96 nm, from 75 nm to 99 nm, from 77 nm to 102 nm, from 80 nm to 108 nm, from 82 nm to 110 nm, from 86 nm to 113 nm, from 88 nm to 117 nm, from 90 nm to 121 nm, from 93 nm to 126 nm, from 97 nm to 128 nm, from 99 nm to 132 nm, from 102 nm to 137 nm, from 105 nm to 142 nm, from 107 nm to 146 nm, from 110 nm to 150 nm, from 115 nm to 155 nm, from 120 nm to 160 nm, from 125 nm to 165 nm, from 130 nm to 170 nm, from 135 nm to 180 nm, from 140 nm to 190 nm, from 150 nm to 200 nm, from 160 nm to 220 nm, from 170 nm to 240 nm, from 180 nm to 260 nm, from 190 nm to 280 nm, from 200 nm to 300 nm, from 225 nm to 350 nm, from 250 nm to 400 nm, from 275 nm to 450 nm, from 300 nm to 500 nm, from 325 nm to 550 nm, from 350 nm to 600 nm, from 375 nm to 650 nm, or from 400 nm to 700 nm.

In various embodiments, the liposomes comprise one or more markers. The markers may enable visual detection of the liposomes, for example markers that comprise a dye molecule or a fluorophore. Exemplary markers include, but are not limited to, DOPC, DOPE, DOPS, rhodamine-DOPE, and NBD-PE. For example, the liposome may comprise from about 0 wt % to about 5 wt % rhodamine-DOPE. The liposome may comprise from about 0 wt % to about 5 wt % DOPC. The liposome may comprise from about 0 wt % to about 5 wt % DOPE. The liposome may comprise from about 0 wt % to about 5 wt % DOPS. The liposome may comprise from about 0 wt % to about 5 wt % NBD-PE.

The density-modifying moiety can be a polynucleotide, with the method further comprising separating the density-modifying moiety from the targeting moiety using a nuclease after the separating step. Various nucleases may be used, including DNase I. Restriction endonucleases may be used that are specific to a sequence at or near where the density-modifying moiety is fused to the targeting moiety.

Any of the liposomes described herein, including the coated and non-coated liposomes, may comprise a pharmaceutical agent. The pharmaceutical agent may be disposed within a lumen of the liposomes both before and after the separating step. Without wishing to be bound by theory, the density-modifying moiety and targeting moiety are not expected to substantially disrupt the lipid bilayer of the liposome. The amount of the pharmaceutical agent in the liposomes after the separating step may be at least 80%, 81%, 82%, 83%, 84%, 85%, 86%, 87%, 88%, 89%, 90%, 91%, 92%, 93%, 94%, 95%, 96%, 97%, 98%, or 99% of the amount of the pharmaceutical agent in the liposomes before the separating step. The method can further comprise removing or dissociating the targeting moiety from the liposomes after the separating step. For example, if the targeting moiety is cholesterol the cholesterol may be removed by contacting the coated liposomes with cyclodextrin. Removal of the targeting moiety, e.g., cholesterol, is optional. As another example, if the targeting moiety comprises a polynucleotide, then the targeting moiety may be removed by contacting the coated liposomes with a nuclease. As another example, if the targeting moiety comprises a polypeptide, then the targeting moiety is removed by contacting the coated liposomes with a protease.

The method may further comprise loading the obtained liposomes with a drug.

Also provided is a method for production of uniform-size liposomes, the method comprising:
coating a plurality of liposomes with cholesterol-modified oligonucleotides to yield a plurality of density-modified liposomes of different sizes,
separating the density-modified liposomes of different sizes by isopycnic centrifugation, and
isolating one or more fractions of uniform-size liposomes.

The cholesterol-modified oligonucleotides may comprise DNA, RNA, or a DNA/RNA hybrid structure. The cholesterol-modified DNA oligonucleotide may be in the form of a six-helix-bundle rod of about 189 kD with a single cholesterol at the end of each DNA structure. The size of the liposome may be greater than 100 nm. Alternatively, the cholesterol-modified DNA oligonucleotide may be in the form of a three-pointed star of about 86 kD with a single cholesterol at the end of each DNA structure. The size of the liposome may be less than 40 nm.

Also provided is a composition comprising density-sorted liposomes prepared according to any of the methods described above. The density-sorted liposomes may be substantially leak-free liposomes, for example the liposomes may retain at least 80%, 81%, 82%, 83%, 84%, 85%, 86%, 87%, 88%, 89%, 90%, 91%, 92%, 93%, 94%, 95%, 96%, 97%, 98%, or 99% of their cargo after preparation as compared to liposomes before preparation. In some embodiments, the density-sorted liposomes are leak-free liposomes. The density-sorted liposomes may be substantially impermeable to various materials, including fluorescein and a divalent cation, such as zinc.

Also provided is a sorting agent comprising a density-modifying moiety and a targeting moiety, wherein the density-modifying moiety is a nucleotide-brick. In some embodiments, the density-modifying moiety comprises a polynucleotide. The targeting moiety may be bound to a nucleic acid within the polynucleotide, a 5' end of the polynucleotide, or a 3' end of the polynucleotide. The polynucleotide may be DNA or RNA. In certain embodiments, the polynucleotide is DNA. In certain embodiments, the polynucleotide is RNA.

In some embodiments, the molecular mass of the density-modifying moiety is from 50 to 250 kDa. The molecular mass can be from 50 to 60 kDa, from 60 to 70 kDa, from 70 to 80 kDa, from 80 to 90 kDa, from 90 to 100 kDa, from 100 to 110 kDa, from 110 to 120 kDa, from 120 to 130 kDa, from 130 to 140 kDa, from 140 to 150 kDa, from 150 to 160 kDa, from 160 to 170 kDa, from 170 to 180 kDa, from 180 to 190 kDa, from 190 to 200 kDa, from 200 to 210 kDa, from 210 to 220 kDa, from 220 to 230 kDa, from 230 to 240 kDa, or from 240 to 250 kDa. The molecular mass can be from 50 to 100 kDa, 70 to 120 kDa, 90 to 140 kDa, 110 to 160 kDa, 130 to 180 kDa, or 150 to 200 kDa. In various embodiments, the density-modifying moiety forms a three-point star structure. In some embodiments, the molecular mass of the three-point star structure is from 75 to 100 kDa. In some embodiments, the molecular mass of the three-point star structure is from 80 to 90 kDa. In some embodiments, the molecular mass of the three-point star structure is 86 kDa.

Various nucleotide sequences may be used to assemble the three point star. In some embodiments, the density-modifying moiety comprises a sequence at least 85% identical to: AGGCATATTGAATCGTTTACAGGATT- AGTAATTAACAGCTTTAATATCATCGCCCATCGTAG GTTTCTTGCC (SEQ ID NO: 1). In some embodiments, the density-modifying moiety comprises a sequence at least 85% identical to GACGACAGAGGTTGCTAGGCG (SEQ ID NO: 3). In some embodiments, the density-modifying moiety comprises a sequence at least 85% identical to TTACCGTGTGTGTTAAGGTGG (SEQ ID NO: 4). In some embodiments, the density-modifying moiety comprises a sequence at least 85% identical to ACCGAGCCTCCGTCAACATCG (SEQ ID NO: 5). In some embodiments, the density-modifying moiety comprises a sequence at least 85% identical to CCACCTTAACACGCGATGATATTGCTGTTAATTAGGCTCGGT (SEQ ID NO: 6). In some embodiments, the density-modifying moiety comprises a sequence at least 85% identical to CGATGTTGACGGACTAATCCTGTCGATTCAATATCTGTCGTC (SEQ ID NO: 7). In some embodiments, the density-modifying moiety comprises a sequence at least 85% identical to CGCCTAGCAACCTGCCTGGCAAGCCTACGATGGACACGGTAA (SEQ ID NO: 8). In some embodiments, the density-modifying moiety comprises a sequence at least 85% identical to CGCCTAGCAACCTGCCTGGCAAGCCTACGATGGACACGGTAA (SEQ ID NO: 8).

In some embodiments, the density-modifying moiety forms a six-helix bundle structure. In some embodiments, the molecular mass of the six-helix bundle structure is from 150 to 250 kDa. In some embodiments, the molecular mass of the six-helix bundle structure is from 180 to 200 kDa. In certain embodiments, the molecular mass of the six-helix bundle structure is 189 kDa. In some embodiments, the density-modifying moiety comprises a sequence at least 85% identical to TTTAGTGCTA-CACTGTGCGTATGCGAAAACTTGCGATATGCTC-CATTT (SEQ ID NO: 10). In some embodiments, the density-modifying moiety comprises a sequence at least 85% identical to TTTAGTCGAGTGAACTGTAACGTA-CAGGTAGATAGACTCTGTATCTTT (SEQ ID NO: 11). In some embodiments, the density-modifying moiety comprises a sequence at least 85% identical to AAATTATC-TACCACAACTCACCGCCTAGCAACCTGCCTGGCAA GCCTACGATGGACACGGT AA (SEQ ID NO: 12). In some embodiments, the density-modifying moiety comprises a sequence at least 85% identical to TTTATTCGAG-CATGTCAGTGGATCAATCGTGTTAGACATGACGT-ATTT (SEQ ID NO: 13). In some embodiments, the density-modifying moiety comprises a sequence at least 85% identical to TTTGTGGACTATATATACGTGGAACCAT-GAATTGGCTGAGTTTGGTTT (SEQ ID NO: 14). In some embodiments, the density-modifying moiety comprises a sequence at least 85% identical to TTTTGGTTTACTCAC-TATTGTCACCTTATACCACAATCAGATCCGTTT (SEQ ID NO: 15). In some embodiments, the density-modifying moiety comprises a sequence at least 85% identical to CAGTTCAGTCCATCTGACATGCTCGAATCCAAACT-TAAACCA (SEQ ID NO: 17). In some embodiments, the density-modifying moiety comprises a sequence at least 85% identical to TTACCGTCTCGACTTGGAG-CATATCGCATAGTGAGCAGCCAA (SEQ ID NO: 18). In some embodiments, the density-modifying moiety comprises a sequence at least 85% identical to CACGATTTTC-CACGGTATAAGGTGACAAAGTTTTCTACGTTA (SEQ ID NO: 19). In some embodiments, the density-modifying moiety comprises a sequence at least 85% identical to TTCATGGGATCCACGTAGGCTTGCCAGGC-TACCTGGCATACG (SEQ ID NO: 21). In some embodiments, the density-modifying moiety comprises a sequence at least 85% identical to CGGATCTTAGCACTGATA-CAGAGTCTATCAGGTTGTGTCTAA (SEQ ID NO: 22). In some embodiments, the density-modifying moiety comprises a sequence at least 85% identical to GTGAGTTGTGGTAGATAATTT (SEQ ID NO: 26).

In some embodiments, the sorting agent comprises only one targeting moiety. The targeting moiety may comprise a hydrophobic molecule, such as a lipid (e.g., cholesterol). The cholesterol may be any number of modified forms of cholesterol. The lipid can comprise a fusion of one or more different lipid molecules.

In some embodiments, the targeting moiety comprises a spacer, where the cholesterol is bound to the targeting moiety via the spacer, and where the spacer comprises triethylene glycol. In some embodiments, the targeting moiety comprises an antibody or protein-specific ligand. In certain embodiments, the sorting agent has a buoyant density of from about 1.25 g/mL to about 2 g/mL.

In some embodiments, the sorting agent comprises an oligonucleotide labeled with a dye or a fluorophore. In some embodiments, the dye or fluorophore is Cy5.

In another aspect is provided a method of stabilizing a liposome comprising contacting the liposome with any of the above sorting agents to yield a stabilized liposome.

The stabilized liposome may be substantially stable for at least three months at room temperature. The stabilized liposome may be substantially stable for at least twenty weeks at room temperature. The stabilized liposome may be substantially stable for at least six months at room temperature. The stabilized liposome can have substantially the same monodispersity after three months as compared to immediately after the stabilized liposome is prepared. The stabilized liposome can have substantially the same monodispersity after twenty weeks as compared to immediately after the stabilized liposome is prepared. The stabilized liposome can have substantially the same monodispersity after six months as compared to immediately after the stabilized liposome is prepared. The stabilized liposome can have substantially the same intact liposomal boundaries after three months as compared to immediately after the stabilized liposome is prepared. The stabilized liposome can have substantially the same intact liposomal boundaries after twenty weeks as compared to immediately after the stabilized liposome is prepared. The stabilized liposome can have substantially the same intact liposomal boundaries after six months as compared to immediately after the stabilized liposome is prepared.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Materials and Methods

The following materials and methods were used, unless described otherwise in a specific Example.

Figure 5A:
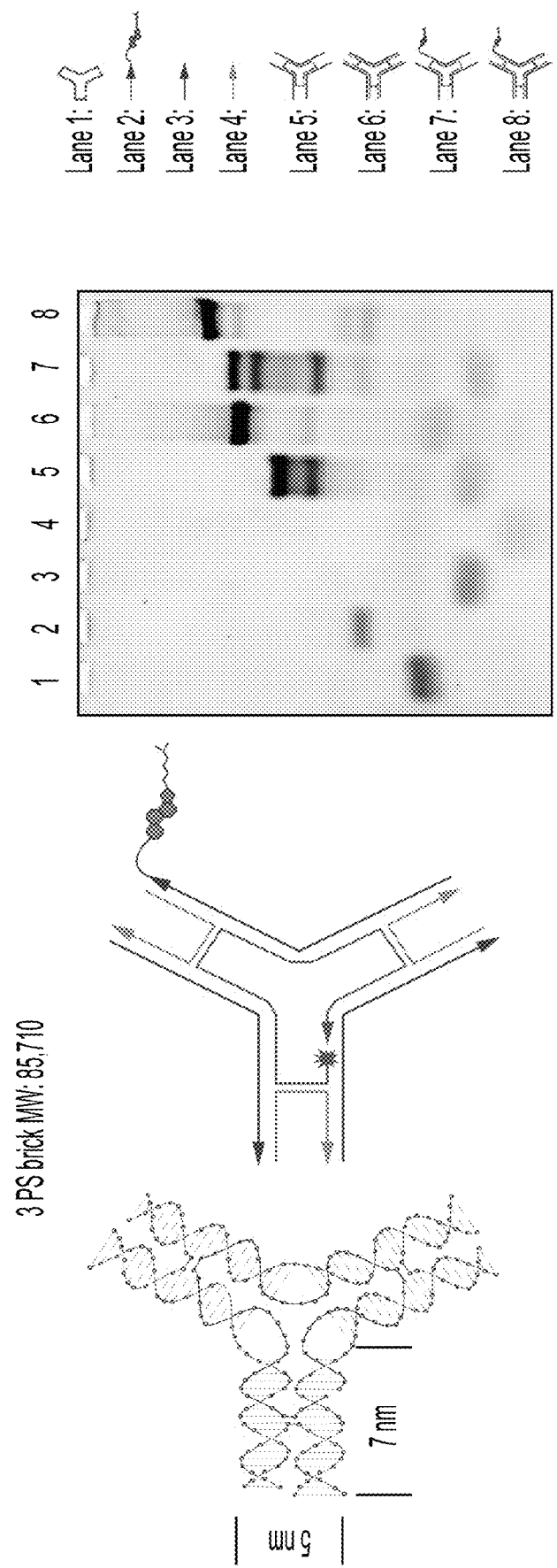
FIGS. 5A and 5B depict design diagrams (left of each figure) and PAGE results prepared for 3-point star (3PS), see right panel of FIG. 5A, and 6 Helix Bundle (6HB), see right panel of FIG. 5B, DNA bricks, and components or partial constructs thereof. The PAGE conditions were 6% gel run at 15 V/cm for 70 min.
Figure 5B:
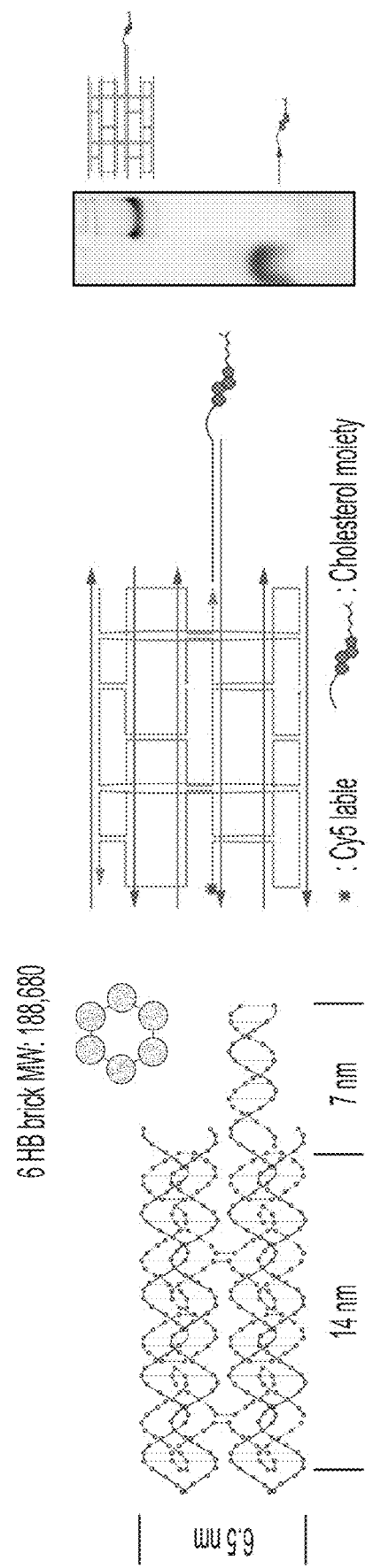

DNA and lipid materials. DNA oligonucleotides (oligos) were synthesized by Integrated DNA Technologies. Chemically modified oligos were purified via HPLC by manufacturer, while unmodified oligos were purified via PAGE in house, see Table 1 for oligo sequences. DNA brick designs are shown in FIGS. 5A and 5B, along with the PAGE analyses of the assembly products.

TABLE 1

DNA strand sequences

| SEQ ID NO: | Name | Sequence |
|---|---|---|
| | | 3 Point Star Brick (3PS bricks) |
| 1 | C | AGGCATATTGAATCGTTTACAGGATTAG TAATTAACAGCTTTAATATCATCGCCCA TCGTAGGTTTCTTGCC |
| 2 | C-Cy5 | /5Cy5/AGGCATATTGAATCGTTTACAGGA TTAGTAATTAACAGCTTTAATATCATCG CCCATCGTAGGTTTCTTGCC |
| 3 | S-a | GACGACAGAGGTTGCTAGGCG |
| 4 | S-b | TTACCGTGTGTGTTAAGGTGG |
| 5 | S-c | ACCGAGCCTCCGTCAACATCG |
| 6 | E-a | CCACCTTAACACGCGATGATATTGCTGTT AATTAGGCTCGGT |
| 7 | E-b | CGATGTTGACGGACTAATCCTGTCGATTC AATATCTGTCGTC |
| 8 | E-0 | CGCCTAGCAACCTGCCTGGCAAGCCTACG ATGGACACGGTAA |
| 9 | E-Chol | CGCCTAGCAACCTGCCTGGCAAGCCTACG ATGGACACGGTAA/3CholTEG/ |
| | | 6 Helix Bundle Brick (6HB bricks) |
| 10 | 6hb-M0 | TTTAGTGCTACACTGTGCGTATGCGAAAA CTTGCGATATGCTCCATTT |
| 11 | 6hb-M1 | TTTAGTCGAGTGAACTGTAACGTACAGGT AGATAGACTCTGTATCTTT |

TABLE 1-continued

DNA strand sequences

| SEQ ID NO: | Name | Sequence |
|---|---|---|
| 12 | 6hb-M2 | AAATTATCTACCACAACTCACCGCCTAGC AACCTGCCTGGCAAGCCTACGATGGACAC GGTAA |
| 13 | 6hb-M3 | TTTATTCGAGCATGTCAGTGGATCAATCGT GTTAGACATGACGTATTT |
| 14 | 6hb-M4 | TTTGTGGACTATATATACGTGGAACCATGA ATTGGCTGAGTTTGGTTT |
| 15 | 6hb-M5 | TTTTGGTTTACTCACTATTGTCACCTTATAC CACAATCAGATCCGTTT |
| 16 | 6hb-S0 | CACAGTGGATTGTGTATATATAGTCCACTA CGTCACTAGGCG |
| 17 | 6hb-S1 | CAGTTCAGTCCATCTGACATGCTCGAATCC AAACTTAAACCA |
| 18 | 6hb-S2 | TTACCGTCTCGACTTGGAGCATATCGCATA GTGAGCAGCCAA |
| 19 | 6hb-S3 | CACGATTTTCCACGGTATAAGGTGACAAAG TTTTCTACGTTA |
| 20 | 6hb-S3-Cy5 | /5Cy5/CACGATTTTCCACGGTATAAGGTGAC AAAGTTTTCTACGTTA |
| 21 | 6hb-S4 | TTCATGGGATCCACGTAGGCTTGCCAGGCT ACCTGGCATACG |
| 22 | 6hb-S5 | CGGATCTTAGCACTGATACAGAGTCTATCA GGTTGTGTCTAA |
| 23 | M2'-Chol | GTGAGTTGTGGTAGATAATTT/3CholTEG/ Deoxyribozyme |
| 24 | I-R1a-FAM | /56FAM/CATGTACAGCCATAGTTGAGCATTA AGTTGAAGTGGCTGTACATG |

All lipids were purchased from Avanti Polar Lipids. For general sorting experiments, leakage assay, and lipidation assay, liposomes were prepared in Buffer X. For proteoliposome fusion study, SNARE proteins were reconstituted into liposomes in Buffer Y. To avoid osmolality shock, DNA bricks were prepared in the same buffer (X or Y) as the liposomes, see below. Lipid and buffer compositions are listed in Table 2.

TABLE 2

Lipid compositions and buffer ingredients. Numeric values refer to molar percentages and ratios. Composition B is used in the Examples unless noted otherwise.

| Abbreviation | Full name of lipids |
|---|---|
| DOPC | 1,2-dioleoyl-sn-glycero-3-phosphocholine |
| DOPE | 1,2-dioleoyl-sn-glycero-3-phosphoethanolamine |
| DOPS | 1,2-dioleoyl-sn-glycero-3-phospho-L-serine |
| DOTAP | 1,2-dioleoyl-3-trimethylammonium-propane |
| PEG-2k-DOPE | 1,2-dioleoyl-sn-glycero-3-phosphoethanolamine-N-[methoxy(polyethylene glycol)-2000] |
| rhodamine-DOPE | 1,2-dioleoyl-sn-glycero-3-phosphoethanolamine-N-(lissamine rhodamine B sulfonyl) |
| NBD-PE | 1,2-dioleoyl-sn-glycero-3-phosphoethanolamine-N-(7-nitro-2-1,3-benzoxadiazol-4-yl) |

| | DOPC | DOPE | DOPS | DOTAP | PEG-2k-DOPE | rhodamine-DOPE |
|---|---|---|---|---|---|---|
| Composition A | 99.2% | 0% | 0% | 0% | 0% | 0.8% |
| Composition B | 59.2% | 30% | 10% | 0% | 0% | 0.8% |
| Composition C | 59.2% | 30% | 0% | 10% | 0% | 0.8% |
| Composition D | 94.2% | 0% | 0% | 0% | 5% | 0.8% |

| | POPC | DOPS | rhodamine-DOPE | NBD-PE | v-SNARE:lipid |
|---|---|---|---|---|---|
| v-SNARE liposome | 82% | 15% | 1.5% | 1.5% | 1:200 or 1:400 |
| | POPC | DOPS | POPE | PIP2 | t-SNARE:lipid |
| t-SNARE liposome | 58% | 25% | 15% | 2% | 1:400 |

TABLE 2-continued

Lipid compositions and buffer ingredients. Numeric values refer to molar percentages and ratios. Composition B is used in the Examples unless noted otherwise.

|  | HEPES | KCl | MgCl$_2$ | pH |
|---|---|---|---|---|
| Buffer X | 25 mM | 400 mM | 10 mM | 7.0 |
| Buffer Y | 25 mM | 140 mM | 0 mM | 7.0 |

The liposomes were prepared as follows. Solvent evaporation and lipid rehydration was undertaken. To prepare 1 mL of liposomes containing 3 μmol total lipid (final $C_{lipid}$=3 mM) of a certain composition, see Table 2, appropriate volumes of lipid stocks (dissolved in chloroform) were mixed in a round-bottom glass tube. The mixture was blown-dried under N2 for at least ½ hour. The resulting lipid film at the tube bottom was further dried overnight in a desiccator under vacuum. To rehydrate the lipids, 1 mL of Buffer X, see Table 2, was added into the tube and agitated for ½ hour. To prepare for the leakage assay, 1 mL of 1 μM FAM-modified I-R1a deoxyribozyme dissolved in Buffer X was used instead for rehydration. The glass tubes were wrapped with aluminum foil to reduce photobleaching of fluorescent labels.

Sequential extrusion was undertaken to produce liposome with nominal diameters of 50-200 nm. The rehydrated lipid suspension was transferred into a 1.5 mL centrifuge tube and thermo-cycled between a liquid-nitrogen bath and a 37° C.-water bath 5-10 times. The frozen-thawed suspension was then sequentially extruded through polycarbonate filters of nominal pore sizes of 400 nm, 200 nm and 50 nm, each time using a Mini Extruder (Avanti Polar Lipids) following manufacture's recommendations. The extruded liposomes after passing through 200-nm and 50-nm filters (typically 300 μL each) were store at 4° C.; the remaining 400 μL of liposomes were sonicated as described below.

Sonication was undertaken to produce liposome with nominal diameters<50 nm. Extruded liposomes (~400 μL) were sonicated using a Qsonica Q125 dip-probe sonicator for 1 min (10 cycles of 1-s on, 1-s off) while sitting on ice-water bath.

DNA brick preparation and assembly were undertaken as follows. PAGE or HPLC purified oligos were dissolved in deionized, Milli-Q water (Millipore) with concentrations normalized to 120 μM each. To assemble the 3PS (comprises either SEQ ID NOs:1 and 3-9, or alternatively, SEQ ID NOs: 2-9) and 6HB (comprises either SEQ ID NOs:10-19 and 21-23, or alternatively, SEQ ID NOs: 10-18 and 20-23) DNA bricks, various amount of cholesterol-modified oligos (1-2.5 μM) and stoichiometric amount of unmodified oligos (1 μM each) were mixed in in Buffer X and underwent thermal annealing from 95 to 4° C. (held at 95, 65, 50, 42, 37, 22, and 4° C. for 5 min each). The assembly products were electrophoresed in a non-denaturing 6% polyacrylamide gel under 15V/cm for 70 min in 1×TAE, 10 mM MgCl$_2$. The optimal molar ratio between modified and unmodified oligos, which gave rise to a sharp, distinct band after Sybr Gold staining, was chosen for DNA brick assembly for the rest of this study. In addition, 10% of an unmodified oligo (SEQ ID NO:1 in 3PS and SEQ ID NO:19 in 6HB, Table 1) was replaced with a Cy5-labeled oligo (SEQ IDs NOs: 2 and 20) for staining-free visualization of DNA bricks on gels.

Purification and characterization of DNA bricks was undertaken as follows. Large scale (400 μL of 5 μM) DNA-brick assemblies were placed on top of a 5%-20% glycerol gradient in a 5-mL ultracentrifugation tube (Beckman Coulter, Cat #344057). The sample-loaded density medium was spun at 55,000 rpm and room temperature (RT) for 4.5 hours in a SW55-Ti rotor (Beckman Coulter) before fractionated into 200-μL fractions. Five microliter of each fraction was electrophoresed in a 3.5% agarose gel containing 0.05% ethidium bromide under 10 V/cm for 1.5 hr in 0.5×TBE, 10 mM MgCl$_2$, see FIG. 6. Fractions containing well-formed bricks (e.g. fractions 8-10 in FIG. 6) were combined and concentrated to 50-100 μL by centrifugation (10 min at 10,000 rcf) on Amicon filtration units (Millipore) with 10 kD nominal molecular weight limit (NMWL). The concentrated sample was diluted in Buffer X or Y to 500 μL and concentrated again for a total of four times. The DNA brick concentration was determined by OD$_{260}$ measurement of a NanoDrop spectrometer (Thermo Fisher Scientific). The purified bricks were diluted to 5 μM in Buffer X or Y and stored at −20° C.

DNA brick-assisted liposome sorting and liposome coating were performed as follows. For small scale sorting, 40 μL of purified 3PS or 6HB brick (cholesterol-labeled, 1 μM) and 5 μL of liposome (3 mM lipid) were mixed in a 200 μL tube and incubate at room temperature for 1-2 hr under continuous agitation. The brick:lipid ratio of 1:375 was empirically determined to be sufficient for subsequent liposome sorting (below). In case of suboptimal sorting, a higher concentration of DNA brick may be used for liposome coating. When sorting larger quantities of liposomes, the amount of DNA brick and liposome was increased proportionally; the DNA brick concentration may be adjusted as appropriate. Table 3 provides some guidelines. For example, our largest scale preparation started with >1 mg liposome (1.8 μmole total lipid), which was split into six 5-mL ultracentrifuge tubes after DNA-coating for isopycnic centrifugation (below).

TABLE 3

The amount of reagents used for different scale of sorting experiments.

| Scale | Brick amount | Lipid amount | Total volume | Volume loaded to iodixanol gradient |
|---|---|---|---|---|
| 1× | 40 pmol | 15 nmol | 45 μL | 45 μL + 45 μL 45% iodixanol |
| 10× | 400 pmol | 150 nmol | 350 μL | 350 μL + 350 μL 45% iodixanol |
| 20× | 800 pmol | 300 nmol | 350 μL | 350 μL + 350 μL 45% iodixanol |

Liposome sorting by centrifugation was performed as follows. Iodixanol density gradient was prepared from stock solutions of 45%, 18%, 15%, 12%, 9%, 6%, 3% and 0% (v/v) iodixanol (Stemcell Technologies) in Buffer X.

DNA-coated liposomes were mixed with equal volume of 45% iodixanol, forming a 22.5% iodixanol solution at the bottom of an ultracentrifugation tube. For the small-scale separation (1× in Table 3), 80 μL of such solution was pipetted into an 800-μL tube (Beckman Coulter Cat #344090). Seven additional iodixanol layers (18% to 0%, 80 μL each) were carefully placed on top of one another to form a quasi-linear gradient. The tube, loaded with liposome sample in the iodixanol gradient, was spun in a SW55-Ti rotor at 48,000 rpm and RT for 4.5 hr. For large scale preparations (e.g. 10× and 20× in Table S3), linear 0-18% iodixanol gradients (4.2 mL each) were formed in 5-mL tubes (Beckman Coulter, Cat #344057) using a Gradient Master (BioComp Instruments). 700 µL of DNA-coated liposomes in 22.5% iodixanol were carefully layered at the bottom of the gradient using a syringe and a needle. The tubes were spun at 50,000 rpm and RT for 4.5 hours. Proteoliposomes (see FIG. 18), were sorted in the same way, except using gradients made in Buffer Y.

Figure 14A:
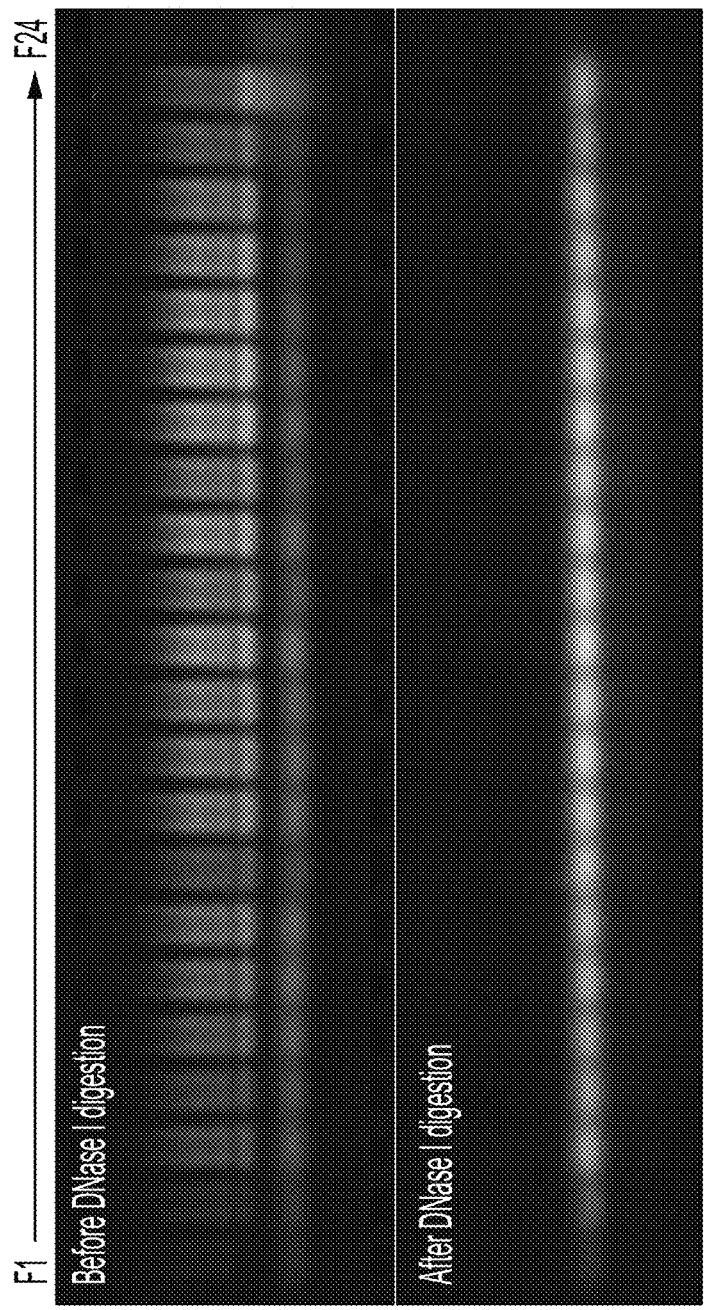
FIGS. 14A and 14B depict results from experiments wherein DNA bricks were enzymatically removed from sorted liposomes.
Figure 14B:
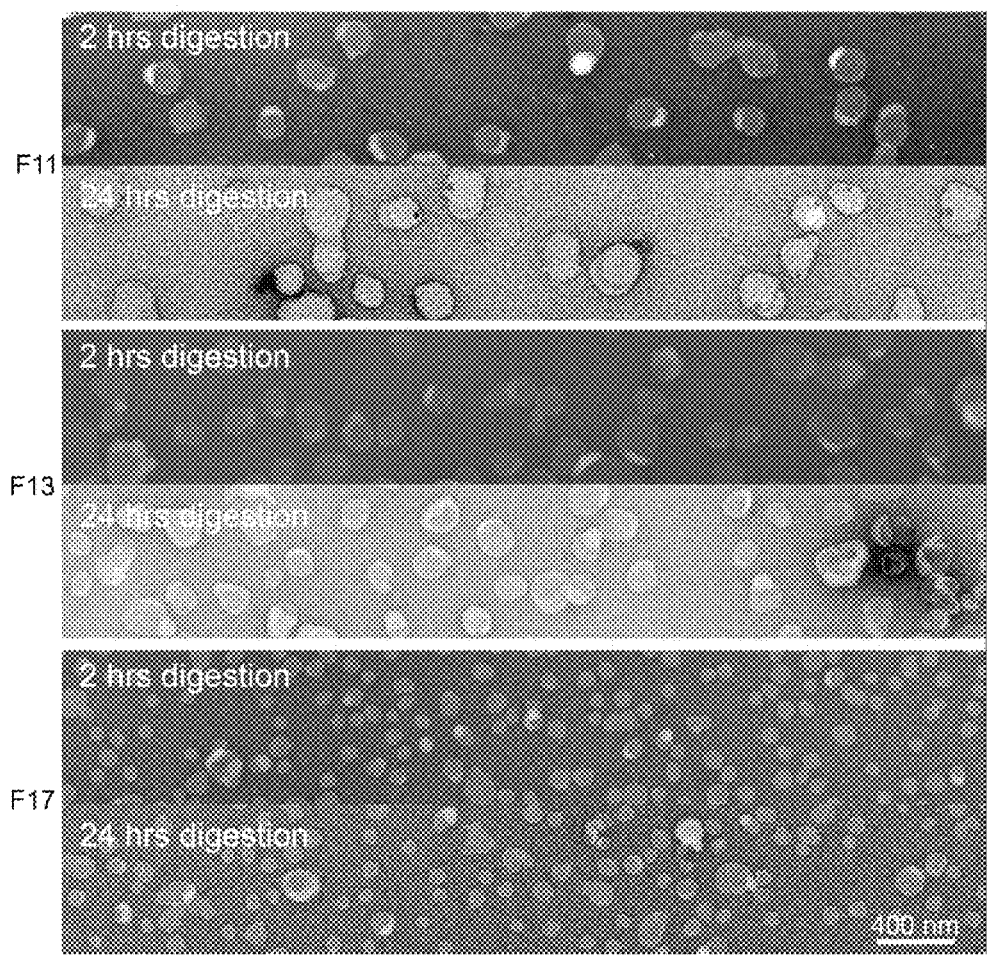

Post-centrifugation recovery was performed as follows. After ultracentrifugation, the content of a tube was collected from top to bottom with 52 µL (800 µL tube) or 200 µL (5 mL tube) per fraction. Caution was used to minimize disturbance to the gradient when pipetting. The recovered fractions were transferred to a 96-well plate, sealed with aluminum film, and stored at RT in the dark. To remove iodixanol and concentrate sorted liposomes, selected fractions were combined and concentrated to 50-100 µL by centrifugation (8 min at 10,000 rcf) on Amicon filtration units with 30 kD NMWL. The concentrated liposomes were diluted in Buffer X or Y to 500 µL and concentrated again for a total of 4-5 times. Optionally, sorted liposomes were treated with DNase I (Thermo Fisher Scientific) following manufacturer's recommendation to remove DNA bricks, see FIG. 14.

Characterization of sorted liposomes was performed by agarose gel electrophoresis. Recovered fractions of a post-centrifugation gradient (5 µL each) were electrophoresed in a 3.5% agarose gel (casted with 0.05% sodium dodecyl sulfate, SDS) at 10 V/cm for 1.5 hr in a 0.5×TBE buffer containing 10 mM MgCl2 and 0.05% SDS.

Figure 8:
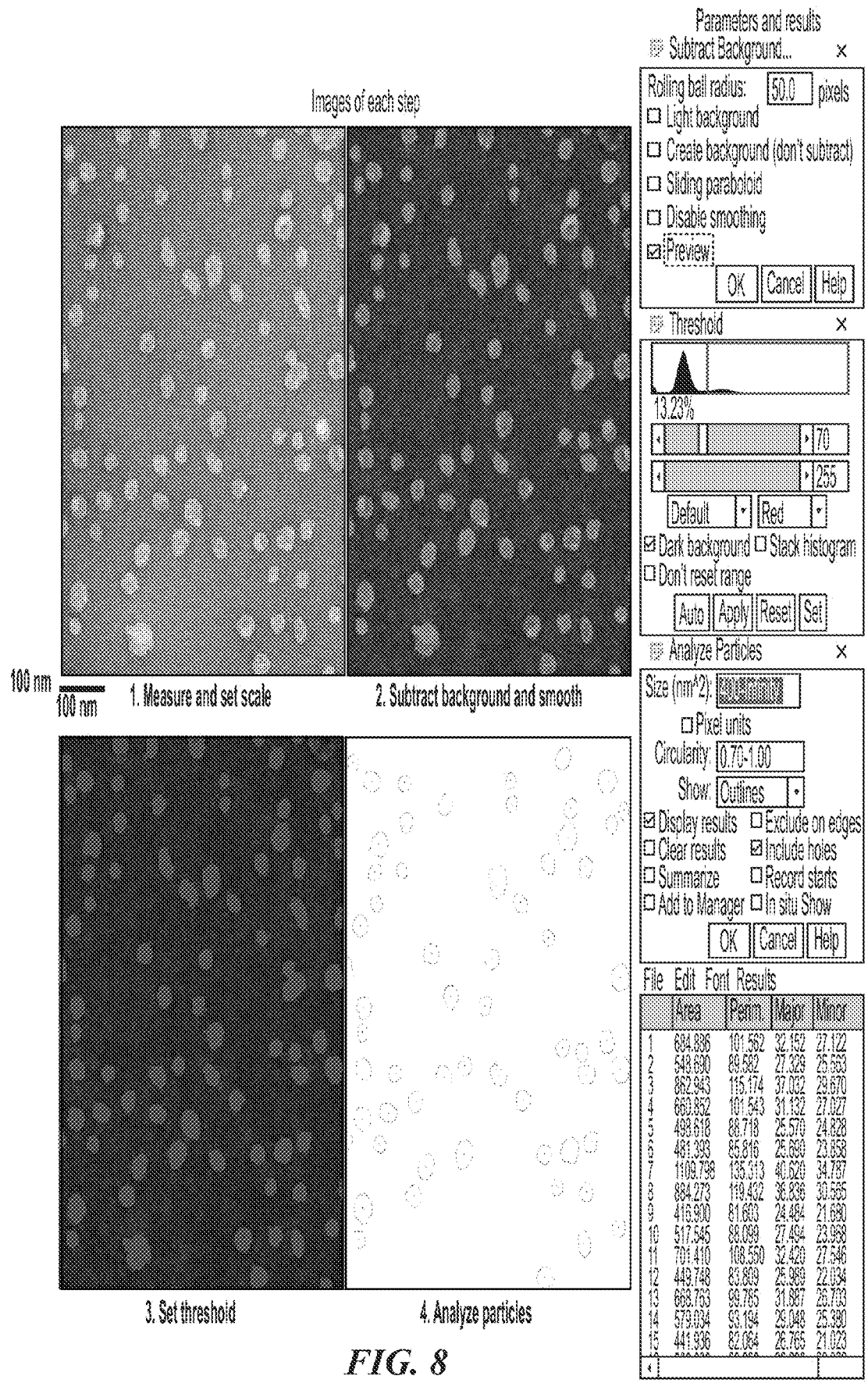
FIG. 8 provides an overview of a TEM image analysis pipeline used to determine diameters of sorted liposomes using built-in functions of ImageJ. Steps of the pipeline included: 1) Set scale by measuring the length of a scale bar, see top left image; 2) Subtract background using a rolling ball radius of from about 50 to about 150 depending upon original contrast and smooth the image 10× for contrast enhancement and noise reduction, see top middle image; 3) Set threshold at an appropriate value to highlight all liposomes (holes inside were acceptable), see bottom left image; 4) Run particle analysis with settings of (A) circularity higher than 0.7, (B) show outlines, (C) include holes, and (D) display results as listed, see lower middle image. Parameter setups are illustrated in the rightmost image. Liposome dimeters were calculated based on measured area (A) using the equation $D=2\times\sqrt{A/\pi}$.

A negative stain TEM study was performed as follows. A drop of sample (~5 µL) was deposited on a glow discharged formvar/carbon coated copper grid (Electron Microscopy Sciences), incubated for 1-3 minute and blotted away. The grid was then washed briefly and stained for 1 minute with 2% (w/v) uranyl formate. Images were acquired on a JEOL JEM-1400 Plus microscope (acceleration voltage: 80 kV) with a bottom-mount 4 k×3 k CCD camera (Advanced Microscopy Technologies). The liposome sizes were measured from electron micrographs by ImageJ (National Institutes of Health). The image analysis workflow is summarized in FIG. 8.

Cryo EM imaging was performed as follows. A drop (3.5 µL) of liposome sample was loaded onto a glow-discharged lacey carbon film, copper, 300 mesh grids and plunge frozen in liquid ethane using an FEI Mark III Vitrobot operating at 100% humidity, 22° C. temperature, 5 s blot time and −4 force.

The grids were imaged on an FEI Talos L1200 TEM equipped with a Ceta CCD camera. The images were collected at magnification of 36K/45K/57K/92K (with the pixel size of 4.01/3.21/2.53/1.57 Å) and a dose of 50 e/Å$^2$, using a defocus range of −2 to −4 µm.

A leakage assay (deoxyribozyme self-cleavage) was performed as follows. As described above, deoxyribozyme I-R1a (with 5'-FAM label) (SEQ ID NO: 24) in Buffer X was first loaded into liposomes through a rehydration process. After sequential extrusions (see above), the liposomes were coated with 6HB bricks and sorted as described above. Fractions from density ultracentrifugation, as well as a control sample containing unsorted liposomes (free I-R1a pre-removal through a separate isopycnic centrifugation without DNA-brick coating), were normalized to 0.75 mM lipid concentration. A deoxyribozyme reaction buffer (DRB+) was prepared to contain 25 mM HEPES, 400 mM KCl, 6 mM MgCl$_2$ and 4 mM ZnCl$_2$, which provides the same osmotic pressure as Buffer X but with 2 mM Zn$^{2+}$ for I-R1a cleavage once mixed with the sample in 1:1 ratio.

Three microliters of Buffer X containing 0% (for permeability test) or 14% n-octyl-β-D-glucopyranoside (OG, for liposome lysis) was added to 9 µL of each sample (fraction 6, 8, 10, 12, 14, 16, 18, and unsorted), then mixed with 12 µL DRB+ and incubated at 37° C. for 12 hr. After incubation, samples were mixed with 16 µL denaturing loading buffer (90% formamide, 10 mM NaOH, 1 mM EDTA, 0.1% Xylene Cyanole FF) and boiled for 3 min. Samples (10 µL each) were electrophoresed in a 12% urea polyacrylamide gel containing 0.1% SDS in 1×TBE buffer with 0.1% SDS at 10 V/cm for 1.5 hours (FIG. 2).

An ATG7/ATG3 catalyzed GL1 lipidation assay was performed as follows. The assay involved a lipidation reaction. Protein expression and membrane-curvature dependent lipidation reactions were performed as described previously [35-37]. Purified ATG7 (1.5 µM), ATG3 (2.5 µM) and human GABARAP L1 (GL1, 8 µM) were mixed with unsorted or sorted liposomes (composition B, 1 mM total lipid) in the presence of 1 mM dithiothreitol (DTT) and 1 mM ATP in SNH buffer (50 mM Tris at pH 8, 100 mM NaCl and 1 mM MgCl$_2$) and incubated at 30° C. for 90 min. The reaction was stopped by 4×SDS-PAGE loading buffer and boiled at 90° C. for 5 min. Electrophoresis was performed in precast 10% Bis-Tris gels (Novex, Thermo Fisher Scientific) running in 1×MES SDS Running Buffer (NuPAGE, Thermo Fisher Scientific) at 180 V (18V/cm) for 60 min. The proteins were visualized with Coomassie blue stain following manufacturer instructions (Imperial Protein Stain, Thermo Fisher Scientific).

Figure 12A:
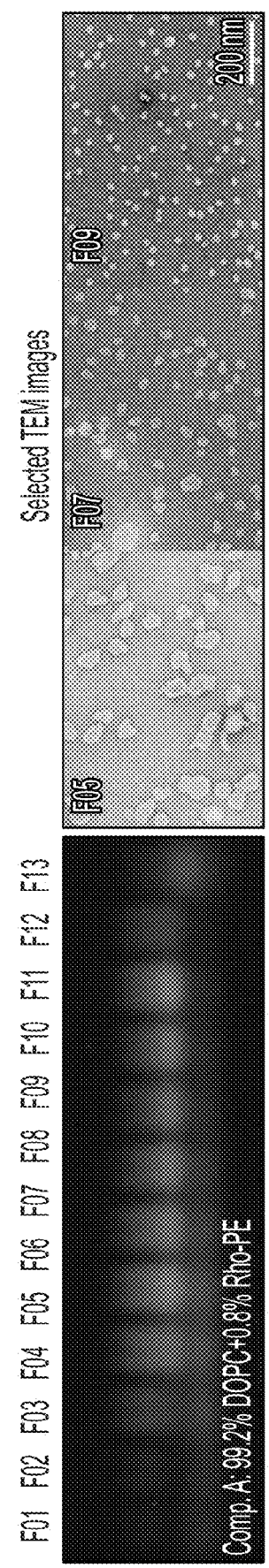
FIGS. 12A-12C depict results obtained from DNA-brick assisted sorting of liposomes of different lipid compositions.
Figure 12B:
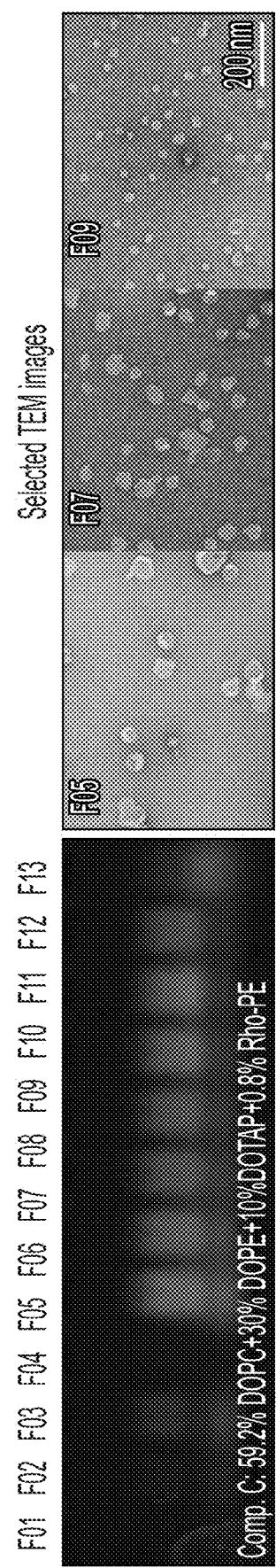
Figure 12C:
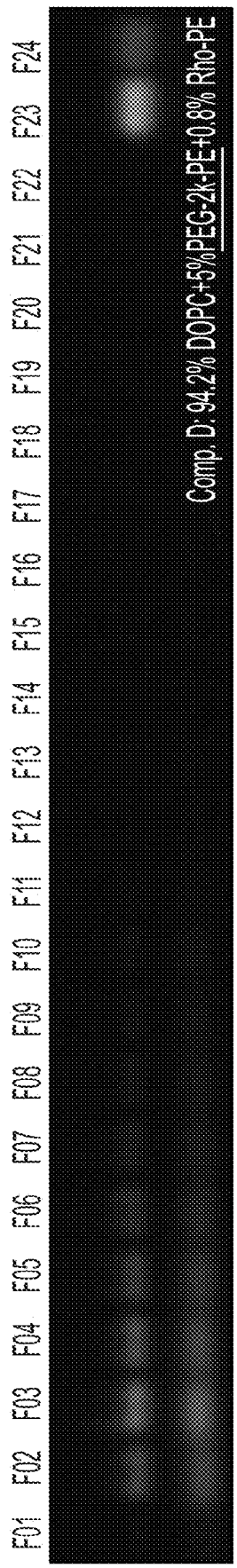

Immunoblotting was performed. After electrophoresis, samples were transferred onto a PVDF membrane (Amersham, GE Healthcare), blocked with 5% BSA and probed with anti-GL1 (1:1000, Cell Signaling Technology clone D5R9Y) antibody (Sigma) in 2.5% BSA. HRP-conjugated anti-mouse (NA931) and anti-rabbit (NA934) secondary antibodies were purchased from Amersham, GE Healthcare. See FIGS. 3 and 12 for results.

A SNARE-mediated liposome fusion assay was performed as follows. Plasmid constructs were prepared, followed by protein purification. The vectors encoding full-length t-SNARE complex including rat Stx1A and mouse 6×His-SNAP25 (plasmid pTW34) and 6×His-SUMO-VAMP2 (plasmid pET-SUMO-VAMP2) were transfected into the BL21-Gold (DE3) *E. coli* strain (Agilent Technologies; Cat #230132) and purified as previously described [38]. Briefly, bacteria carrying SNARE plasmids were cultured in 2 L LB media at 37° C. until OD$_{600}$ reached 0.7, induced by 1 mM isopropyl β-D-thiogalactoside, and cultured for additional 3 hr at 37° C. The pelleted cells were resuspended in breaking buffer (25 mM HEPES pH 7.4, 400 mM KCl, 10% glycerol, 4% Triton X-100, 1 mM TCEP, protease cocktail inhibitors) and lysed by cell disruptor (Avestin) with 3-5 passages at ~15,000 psi. The cell lysate was clarified by centrifugation at 40,000 rpm for 30 min; the supernatant was collected and incubated with nickel-NTA agarose (Qiagen) for 4 hr to overnight at 4° C. t-SNARE bound beads were rinsed with 25 mM HEPES pH 7.4, 400 mM KCl, 10% glycerol, 1% (w/v) OG, 1 mM TCEP. t-SNARE proteins were eluted off the beads by elution buffer (25 mM HEPES pH 7.4, 400 mM KCl, 10% glycerol, 1% OG, 1 mM TCEP, 400 mM imidazole). 6×His-SUMO tags ("6×His" disclosed as SEQ ID NO: 25) on VAMP2 were cleaved by SUMO protease.

Proteoliposome preparation was performed as follows. SNARE proteins were reconstituted into liposomes at physiologically relevant densities, with protein:lipid ratio at 1:200 or 1:400 for v-SNARE liposome and at 1:400 for t-SNARE liposomes. A vacuum-dried lipid film was dissolved in the reconstitution buffer (25 mM HEPES pH 7.4, 140 mM KCl, 0.2 mM TCEP, 10% glycerol, 1% OG) and mixed with SNARE proteins. OG-free reconstitution buffer was added to reach a final OG concentration of 0.33%. Detergent was then removed in Slide-A-Lyzer dialysis cassettes (Thermo Fisher Scientific) against 4 L of OG-free reconstitution buffer at 4° C. overnight. Proteoliposomes were separated in a Nycodenz (Progen Biotechnik) density gradient via centrifugation. For t-SNARE liposomes, centrifugation was done in a SW60-Ti rotor (Beckman Coulter) at 55,000 rpm for 3 hr 40 min at 4° C.; for v-SNARE liposomes, centrifugation was done in a SW55-Ti rotor (Beckman Coulter) at 48,000 rpm for 4 hr at 4° C. These proteoliposomes were sorted as described in Methods 3 and analyzed by negative-stain TEM (Method 4b) and SDS-PAGE, see FIG. 18. The v-SNARE concentrations of proteoliposomes were determined using VAMP2 concentration standards by densitometry (ImageJ). Lipid concentrations of v-SNARE liposomes were determined by rhodamine absorbance at 574 nm.

A lipid mixing assay was performed as follows. A typical fusion reaction happened between 5 µL of v-SNARE liposome labeled with a pair of FRET dyes (donor: NBD-DOPE, acceptor: Rhodamine-DOPE) and 45 µL of unlabeled t-SNARE liposome [39], see Table 2, with a total lipid concentration of 3 mM. These 50 µL mixtures were pre-incubated at 4° C. for 2 hr for trans-SNARE complex assembly, before being transferred to a Falcon 96-well plate with black skirt and clear flat bottom and heated to 37° C. NBD fluorescence was monitored at emission/excitation of ~535/460 nm every 1 min for 2 hr by Synergy H1 Hybrid Multi-Mode Reader (BioTek Instruments). At the end of the 2-hr reaction, 10 µL of 20% Triton X-100 was added and fluorescence was recorded for another 30 min to obtain the maximum fluorescence.

Figure 1B:
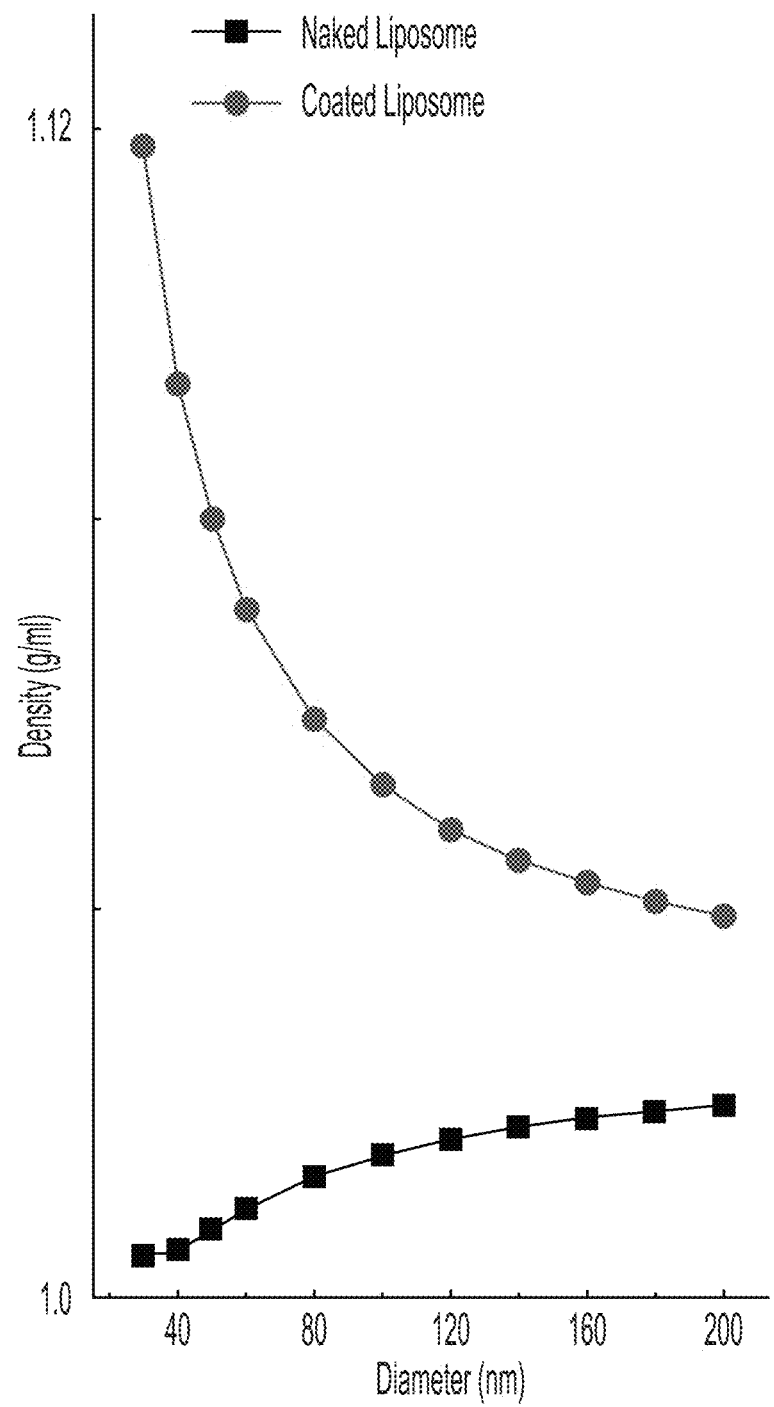
Figure 6:
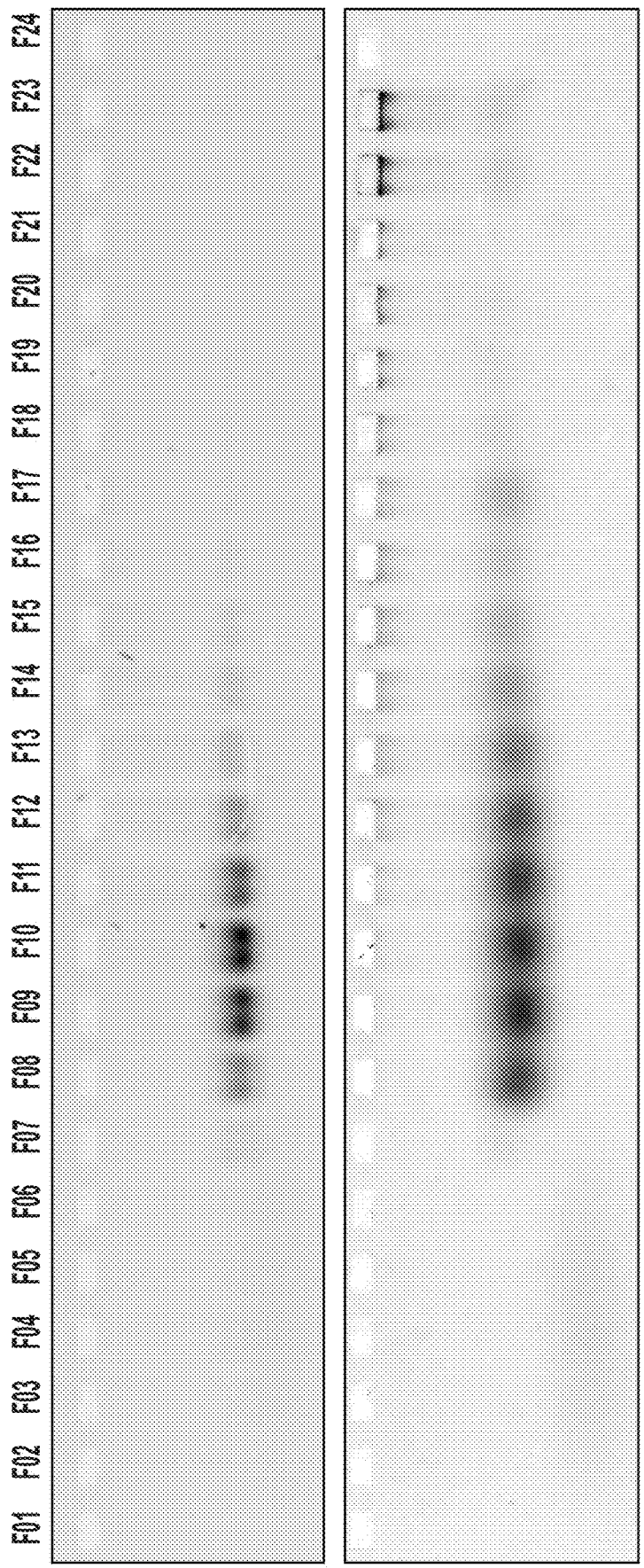
FIG. 6 depicts representative images of agarose gels prepared using fractions from rate-zonal centrifugations run using samples comprising DNA bricks. The top image depicts an agarose gel prepared using fractions comprising 3PS and the bottom image depicts an agarose gel prepared using fractions comprising 6HB. Fractions F01 through F24 were collected from the top to the bottom of a glycerol gradient.
Figure 7:
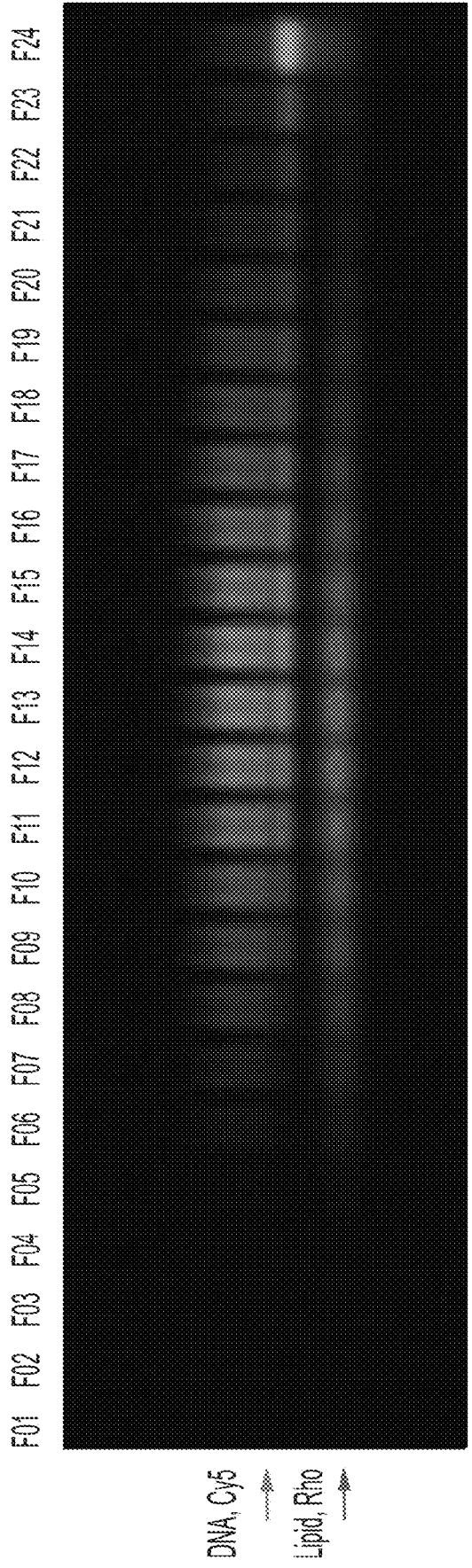
FIG. 7 depicts results obtained from a typical SDS-agarose gel analysis showing the distribution of DNA-coated liposomes in an iodixanol gradient after isopycnic centrifugation. F01-F24 denote fractions collected from top to bottom of the gradient, respectively. Pseudo-color green represents Cy5-labeled DNA bricks, and red depicts rhodamine-labeled lipids. The liposomes were prepared by extrusion of a composition comprising 300 pmol of total lipid through a 50-nm pore size filter. The liposomes were separated from one another into fractions with the help of 3PS DNA bricks. The heaviest fraction (F24) contained a large amount of DNA bricks with negligible amount of lipids, which suggested that most liposomes were surface saturated with 3PS DNA bricks. The liposomes were lysed by SDS in the gel and running buffer, which caused the lipid bands to migrate faster than the DNA-brick bands.

Example 1: DNA Brick-Assisted Sorting and DNA Brick-Based Stabilization of Liposomes Two DNA structures were built as shown in FIGS. 1A and 5. These structures include a three-pointed star [17] (~86 kD) and a six-helix-bundle rod [18] (~189 kD), with a single cholesterol at the end of each DNA structure as the membrane anchor. Placing only one hydrophobic molecule per structure minimized the brick's footprint on a liposome surface and limited aggregation and membrane deformation. To facilitate analysis, ~10% of DNA bricks were labeled with Cy5 fluorophore. After the cholesterol-modified DNA bricks were assembled by thermal annealing and purified by rate-zonal centrifugation, as depicted in FIG. 6, they were incubated with a mixture of extruded and sonicated liposomes (59.2% DOPC, 30% DOPE, 10% DOPS, and 0.8% rhodamine-DOPE) at the brick:lipid molar ratio of 1:375. Centrifuging these DNA-coated liposomes in a gradient of isosmotic density medium (0%-22.5% iodixanol, ~5 mL per tube) at a maximum of ~300 k-rcf for 4.5 hours spread the liposomes into a smeared band spanning the central two thirds of the gradient. Analyzing gradient fractions (~200 µL each, named F1-F24 from top to bottom) by SDS-Agarose gel electrophoresis confirmed the coexistence of DNA bricks and liposomes in the middle portion of the gradient, and revealed free DNA bricks at the very bottom, suggesting the bricks may have saturated the surface of liposomes. See FIG. 7.

Figure 1C:
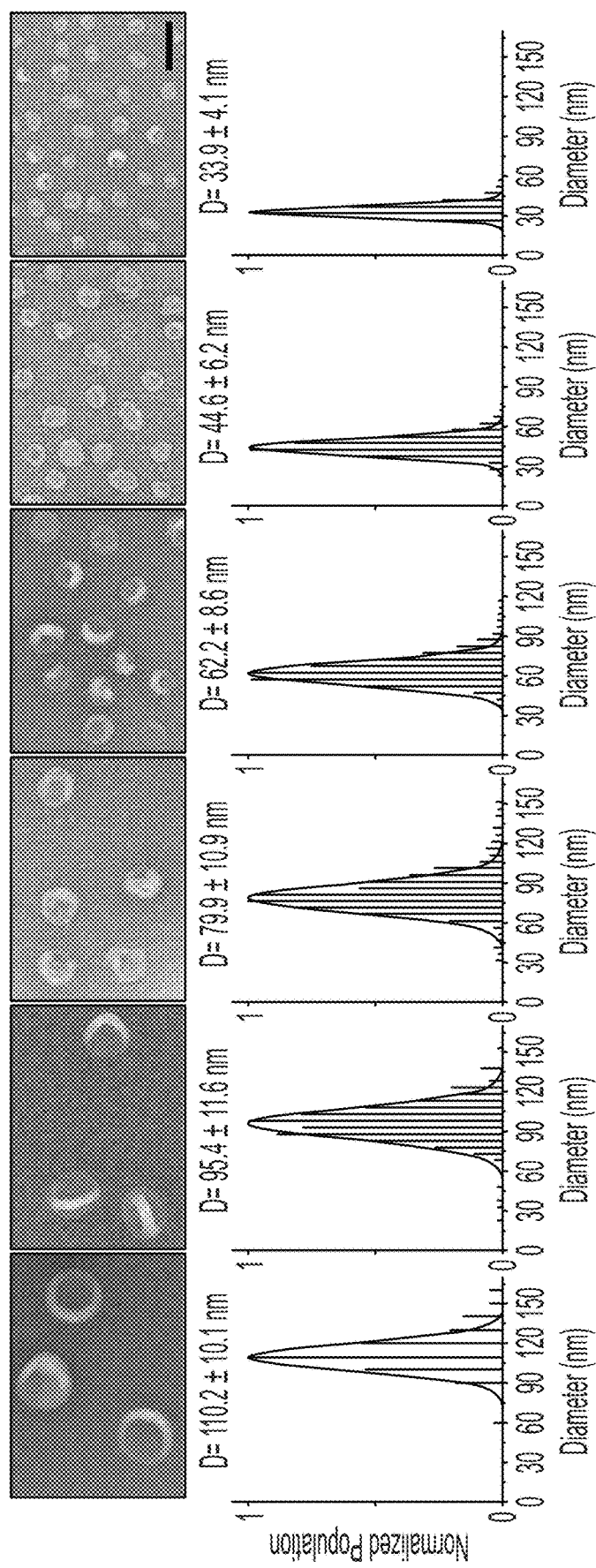
Figure 9:
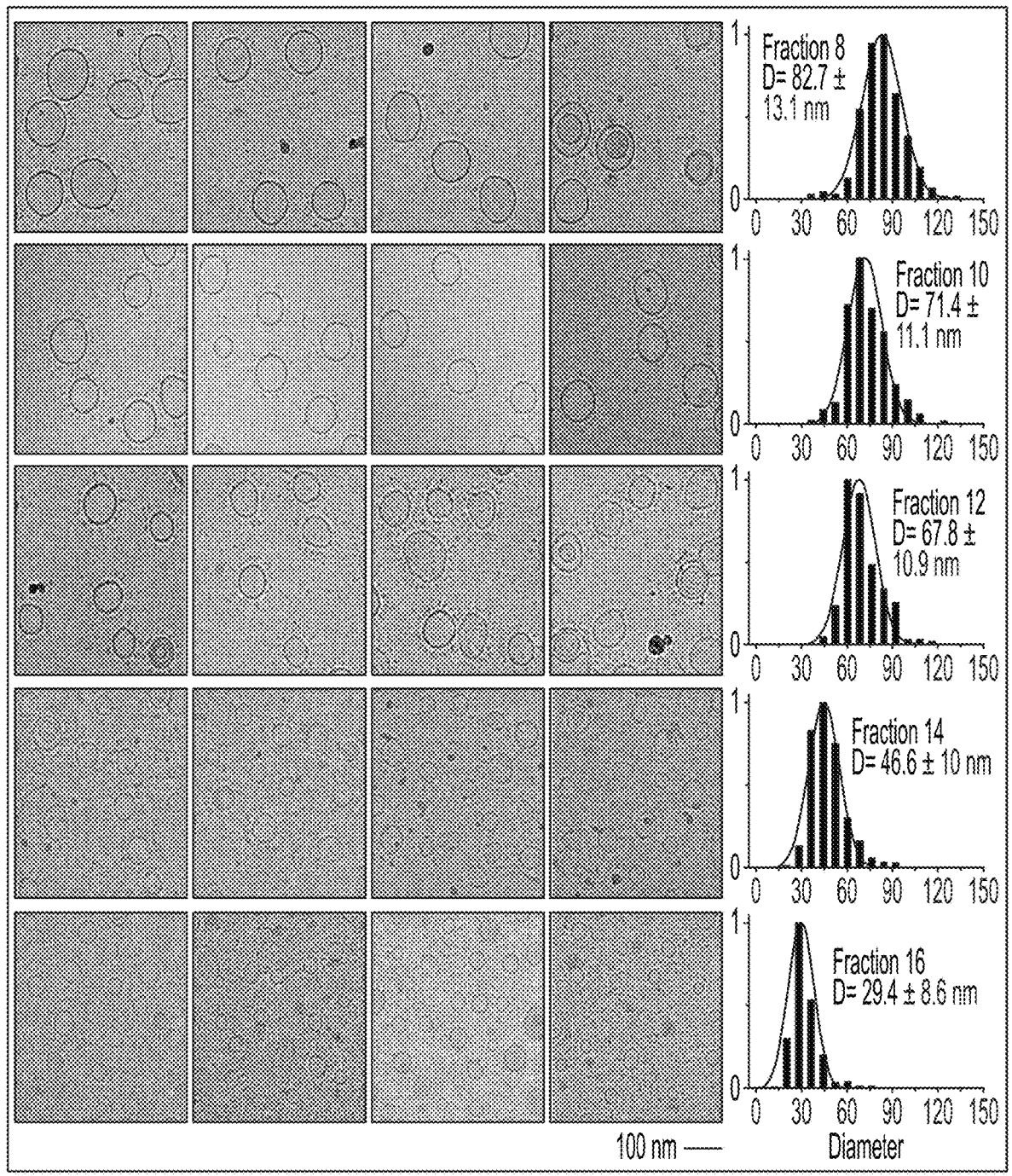
FIG. 9 depicts cryo-EM images of liposomes after being sorted with the help of 6HB DNA bricks. Representative micrographs of fractions 8, 10, 12, 14, and 16 are shown in quadruplicate from top to bottom, respectively, with corresponding histograms showing liposome size distributions for each respective fraction shown to the right. The 6HB DNA bricks were visible on the exterior surface of the liposomes.
Figure 10A:
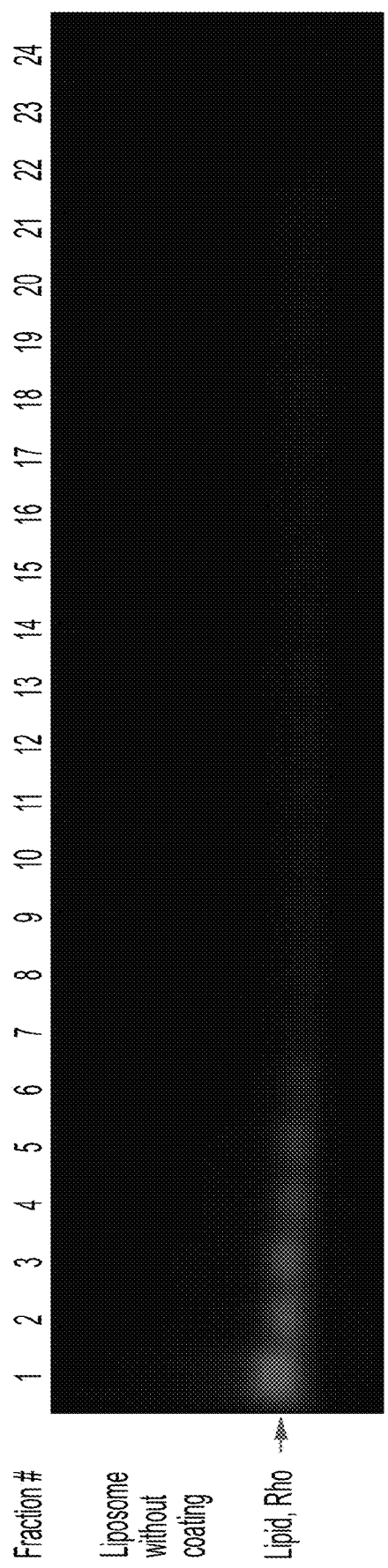
FIGS. 10A-10C depict results obtained from SDS-agarose gel electrophoresis of fractions prepared using uncoated, 3PS DNA brick-coated, and 6HB DNA brick-coated liposomes, respectively. Fractions were separated using an iodixanol density gradient. Fractions from a single iodixanol density gradient were run on the same SDS-agarose gel. Liposomes sorted consisted of a 1:1 total lipid molar ratio of extruded liposomes to sonicated liposomes. Extruded liposomes were prepared using 50-nm pore-size filters. Average surface area occupied by each DNA brick, see bottom panel of FIGS. 10B and 10C, was calculated based on lipid:DNA ratio estimated from band intensities. On average, each brick occupied about 200 nm$^2$ of membrane surface, see bottom panel of FIGS. 10B and 10C. Not wishing to be limited to any particular theory of mode of operation, stronger binding of bricks to smaller liposomes may be a result of there being more lipid packing defects in highly curved membranes.
Figure 10B:
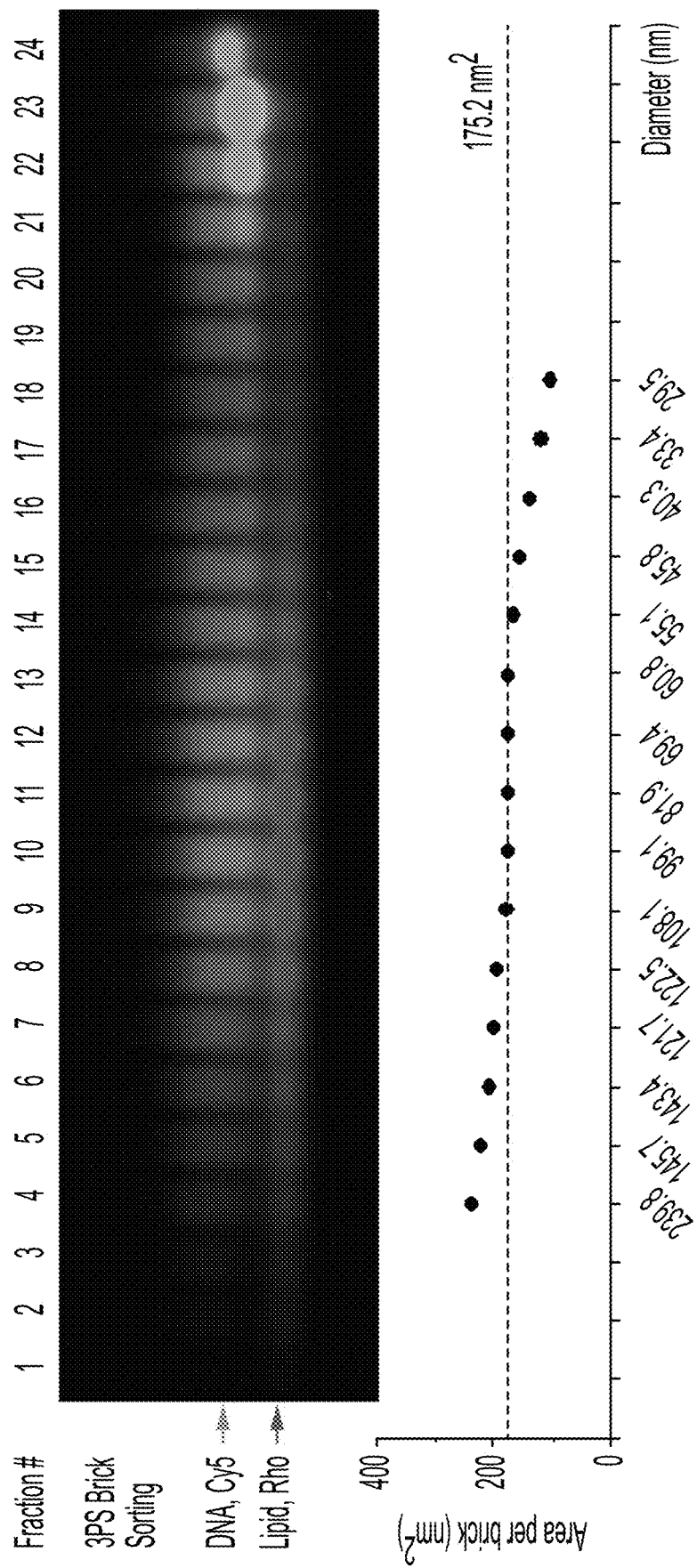
Figure 10C:
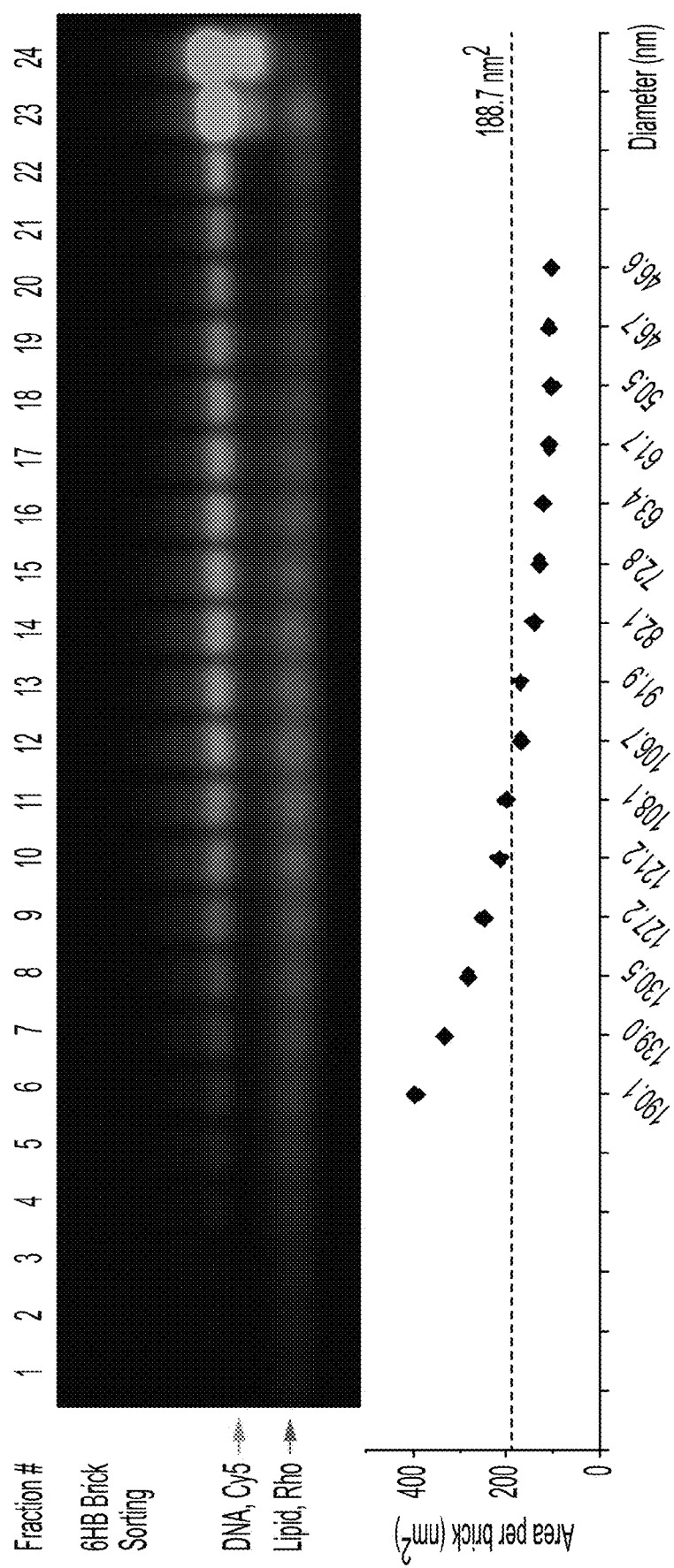
Figure 11A:
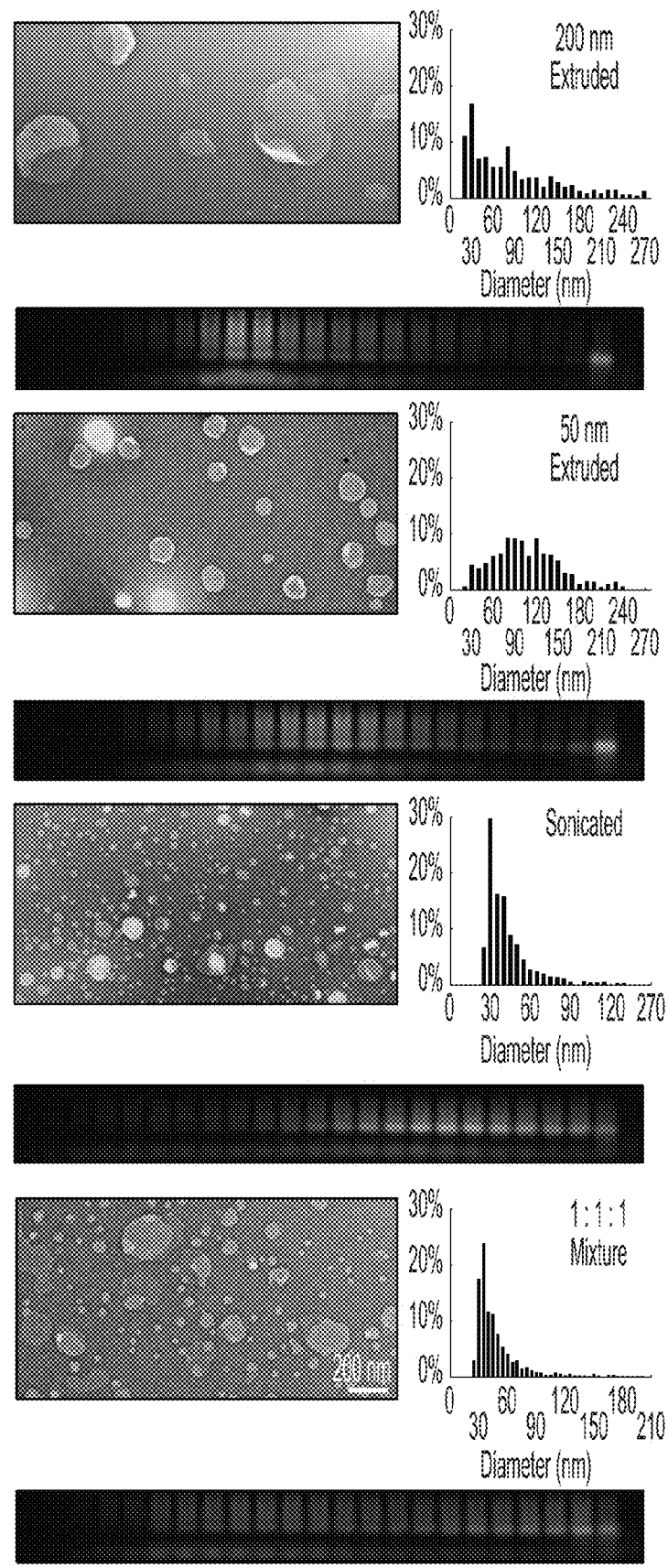
FIGS. 11A and 11B depict results obtained from experiments where DNA-bricks were used to assist in the sorting of liposomes of different origins and size distributions.
Figure 11B:
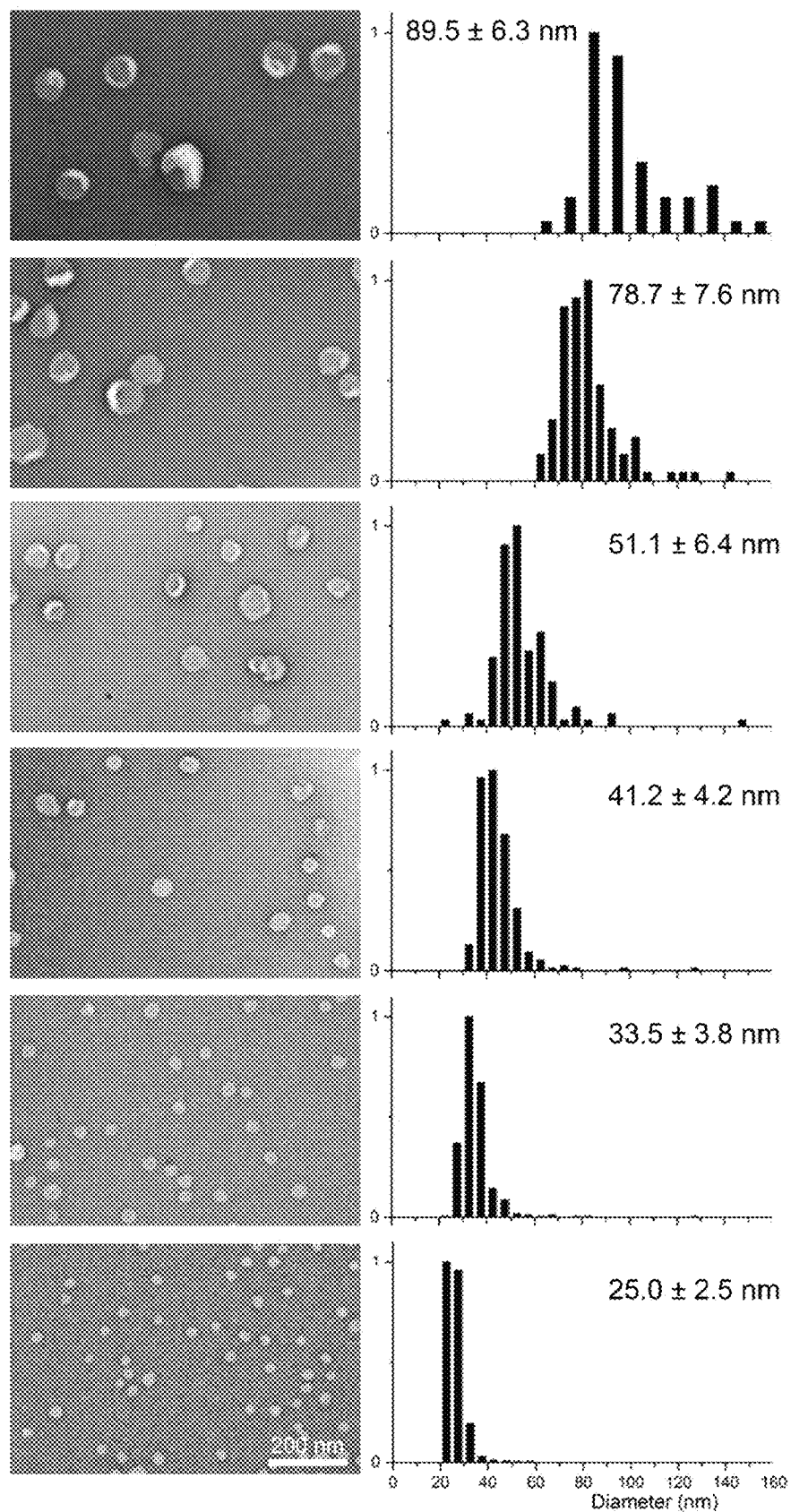
Figure 13:
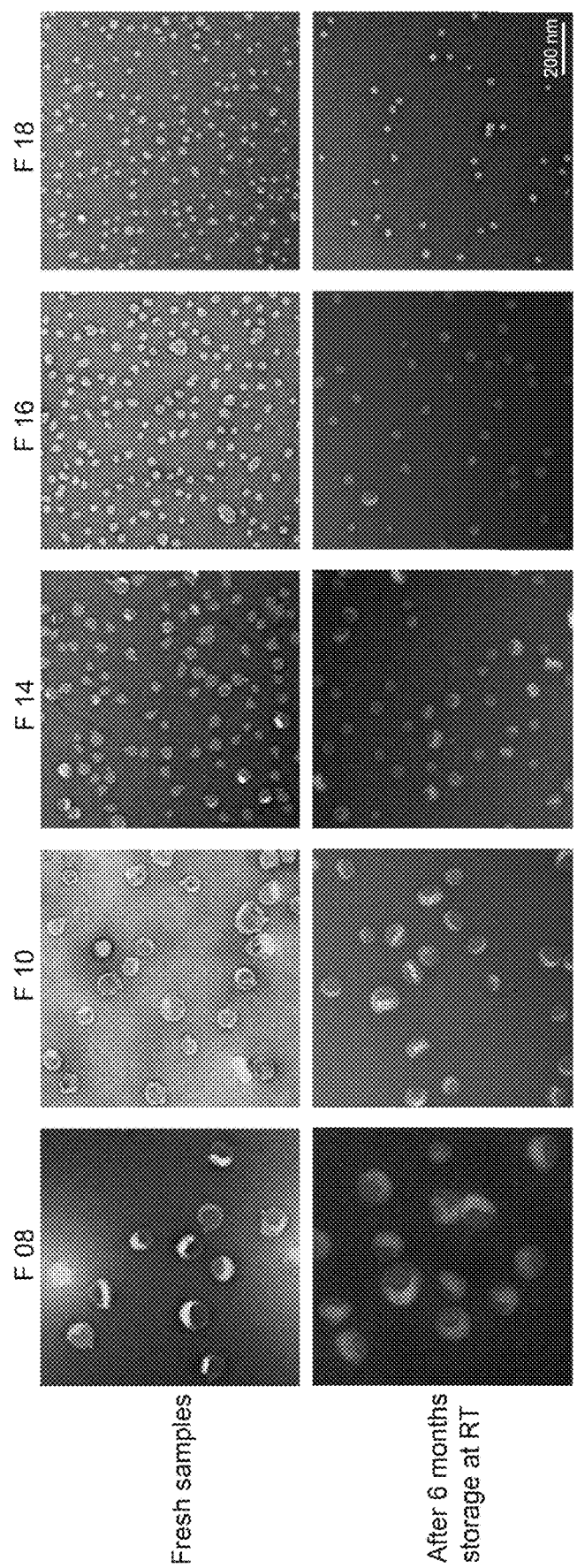
FIG. 13 depicts results obtained from an experiment analyzing the stability of sorted liposomes. The top row depicts TEM images of fresh liposome fractions comprising a 3PS-brick coating. The bottom row depicts TEM images of the same fractions after 6-months of storage at room temperature.

Negative-stain transmission electron microscopy (TEM) showed that F6-F18 each contained uniform-size liposomes with coefficient of variation (CV) less than 15%. See FIGS. 1C and 8. This finding was corroborated by cryo-electron microscopy (cryo-EM), which further showed 77% of liposomes as unilamellar. See FIG. 9. The multi-lamellar liposomes were most likely generated when extruding liposomes through filters with 200-nm pores [4]. The recovered fractions contained liposomes with quasi-continuous mean diameters in the range of 30-130 nm (larger liposomes found in lighter fractions), allowing for selecting or binning any fractions for particular liposome sizes needed in downstream applications. By and large, coating liposomes with the two types of DNA bricks yielded comparable separation resolutions, while uncoated liposomes remained inseparable after centrifugation. See FIGS. 1C and 10. The heavier rod-shaped brick performed better when used to sort the >100-nm liposomes and the three-pointed-star brick led to a finer separation of liposomes smaller than 40 nm. The separation resolution and recovery yield (typically >90%) were consistent from batch to batch, at different separation scales (11 µg-1.3 mg), and across a spectrum of lipid compositions, as long as the liposome surface is not overcrowded with polyethylene glycol. See FIGS. 11-12. Additionally, the dense layer of DNA bricks was clearly visible by electron microscopy in the case of six-helix bundle rods. The dense layer of DNA bricks was able to prolong the shelf life of sorted liposomes (up to 20 weeks at room temperature, as shown in FIG. 13) and was readily removable by DNase I digestion, see FIG. 14.

Example 2: Verification that DNA-Brick Coated Liposomes Did not Detectably Leak

Figure 2A:
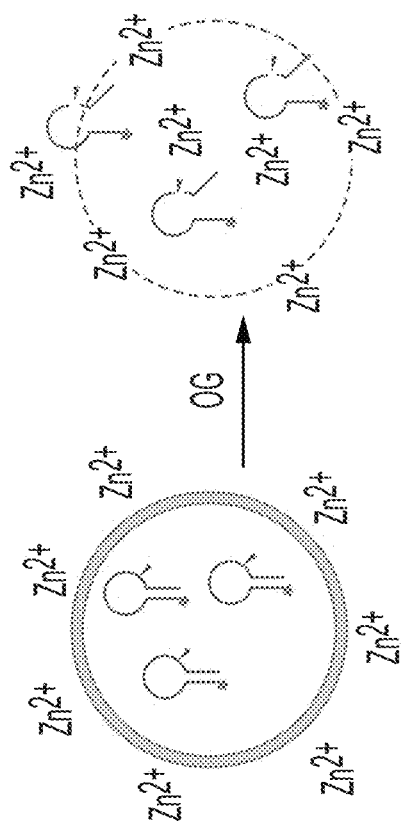
FIGS. 2A-2D describe experiments on sorting liposomes containing self-cleaving deoxyribozymes.
Figure 2B:
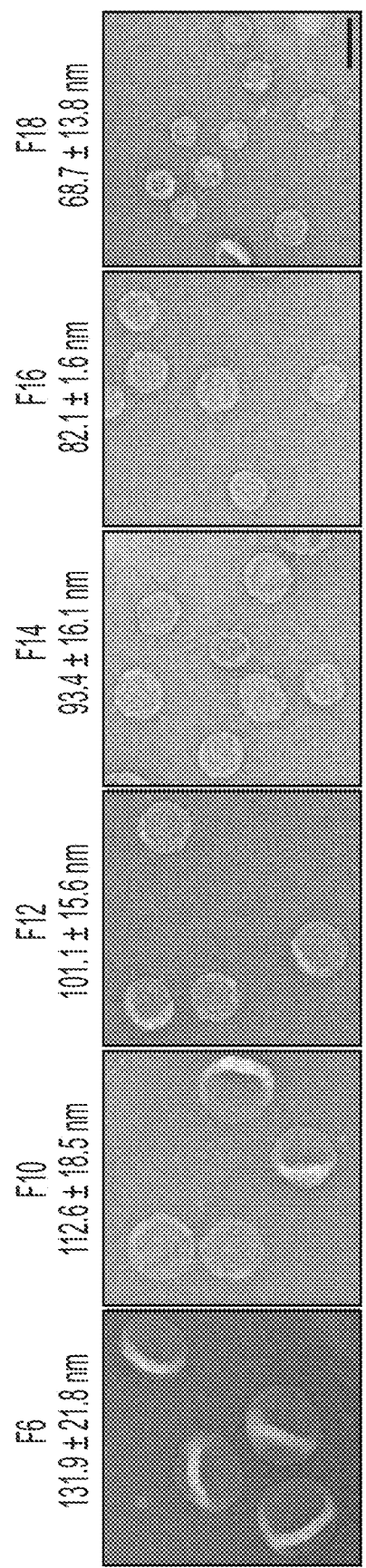
Figure 2C:
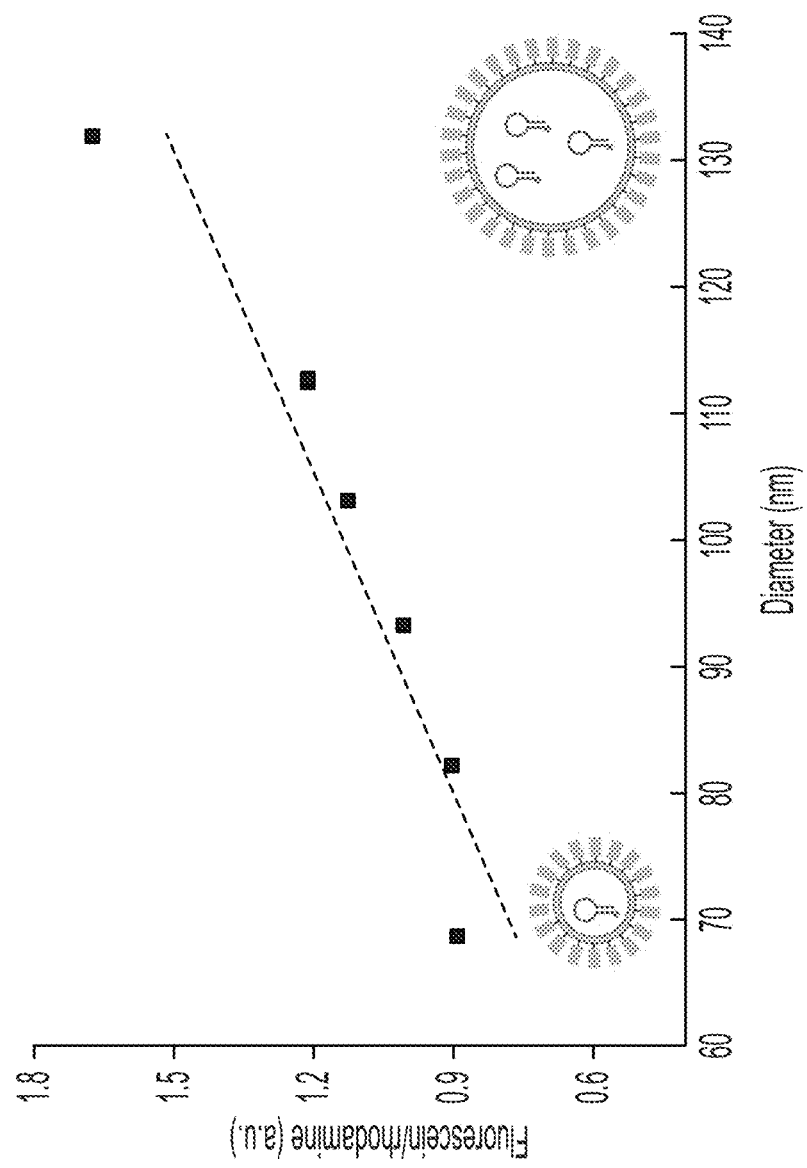
Figure 2D:
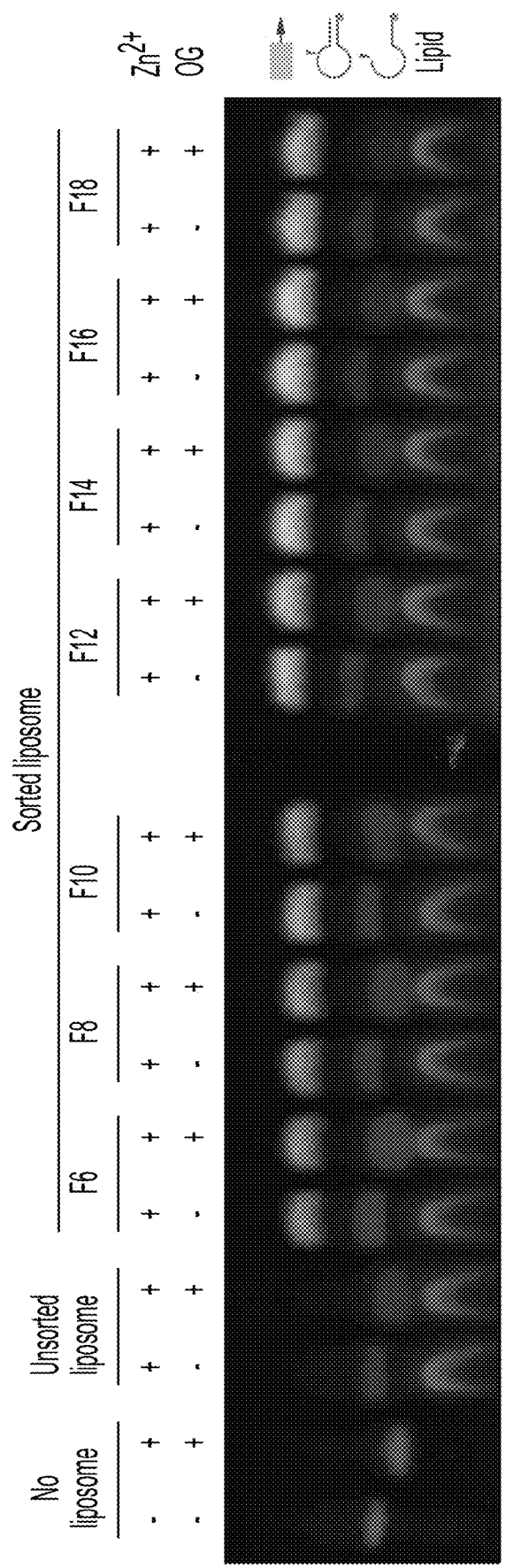
Figure 15:
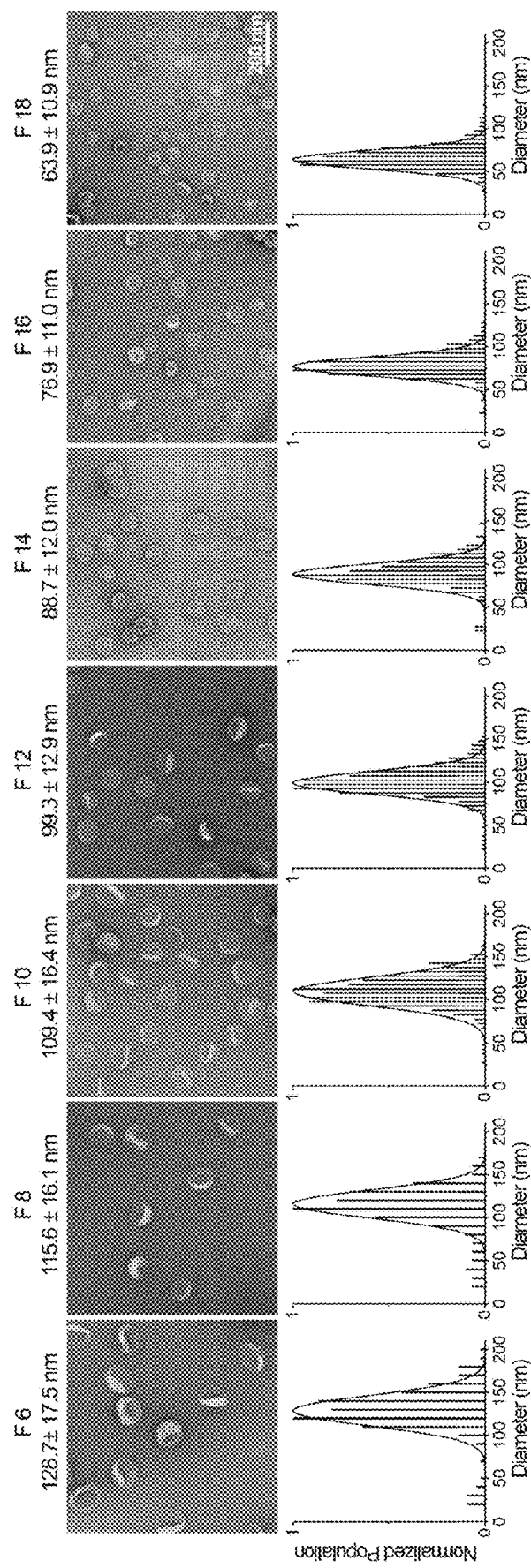
FIG. 15 depicts results gathered from 6HB DNA brick-assisted sorting of deoxyribozyme encapsulating liposomes. For sorted liposomes in each indicated fraction, a representative TEM image is shown on top of a corresponding histogram of liposome diameters for each indicated fraction. The liposomes contained deoxyribozyme I-R1a and were sorted with the help of 6HB bricks.

The well-maintained monodispersity after long-term storage and the clear, intact boundaries observed by cryo-EM were promising signs of membrane integrity of sorted liposomes. To confirm this, 6-helix-bundle bricks were used to assist the sorting of extruded liposomes (a 1:1 mixture of liposomes passed through filters with 200-nm and 50-nm pores) loaded with fluorescein-labeled class I deoxyribozymes (I-R1a) (SEQ ID NO: 24), which self-cleave in minutes upon exposure to ~1 mM $Zn^{2+}$ at near neutral pH, as shown in FIG. 2A. Similar to the plain liposomes, most of deoxyribozyme-loaded liposomes with DNA-brick coatings were sorted into six homogeneous populations with mean diameters from 64 to 129 nm. See FIG. 2B. Few smaller liposomes recovered due to their scarcity in the extruded liposomes. See FIG. 15. The narrow size distribution of each sorted fractions contrasted with the heterogeneous populations generated by filter-driven homogenization, again highlighting the effectiveness and necessity of DNA-assisted sorting. The molar ratio between lipid and deoxyribozyme (determined by the fluorescence of rhodamine and fluorescein) was inversely proportional to liposome diameter, as expected from SN of a sphere, indicating the unbiased cargo load in all sizes of liposome, as shown in FIG. 2C. Moreover, the liposomes, sorted or not, were impermeable to $Zn^{2+}$ (2 mM) and deoxyribozyme (1 µM), showing no detectable I-R1a self-cleavage when incubated with $Zn^{2+}$-containing solutions for over 12 hours, until liposomes were lysed with detergent (1% octyl β-D-glucopyranoside).

Figure 3A:
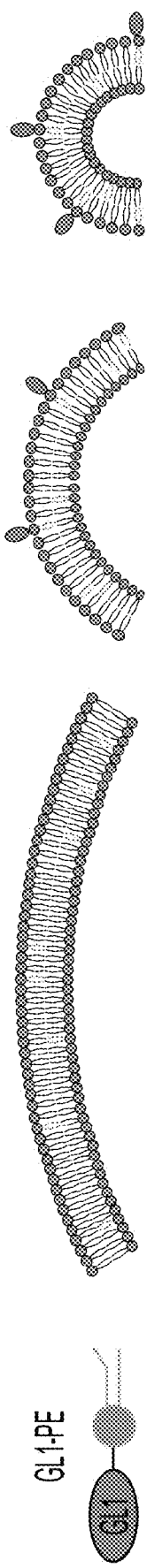
FIGS. 3A and 3B depict an Atg3-catalyzed GL1 lipidation reaction studied using uniform-size liposomes.
Figure 3B:
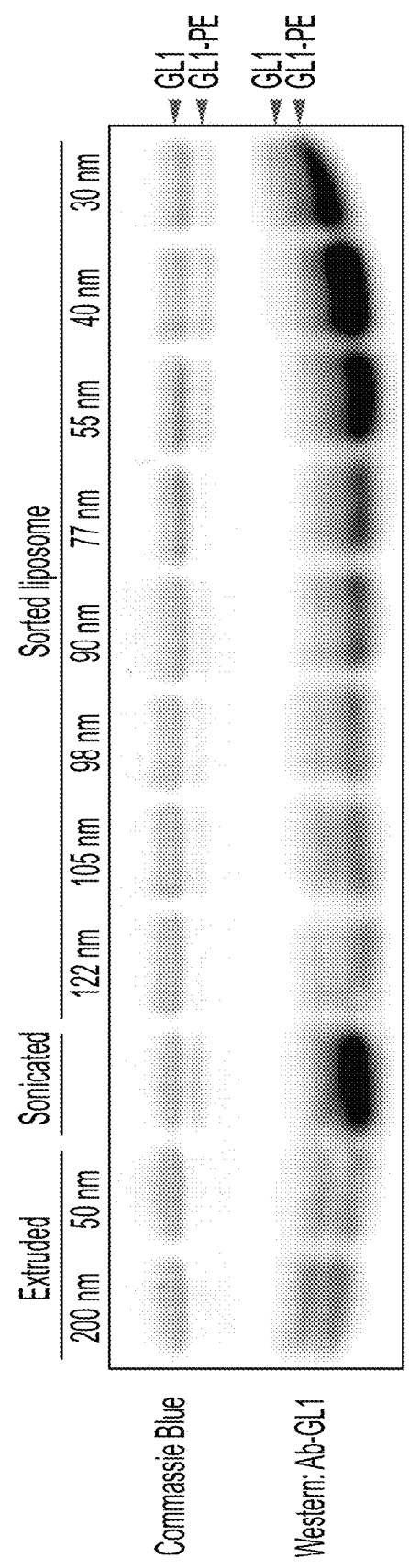
Figure 16:
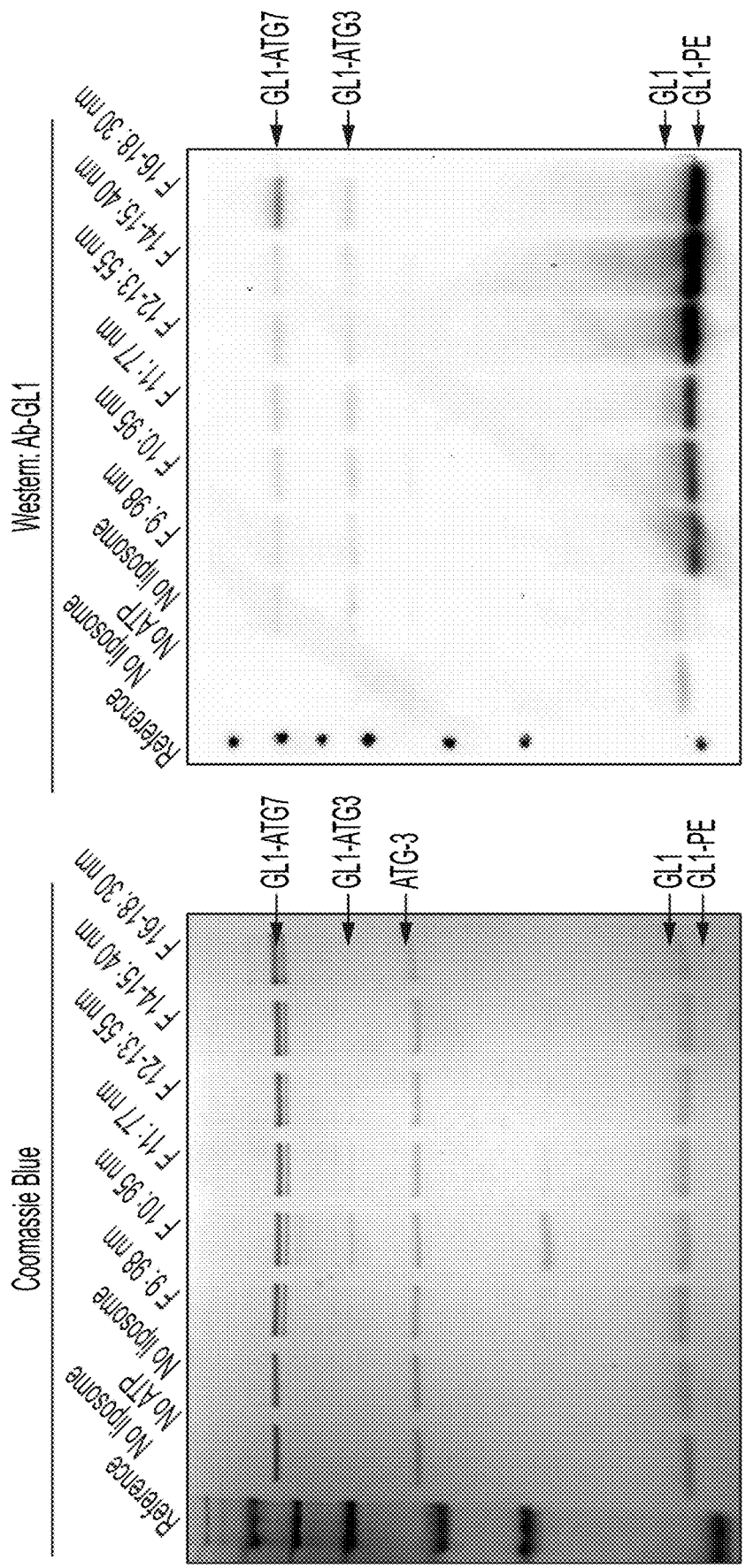
FIG. 16 shows images of results obtained from an experiment analyzing curvature dependency of ATG7/ATG3 catalyzed GL1 lipidation. Typical SDS-PAGE and Western blot analyses of GL1 lipidation reactions are shown in the left and right panels, respectively.
Figure 17:
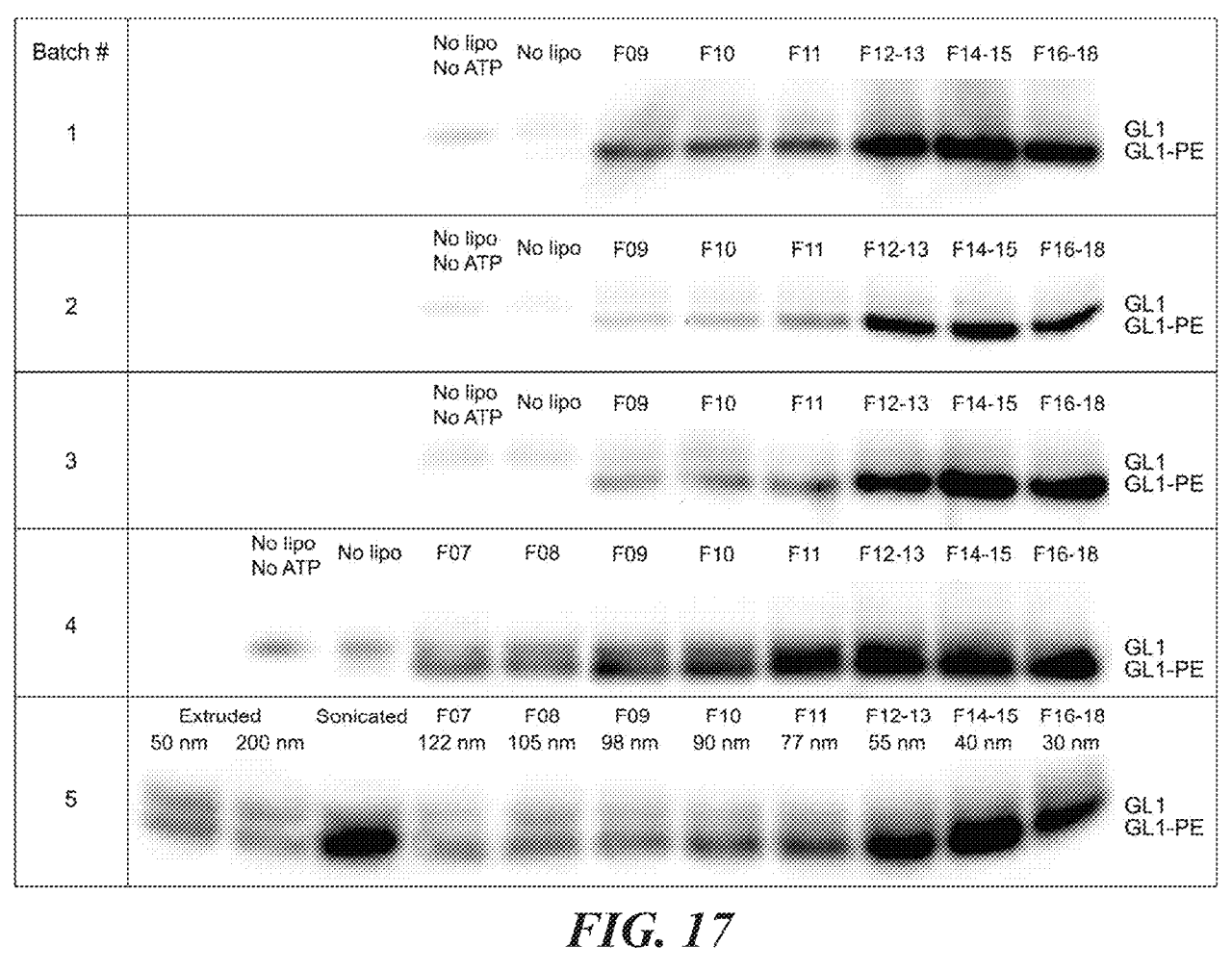

Example 3: Use of Sorted Liposomes to Study the Curvature-Sensing Capability of a Conjugating Enzyme that Works on the Membrane Surface of the Autophagosome Sorted liposomes (59.2% DOPC, 30% DOPE, 10% DOPS, and 0.8% rhodamine-DOPE) of eight selected sizes (mean diameter: 30, 40, 55, 77, 90, 98, 105, and 122 nm) were used for ATG3-catalyzed reactions to confirm that the lipidation of GL1 favored smaller liposomes possessing higher curvature. Specifically, data revealed a circa 5× enrichment of GL1-PE conjugates in liposomes that are 30-55 nm in diameter compared to larger liposomes with the lipidation peaking on liposomes with ~40-nm diameter, as shown in FIGS. 3 and 16-17. This curvature range is reminiscent of the typical autophagosome rim (20-50 nm lamellar spacing) [20], the inferred hotspot of ATG3-dependent lipidation in vivo. As ATG3 is a peripheral protein, it must gain access to the membrane surface and thus a potential concern of using sorted liposomes is that the DNA bricks might directly impede lipidation. Though the DNA bricks are essentially inert with respect to protein activity, the membrane surface is not obscured by treating the sorted liposomes with nuclease prior to the lipidation assay. Overall, homogeneous liposomes improved the precision of the in vitro lipidation assay, enabling a quantitative measurement of the curvature-dependent ATG3/ATG7 ligation cascade.

Figure 4A:
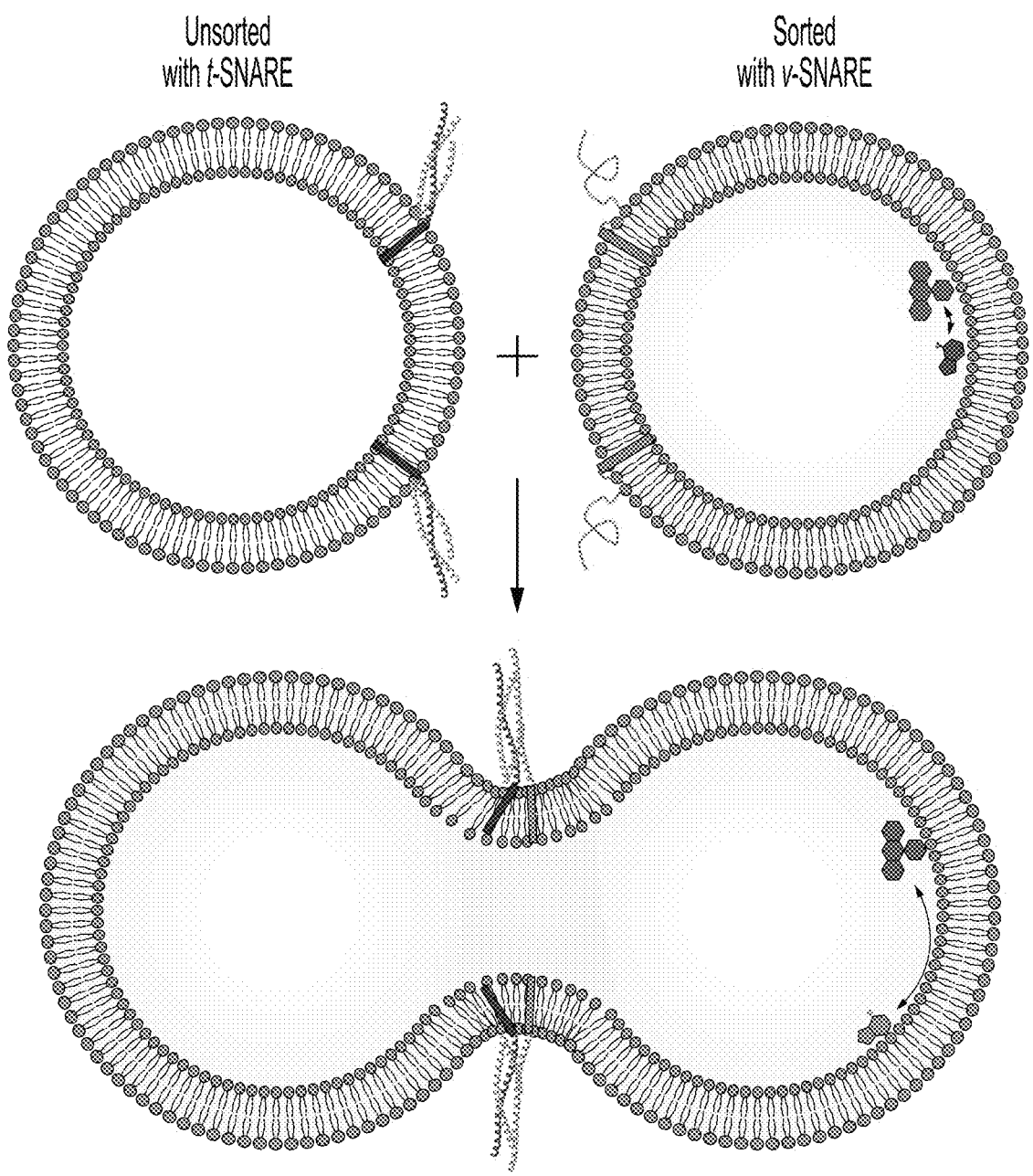
FIGS. 4A-4D depict SNARE-mediated membrane fusion studied using uniform-size liposomes.
Figure 18A:
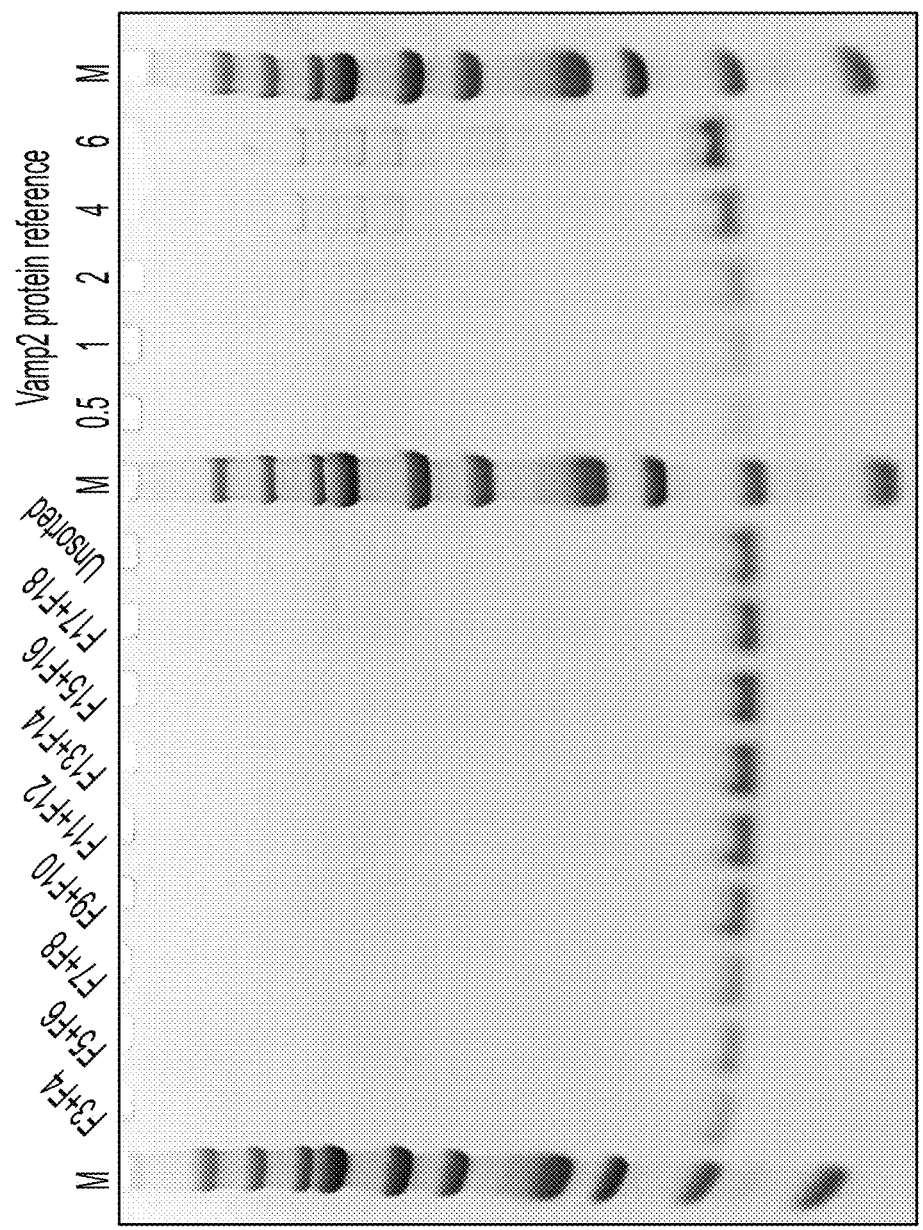
FIGS. 18A-18C depict results obtained from the characterizations of proteoliposomes containing VAMP2. VAMP2 protein in reconstituted proteoliposomes was quantified before and after sorting, see FIGS. 18A and 18B. For quantification, liposomes reconstituted with VAMP2 were analyzed by SDS-PAGE alongside protein concentration references, see FIG. 18A.
Figure 18B:
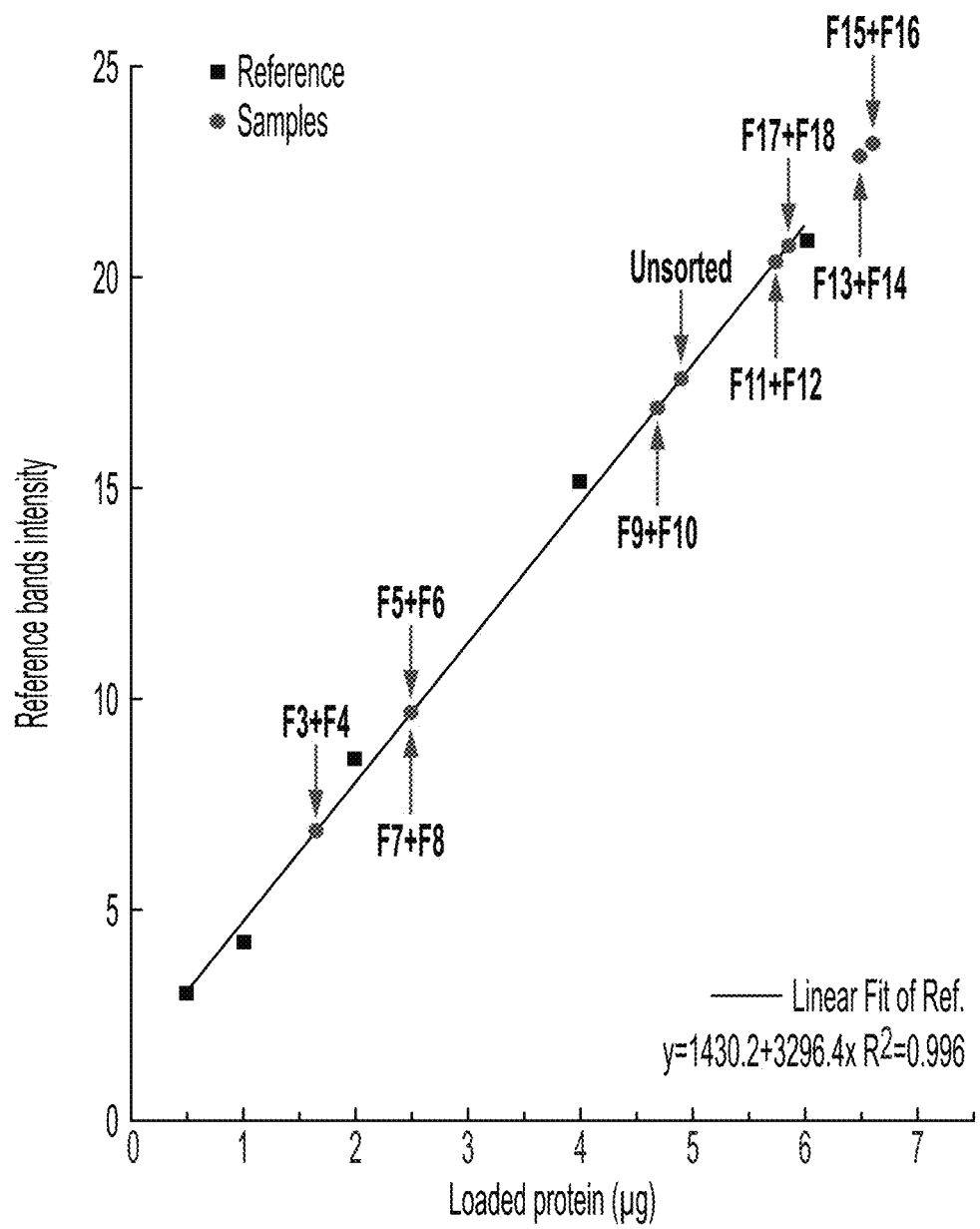
Figure 18C:
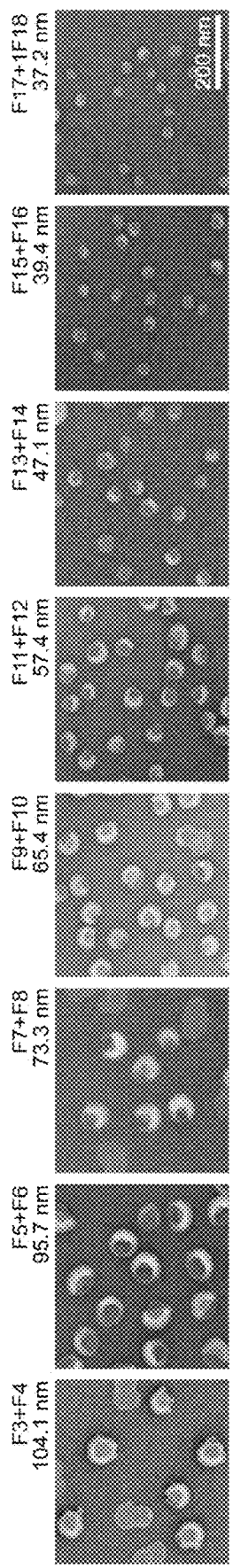
Figure 19A:
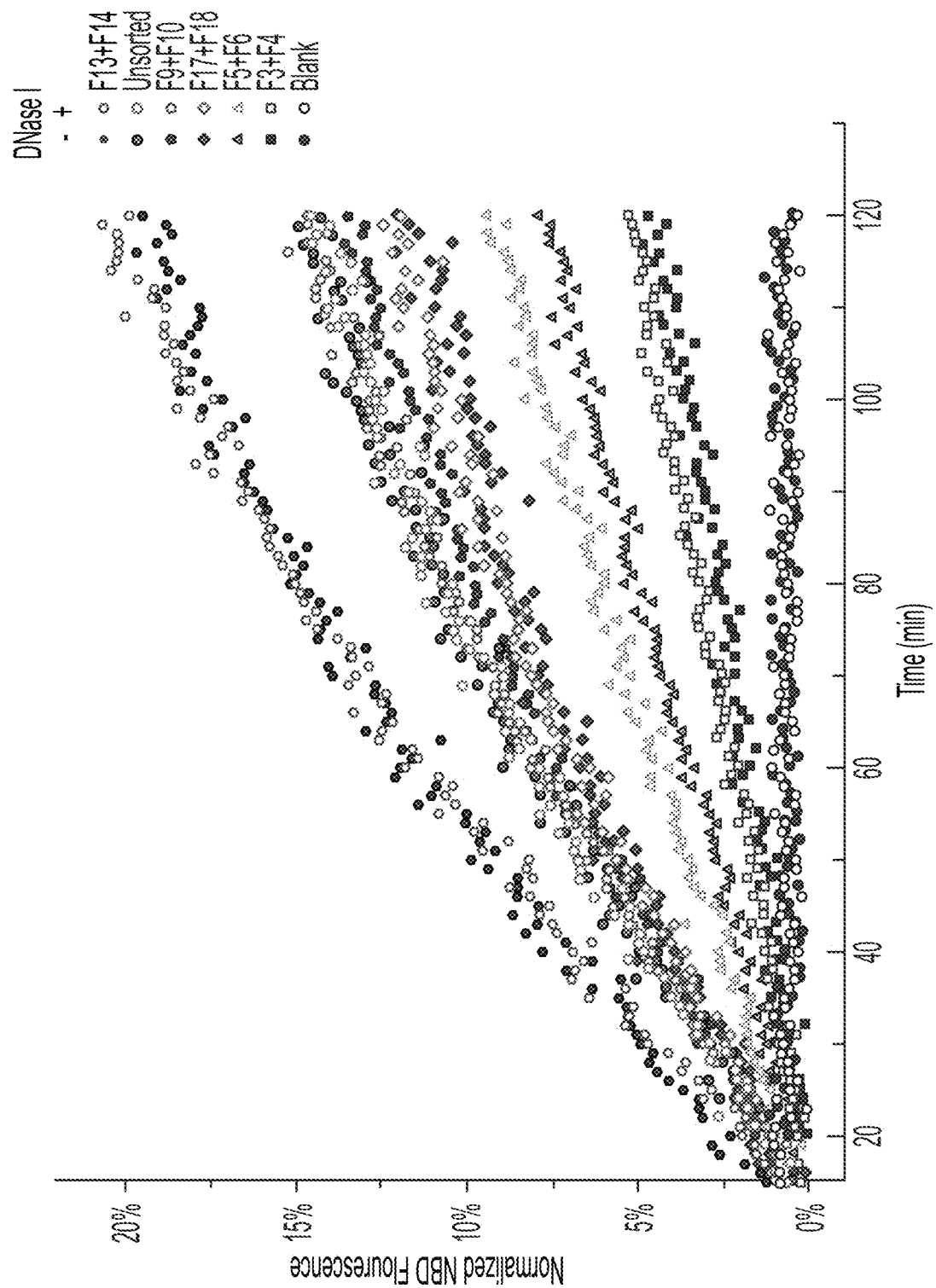
FIGS. 19A and 19B depict results obtained from experiments analyzing the effect of membrane-bound DNA bricks on a fusion assay.
Figure 19B:
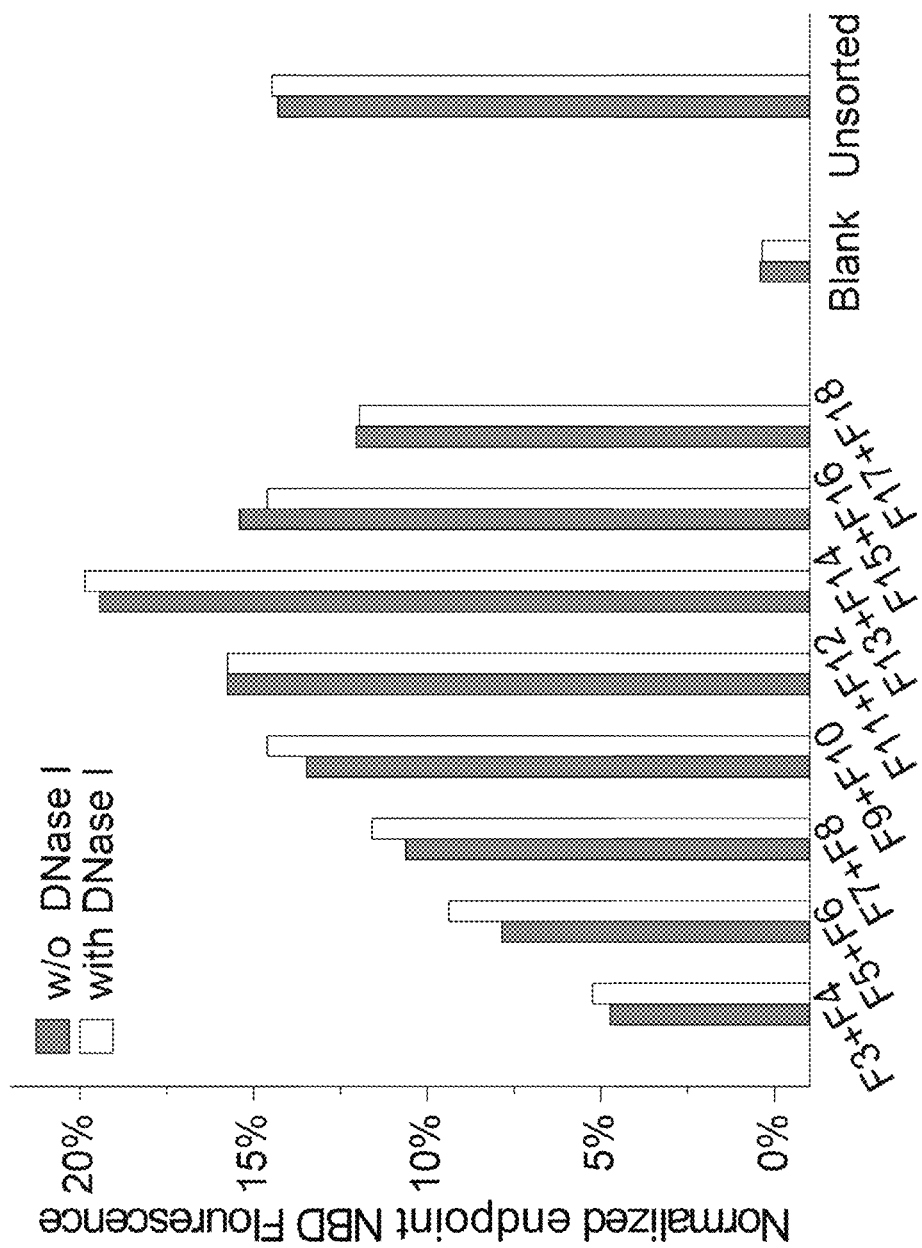
Figure 20A:
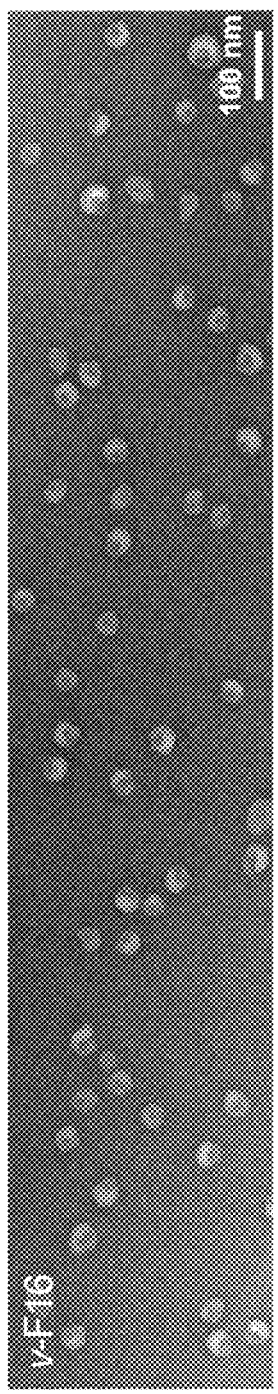
FIG. 20A-20C demonstrate liposome docking in a pre-incubation period as visualized by negative-stain TEM.
Figure 20B:
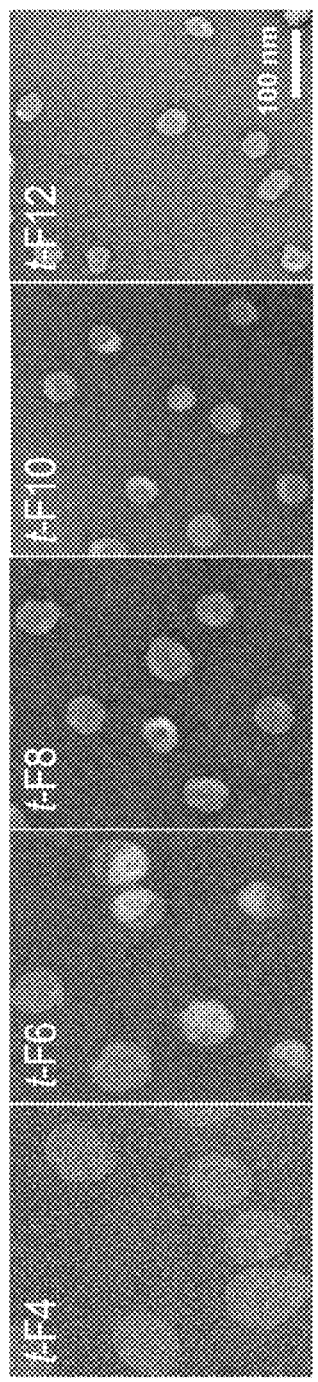
Figure 20C:
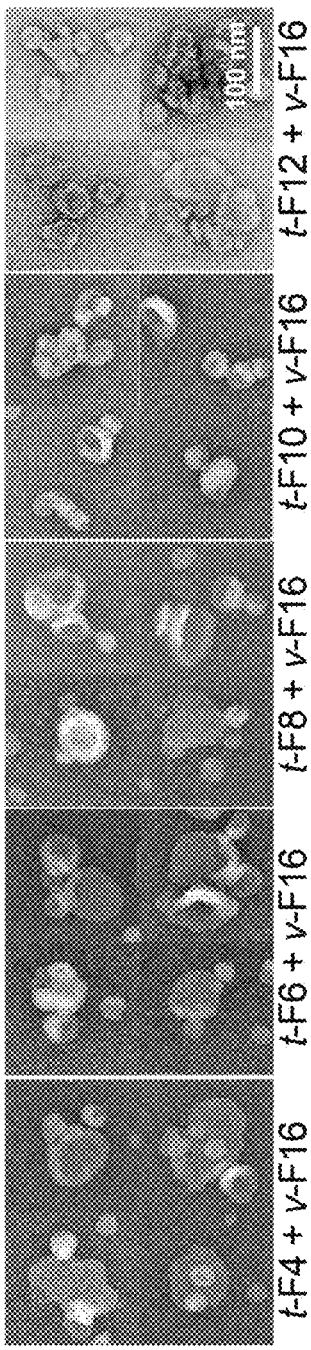

Example 4: Using Sorted Liposomes to Produce Proteoliposomes with Well-Defined Sizes The neuronal/exocytotic v-SNARE VAMP2 was reconstituted into liposomes (lipid:VAMP2≈200:1) containing FRET-dye-labeled lipids (NBD- and rhodamine-DOPE) and DNA-brick assisted sorting was performed on 440 µg of such proteoliposomes. The pre-existence of proteins in vesicle membranes did not compromise separation effectiveness, as confirmed by negative-stain TEM. The results are shown in FIG. 18. After enzymatic removal of DNA bricks (noting that the procedure was unnecessary in hindsight as the DNA bricks did not affect fusion, see FIG. 19), VAMP-embedded liposomes of eight different diameters (37-104 nm) were mixed with unlabeled (and unsorted) liposomes carrying cognate t-SNAREs in separate test tubes; the mixtures (lipid concentration=3 mM) were kept at 4° C. for 2 hrs, a temperature that allows vesicle docking but no fusion, as shown in FIG. 20. Finally, the pre-docked liposomes were warmed to 37° C. and NBD fluorescence was monitored for 2 hours using a fluorescence microplate reader. Merging of liposome membranes increases the distance between NBD dyes and their rhodamine quenchers provided a read-out of lipid mixing kinetics, as shown in FIG. 4A. Consistent with previous findings [22, 25, 27], membrane fusion is SNARE dependent.

Figure 4B:
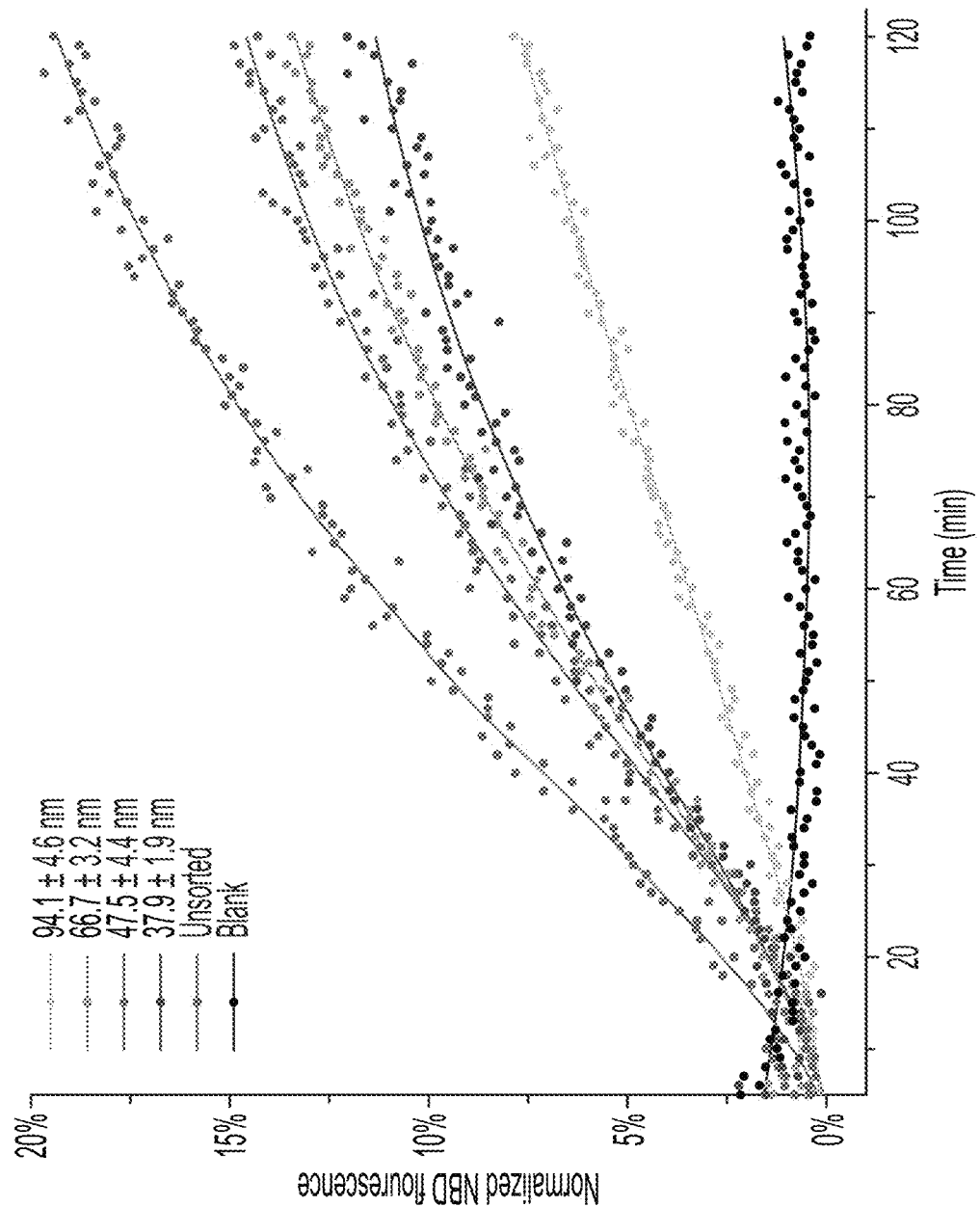
Figure 4C:
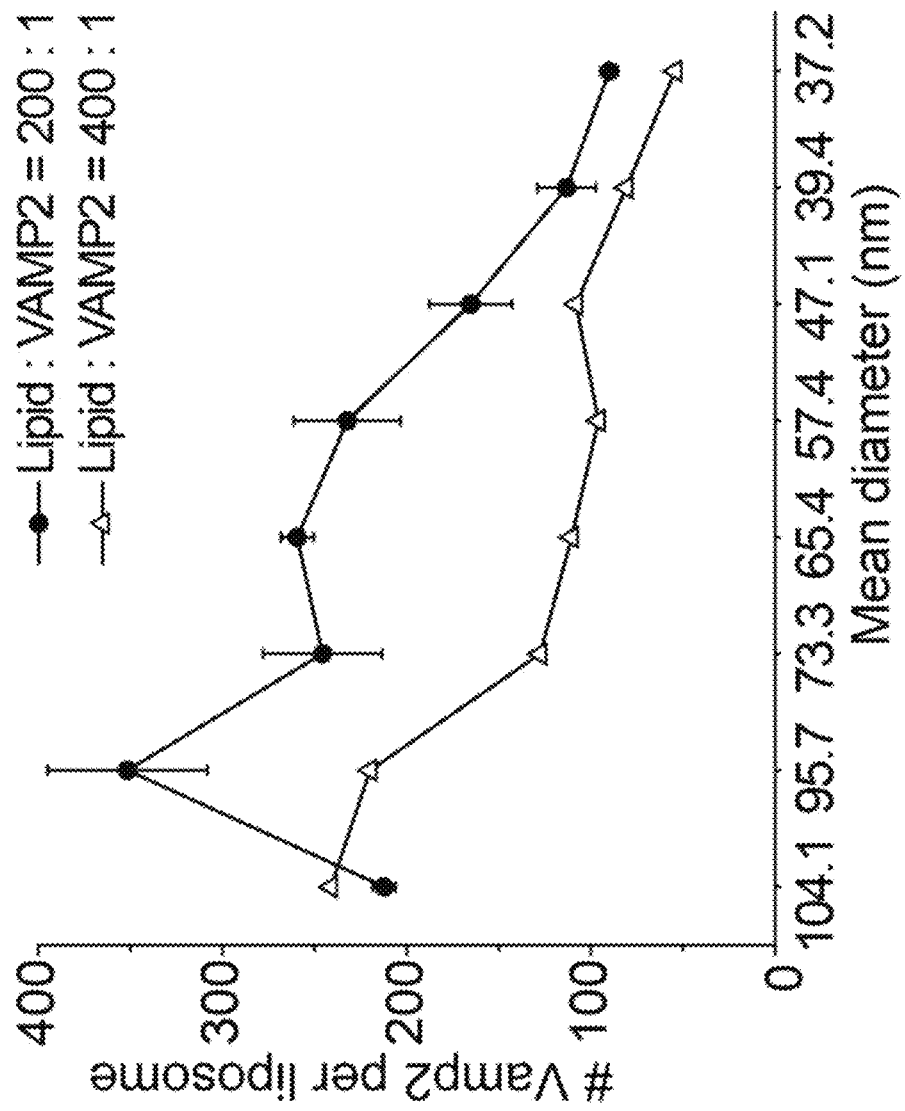
Figure 4D:
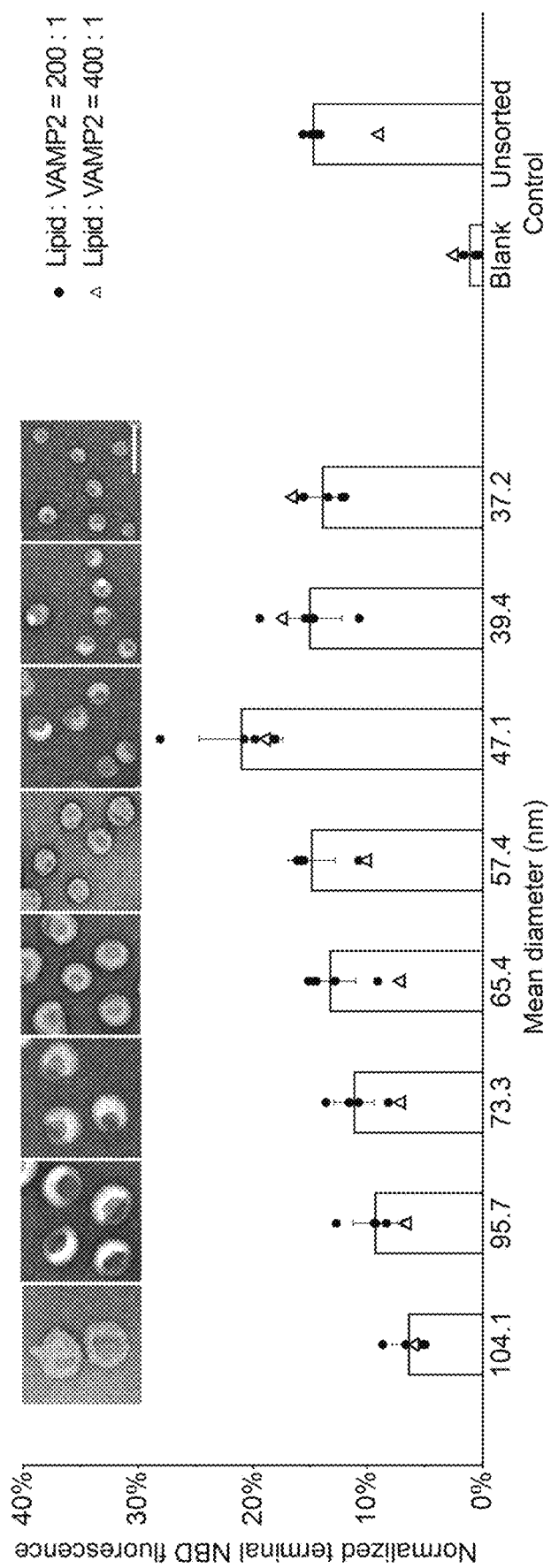

However, unlike conventional assays, use of vesicles of well-defined sizes allowed for determination of lipid mixing kinetics as a function of vesicle size. See FIG. 4B. When mean v-SNARE-bearing liposome diameters were within 47-104 nm, smaller liposomes fused more rapidly, with the most and least fusogenic vesicles showing ~3-fold difference in the final NBD fluorescence. Further decreasing liposome diameter to an average of 37 nm slowed fusion only moderately. Assays with halved VAMP2 density on liposomes yielded a similar trend, as shown in FIGS. 4C and 4D. When lipid:VAMP2 ratios were held constant, smaller liposomes tended to display less v-SNAREs, which may explain slower fusion of 37-nm liposomes compared to 47-nm liposomes. That is, there seems to be an optimal combination of SNARE copies per liposome and membrane curvature—an effect that would not have been captured without precise control of liposome sizes.

REFERENCES

1. Woodle, M. C. & Papahadjopoulos, D. Liposome preparation and size characterization. Methods Enzymol 171, 193-217 (1989).
2. Schubert, R. Liposome preparation by detergent removal. Methods Enzymol 367, 46-70 (2003).
3. Patil, Y. P. & Jadhav, S. Novel methods for liposome preparation. Chem Phys Lipids 177, 8-18 (2014).
4. Berger, N., Sachse, A., Bender, J., Schubert, R. & Brandl, M. Filter extrusion of liposomes using different devices: comparison of liposome size, encapsulation efficiency, and process characteristics. Int J Pharm 223, 55-68 (2001).
5. Silva, R., Ferreira, H., Little, C. & Cavaco-Paulo, A. Effect of ultrasound parameters for unilamellar liposome preparation. Ultrason Sonochem 17, 628-632 (2010).
6. Stachowiak, J. C. et al. Unilamellar vesicle formation and encapsulation by microfluidic jetting. Proc Natl Acad Sci USA 105, 4697-4702 (2008).
7. van Swaay, D. & deMello, A. Microfluidic methods for forming liposomes. Lab Chip 13, 752-767 (2013).
8. Yang, Y. et al. Self-assembly of size-controlled liposomes on DNA nanotemplates. Nat Chem 8, 476-483 (2016).
9. Zhang, Z., Yang, Y., Pincet, F., Llaguno, M. C. & Lin, C. X. Placing and shaping liposomes with reconfigurable DNA nanocages. Nat Chem 9, 653-659 (2017).
10. Perrault, S. D. & Shih, W. M. Virus-Inspired Membrane Encapsulation of DNA Nanostructures To Achieve In Vivo Stability. Acs Nano 8, 5132-5140 (2014).
11. Daniel, E. Equilibrium sedimentation of a polyelectrolyte in a density gradient of a low-molecular weight electrolyte. I. DNA in CsCl. Biopolymers 7, 359-377 (1969).
12. Seeman, N. C. & Sleiman, H. F. DNA nanotechnology. Nat Rev Mater 3 (2018).
13. Kwak, M. & Herrmann, A. Nucleic acid amphiphiles: synthesis and self-assembled nanostructures. Chem Soc Rev 40, 5745-5755 (2011).
14. Langecker, M., Arnaut, V., List, J. & Simmel, F. C. DNA nanostructures interacting with lipid bilayer membranes. Acc Chem Res 47, 1807-1815 (2014).
15. Howorka, S. NANOTECHNOLOGY. Changing of the guard. Science 352, 890-891 (2016).
16. Shen, Q., Grome, M. W., Yang, Y. & Lin, C. Engineering Lipid Membranes with Programmable DNA Nanostructures. Advanced Biosystems 4, 1900215 (2020).
17. He, Y., Chen, Y., Liu, H., Ribbe, A. E. & Mao, C. Self-assembly of hexagonal DNA two-dimensional (2D) arrays. J Am Chem Soc 127, 12202-12203 (2005).
18. Mathieu, F. et al. Six-helix bundles designed from DNA. Nano Lett 5, 661-665 (2005).
19. Du, X. Y., Zhong, X., Li, W., Li, H. & Gu, H. Z. Retraining and Optimizing DNA-Hydrolyzing Deoxyribozymes for Robust Single- and Multiple-Turnover Activities. Acs Catal 8, 5996-6005 (2018).
20. Nguyen, N., Shteyn, V. & Melia, T. J. Sensing Membrane Curvature in Macroautophagy. J Mol Biol 429, 457-472 (2017).

21 Nath, S. et al. Lipidation of the LC3/GABARAP family of autophagy proteins relies on a membrane-curvature-sensing domain in Atg3. Nat Cell Biol 16, 415-424 (2014).
22 Weber, T. et al. SNAREpins: minimal machinery for membrane fusion. Cell 92, 759-772 (1998).
23 Jahn, R. & Scheller, R. H. SNAREs—engines for membrane fusion. Nat Rev Mol Cell Biol 7, 631-643 (2006).
24 Sudhof, T. C. & Rothman, J. E. Membrane fusion: grappling with SNARE and SM proteins. Science 323, 474-477 (2009).
25 Hernandez, J. M. et al. Membrane fusion intermediates via directional and full assembly of the SNARE complex. Science 336, 1581-1584 (2012).
26 Hernandez, J. M., Kreutzberger, A. J., Kiessling, V., Tamm, L. K. & Jahn, R. Variable cooperativity in SNARE-mediated membrane fusion. Proc Natl Acad Sci USA 111, 12037-12042 (2014).
27 Ji, H. et al. Protein determinants of SNARE-mediated lipid mixing. Biophys J 99, 553-560 (2010).
28 Xu, W. M. et al. A Programmable DNA Origami Platform to Organize SNAREs for Membrane Fusion. J Am Chem Soc 138, 4439-4447 (2016).
29 Zhang, B. et al. Synaptic vesicle size and number are regulated by a clathrin adaptor protein required for endocytosis. Neuron 21, 1465-1475 (1998).
30 Qu, L., Akbergenova, Y., Hu, Y. & Schikorski, T. Synapse-to-synapse variation in mean synaptic vesicle size and its relationship with synaptic morphology and function. J Comp Neurol 514, 343-352 (2009).
31 Czogalla, A. et al. Amphipathic DNA Origami Nanoparticles to Scaffold and Deform Lipid Membrane Vesicles. Angew Chem Int Edit 54, 6501-6505 (2015).
32 Grome, M. W., Zhang, Z., Pincet, F. & Lin, C. X. Vesicle Tubulation with Self-Assembling DNA Nanosprings. Angew Chem Int Edit 57, 5330-5334 (2018).
33 Franquelim, H. G., Khmelinskaia, A., Sobczak, J. P., Dietz, H. & Schwille, P. Membrane sculpting by curved DNA origami scaffolds. Nat Commun 9, 811 (2018).
34 Journot, C. M. A., Ramakrishna, V., Wallace, M. I. & Turberfield, A. J. Modifying Membrane Morphology and Interactions with DNA Origami Clathrin-Mimic Networks. Acs Nano 13, 9973-9979 (2019).
35 Nair, U. et al. SNARE proteins are required for macroautophagy. Cell 146, 290-302 (2011).
36 Choy, A. et al. The Legionella effector RavZ inhibits host autophagy through irreversible Atg8 deconjugation. Science 338, 1072-1076 (2012).
37 Jotwani, A., Richerson, D. N., Motta, I., Julca-Zevallos, O. & Melia, T. J. Approaches to the study of Atg8-mediated membrane dynamics in vitro. Methods Cell Biol 108, 93-116 (2012).
38 Wu, Z. et al. Dilation of fusion pores by crowding of SNARE proteins. Elife 6 (2017).
39 Weber, T. et al. SNAREpins: minimal machinery for membrane fusion. Cell 92, 759-772 (1998).
40 Goormaghtigh, E. & Scarborough, G. A. Density-based separation of liposomes by glycerol gradient centrifugation. Anal Biochem 159, 122-131 (1986).
41 Lundahl, P., Zeng, C. M., Lagerquist Hagglund, C., Gottschalk, I. & Greijer, E. Chromatographic approaches to liposomes, proteoliposomes and biomembrane vesicles. J Chromatogr B Biomed Sci Appl 722, 103-120 (1999).
42 Mostafavi, H. et al. Entropic forces drive self-organization and membrane fusion by SNARE proteins. Proc Natl Acad Sci USA 114, 5455-5460 (2017).
43 Ji, H. et al. Protein determinants of SNARE-mediated lipid mixing. Biophys J 99, 553-560 (2010).
44 Stratton, B. S. et al. Cholesterol Increases the Openness of SNARE-Mediated Flickering Fusion Pores. Biophys J 110, 1538-1550 (2016).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for producing uniform-size liposomes, the method comprising:
 coating a plurality of liposomes with a sorting agent to yield a plurality of density-modified liposomes of different sizes;
 separating the density-modified liposomes of different sizes using a densitometric method; and
 isolating one or more fractions of uniform-size liposomes,
 wherein the sorting agent comprises a density-modifying moiety and a targeting moiety, wherein the molecular mass of the density-modifying moiety is from 50 to 250 kDa, and
 wherein the liposomes within each of the one or more isolated fractions have a coefficient of variation of less than 15%.

2. The method of claim 1, wherein the density of the sorting agent is higher than the density of the liposome.

3. The method of claim 1, wherein the density of an individual density-modified liposome is inversely related to the radius of the individual density-modified liposome.

4. The method of claim 1, wherein the density-modifying moiety comprises a polynucleotide.

5. The method of claim 4, wherein the targeting moiety is bound to a nucleotide base within the polynucleotide.

6. The method of claim 1, wherein the density-modifying moiety forms a polynucleotide nanostructure.

7. The method of claim 1, wherein the liposomes are coated with the sorting agent under conditions where the sorting agent is present in excess so as to achieve dense coating of the liposomes.

8. The method of claim 1, wherein the targeting moiety comprises a hydrophobic molecule or a protein-specific ligand.

9. The method of claim 1, wherein the densitometric method is isopycnic centrifugation.

10. The method of claim 1, wherein the liposomes comprise a pharmaceutical agent.

11. The method of claim 1, further comprising loading the obtained liposomes with a pharmaceutical agent.

12. The method of claim 1, the method comprising:
 coating a plurality of liposomes with cholesterol-modified oligonucleotides to yield a plurality of density-modified liposomes of different sizes,
 separating the density-modified liposomes of different sizes by isopycnic centrifugation, and
 isolating one or more fractions of uniform-size liposomes.

13. The method of claim 12, wherein the cholesterol-modified oligonucleotides comprise DNA.

14. A method for producing uniform-size liposomes, the method comprising:
 coating a plurality of liposomes with a sorting agent to yield a plurality of density-modified liposomes of different sizes; and
 separating the density-modified liposomes of different sizes using a densitometric method,
 wherein the sorting agent comprises a density-modifying moiety and a targeting moiety, wherein the molecular mass of the density-modifying moiety is from 50 to 250 kDa, and wherein the density-modifying moiety is a polynucleotide, and the method further comprising separating the density-modifying moiety from the targeting moiety using a nuclease after the separating step.

15. A method for producing uniform-size liposomes, the method comprising:
 coating a plurality of liposomes with cholesterol-modified DNA oligonucleotides to yield a plurality of density-modified liposomes of different sizes;
 separating the density-modified liposomes of different sizes by isopycnic centrifugation, and
 isolating one or more fractions of uniform-size liposomes,
 wherein the cholesterol-modified DNA oligonucleotides form a six-helix-bundle rod of about 189 kD with a single cholesterol at the end of each DNA structure.

16. The method of claim 15, wherein one fraction of uniform-size liposomes is sized greater than 100 nm.

17. A method for producing uniform-size liposomes, the method comprising:
 coating a plurality of liposomes with cholesterol-modified DNA oligonucleotides to yield a plurality of density-modified liposomes of different sizes;
 separating the density-modified liposomes of different sizes by isopycnic centrifugation, and
 isolating one or more fractions of uniform-size liposomes,
 wherein the cholesterol-modified DNA oligonucleotides form a three-pointed star of about 86 kD with a single cholesterol at the end of each DNA structure.

18. The method of claim 17, wherein one fraction of uniform-size liposomes is sized less than 40 nm.

* * * * *